United States Patent
Ghosh

(10) Patent No.: US 11,657,900 B2
(45) Date of Patent: May 23, 2023

(54) METHODS FOR IDENTIFYING DNA COPY NUMBER CHANGES USING HIDDEN MARKOV MODEL BASED ESTIMATIONS

(71) Applicant: Affymetrix, Inc., Carlsbad, CA (US)

(72) Inventor: Srinka Ghosh, San Francisco, CA (US)

(73) Assignee: AFFYMETRIX, INC., Carlsbad, CA (US)

( * ) Notice: Subject to any disclaimer, the term of this patent is extended or adjusted under 35 U.S.C. 154(b) by 1042 days.

(21) Appl. No.: 16/245,165

(22) Filed: Jan. 10, 2019

(65) Prior Publication Data

US 2019/0287650 A1    Sep. 19, 2019

Related U.S. Application Data

(63) Continuation of application No. 12/143,754, filed on Jun. 20, 2008, now Pat. No. 10,229,244.

(60) Provisional application No. 60/945,132, filed on Jun. 20, 2007.

(51) Int. Cl.

| | | |
|---|---|---|
| *G16B 40/30* | (2019.01) | |
| *G16B 40/00* | (2019.01) | |
| *C12Q 1/6827* | (2018.01) | |
| *G16B 20/20* | (2019.01) | |
| *G16B 20/40* | (2019.01) | |
| *G16B 20/10* | (2019.01) | |
| *G16B 20/00* | (2019.01) | |
| *G16B 25/00* | (2019.01) | |

(52) U.S. Cl.
CPC .......... *G16B 40/30* (2019.02); *C12Q 1/6827* (2013.01); *G16B 20/10* (2019.02); *G16B 20/20* (2019.02); *G16B 20/40* (2019.02); *G16B 40/00* (2019.02); *G16B 20/00* (2019.02); *G16B 25/00* (2019.02)

(58) Field of Classification Search
None
See application file for complete search history.

(56) References Cited

U.S. PATENT DOCUMENTS

| | | |
|---|---|---|
| 5,665,549 A | 9/1997 | Pinkel et al. |
| 5,856,097 A | 1/1999 | Pinkel et al. |
| 5,965,362 A | 10/1999 | Pinkel et al. |
| 5,976,790 A | 11/1999 | Pinkel et al. |
| 6,180,349 B1 | 1/2001 | Ginzinger et al. |
| 6,268,142 B1 | 7/2001 | Duff et al. |
| 6,309,822 B1 | 10/2001 | Fodor et al. |
| 6,326,148 B1 | 12/2001 | Pauletti et al. |
| 6,335,167 B1 | 1/2002 | Pinkel et al. |
| 6,344,316 B1 | 2/2002 | Lockhart et al. |
| 6,432,648 B1 | 8/2002 | Blumenfeld et al. |
| 6,455,258 B2 | 9/2002 | Bastian et al. |
| 6,455,280 B1 | 9/2002 | Edwards et al. |
| 6,468,744 B1 | 10/2002 | Cronin et al. |
| 10,229,244 B2 * | 3/2019 | Ghosh ............... G16B 40/00 |
| 2001/0034023 A1 | 10/2001 | Stanton et al. |
| 2002/0165345 A1 | 11/2002 | Cohen et al. |

FOREIGN PATENT DOCUMENTS

WO    99/23256 A1    5/1999

OTHER PUBLICATIONS

Hu Enhanced Quantile Normalization of Microarray Data to Reduce Loss of Information in Gene Expression Profiles Biometrics vol. 63, pp. 50-59 (Year: 2007).*
Bolstad et al., "A comparison of normalization methods for high density oligonucleotide array data based on variance and bias," Bioinformatics., vol. 19, Jan. 22, 2003, pp. 185-193.
Buckley et al., "A full-coverage, high-resolution human chromosome 22 genomic microarray for clinical and research applications," Hum. Mal. Genet., vol. 11, Dec. 1, 2002, pp. 3221-3229.
Colella et al., "QuantiSNP: an Objective Bayes Hidden-Markov Model to detect and accurately map copy number variation using SNP genotyping data," Nucleic Acids Res., vol. 35, 2007, pp. 2013-2025.
Di et al., "Dynamic model based algorithms for screening and genotyping over 100K SNPs on oligonucleotide microarrays," Bioinformatics., vol. 21, May 1, 2005, pp. 1958-1963.
Draghici, "Statistical intelligence: effective analysis of high-density microarray data," Drug Discov. Today, vol. 7, Jun. 1, 2002, pp. S55-S63.
Dumur et al., "Genome-wide detection of LOH in prostate cancer using human SNP microarray technology," Genomics, vol. 81, Mar. 2003, pp. 260-269.
Ishikawa et al., "Allelic dosage analysis with genotyping microarrays," Biochem. Biophys. Res. Commun., vol. 333, Aug. 12, 2005, pp. 1309-1314.
Jacobs et al., "Genome-wide, high-resolution detection of copy number, loss of heterozygosity, and genotypes from formalin-fixed, paraffin-embedded tumor tissue using microarrays," Cancer Res., vol. 67, Mar. 15, 2007, pp. 2544-2551.
Kallioniemi et al., "Comparative genomic hybridization for molecular cytogenetic analysis of solid tumors," Science, vol. 258, Oct. 30, 1992, pp. 818-821.
Kaminski et al., "Practical approaches to analyzing results of microarray experiments," Am. J. Respir. Cell Mal. Biol., vol. 27, Aug. 2002, pp. 125-132.
Kennedy et al., "Large-scale genotyping of complex DNA," Nat. Biotechnol., vol. 21, Oct. 2003, pp. 1233-1237.
Klein et al., "Comparative genomic hybridization, loss of heterozygosity, and DNA sequence analysis of single cells," Proc. Natl. Acad. Sci. U.S.A, vol. 96, Apr. 13, 1999, pp. 4494-4499.
Knudson, Jr., "Hereditary cancer, oncogenes, and antioncogenes," Cancer Res., vol. 45, Apr. 1985, pp. 1437-1443.
Lindblad-Toh et al., "Loss-of-heterozygosity analysis of small-cell lung carcinomas using singlenucleotide polymorphism arrays," Nat. Biotechnol., vol. 18, Sep. 2000, pp. 1001-1005.

(Continued)

*Primary Examiner* — John S Brusca

(74) *Attorney, Agent, or Firm* — Mauriel Kapouytian Woods LLP; Elaine K. Lee; Michael Mauriel

(57) ABSTRACT

Methods for estimating genomic copy number and loss of heterozygosity using Hidden Markov Model based estimation are disclosed.

20 Claims, 59 Drawing Sheets

(56) References Cited

OTHER PUBLICATIONS

Lucito et al., "Detecting gene copy number fluctuations in tumor cells by microarray analysis of genomic representations," Genome Res., vol. 10, Nov. 2000, pp. 1726-1736.
Lucito et al., "Genetic analysis using genomic representations," Proc. Natl. Acad. Sci.U.S.A, vol. 95, Apr. 14, 1998, pp. 4487-4492.
Lucito et al., "Representational oligonucleotide microarray analysis: a high-resolution method to detect genome copy number variation," Genome Res., vol. 13, Oct. 2003, pp. 2291-2305.
Mei, R. et al., "Genome-wide detection of allelic imbalance using human SNPs and high-density DNA arrays," Genome Res., vol. 10, Aug. 2000, pp. 1126-1137.
Mohapatra et al., "Analyses of brain tumor cell lines confirm a simple model of relationships among fluorescence in situ hybridization, DNA index, and comparative genomic hybridization," Genes Chromosomes Cancer, vol. 20, Dec. 1997, pp. 311-319.
Nannya et al., "A robust algorithm for copy number detection using high-density oligonucleotide single nucleotide polymorphism genotyping arrays," Cancer Res., vol. 65, Jul. 15, 2005, pp. 6071-6079.
Pinkel et al., "High resolution analysis of DNA copy number variation using comparative genomic hybridization to microarrays," Nat. Genet., vol. 20, Oct. 1998, pp. 207-211.
Pollack et al., "Microarray analysis reveals a major direct role of DNA copy number alteration in the transcriptional program of human breast tumors," Proc. Natl. Acad. Sci. U.S.A, vol. 99, Oct. 1, 2002, pp. 12963-12968.
Rabiner, "A tutorial on hidden markov models and selected applications in speech recognition," Proceedings of the IEEE, vol. 77, 1989, pp. 257-286.
Schubert et al., "Single nucleotide polymorphism array analysis of flow-sorted epithelial cells from frozen versus fixed tissues for whole genome analysis of allelic loss in breast cancer," Am. J. Pathol., vol. 160, Jan. 2002, pp. 73-79.
Shadeo et al., "Comprehensive copy number profiles of breast cancer cell model genomes," Breast Cancer Res.,vol. 8, 2006, 14 pages.
Snijders et al., "Assembly of microarrays for genome-wide measurement of DNA copy number," Nat. Genet.,vol. 29, Nov. 2001, pp. 263-264.
Wodicka et al., "Genome-wide expression monitoring in *Saccharomyces cerevisiae*," Nat. Biotechnol., vol. 15, Dec. 1997, pp. 1359-1367.
www.affymetrix.com, "BRLMM: An Improved Genotype Calling Method for the GeneChip® Human Mapping 500K Array Set," Affymetrix, white paper, 2006, pp. 1-18.
Zhou et al., "Match-only integral distribution (MOID) algorithm for high-density oligonucleotide array analysis," BMC Bioinformatics.,vol. 3, 2002, pp. 1-15.
Rabbee et al., "A genotype calling algorithm for affymetrix SNP arrays," Bioinformatics, vol. 22, 2006. pp. 7-12.
Li et al., "Model-based analysis of oligonucleotide arrays: model validation, design issued and standard error application," Genome Biology, vol. 2, 2001, pp. 1-11.
Hsiao et al., "Correcting for Signal Saturation Errors in the Analysis of Microarray Data," Bio. Techniques, vol. 32, 2002, pp. 330-336.
Liu et al., "Algorithms for large-scale genotyping microarrays," Bioinformatics, vol. 19, 2003, pp. 2397-2403.
Herr et al., "High-resolution analysis of chromosomal imbalances using the Affymetrix 10K SNP genotyping chip," Genomics, vol. 85, 2005, pp. 392-400.
Jong et al., "Breakpoint identification and smoothing of array comparative genomic hybridization data," Bioinformatics vol. 20, 2004, pp. 3636-3637.
Harvell et al., "High-Resolution Array-Based Comparative Genomic Hybridization for Distinguishing Paraffin-Embedded Spitz Nevi and Melanomas," Diagnostic and Molecular Pathology, vol. 13, 2004, pp. 22-25.
Margolin et al., "CGHAnalyzer: a stand-alone software package for cancer genome analysis using array-based DNA copy number data," Bioinformatics, vol. 21, 2005, pp. 3308-3311.

\* cited by examiner

FIG. 25

| CN Matched HMM | CN Un-matched HMM |
| LOH Matched HMM | LOH Un-matched HMM |

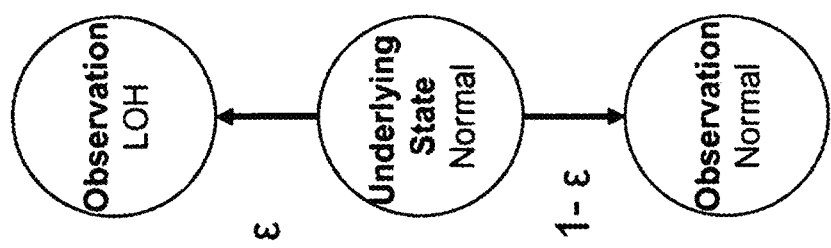
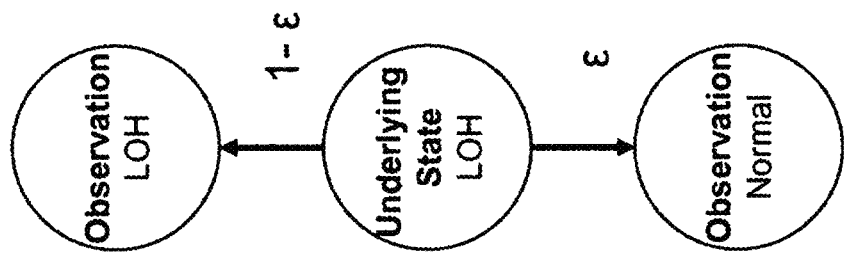
FIG. 33

METHODS FOR IDENTIFYING DNA COPY NUMBER CHANGES USING HIDDEN MARKOV MODEL BASED ESTIMATIONS

RELATED APPLICATIONS

This application is a continuation of U.S. patent application Ser. No. 14/143,754 filed Jun. 20, 2008 and claims priority to U.S. Provisional Application No. 60/945,132 filed Jun. 20, 2007. The above applications are incorporated herein by reference in their entireties for all purposes.

FIELD OF THE INVENTION

The invention is related to methods of estimating the number of copies of a genomic region that are present in a sample. Specifically, this invention provides methods, computer software products and systems for the detection of regions of chromosomal amplification and deletion from a biological sample.

BACKGROUND OF THE INVENTION

The underlying progression of genetic events which transform a normal cell into a cancer cell is characterized by a shift from the diploid to anneploid state (Albertson et al, (2003), *Nat Genet*, Vol. 34, pp. 369-76 and Lenganer et al. (1998), *Nature*, Vol. 396, pp.643-9). As a result of genomic instability, cancer cells accumulate both random and causal alterations at multiple levels from point mutations to whole-chromosome aberrations. DNA copy number changes include, but are not limited to, loss of heterozygosity (LOH) and homozygous deletions, which can result in the loss of tumor suppressor genes, and gene amplification events, which can result in cellular proto-oncogene activation. One of the continuing challenges to unraveling the complex karyotype of the tumor cell is the development of improved molecular methods that can globally catalogue LOH, gains, and losses with both high resolution and accuracy.

Numerous molecular approaches have been described to identify genome-wide LOH and copy number changes within tumors. Classical LOH studies designed to identify allelic loss using paired tumor and blood samples have made use of restriction fragment length polymorphisms (RFLP) and, more often, highly polymorphic microsatellite markers (STRS, VNTRs). The demonstration of Knudson's two-hit tumorigenesis model using LOH analysis of the retinoblastoma gene, Rb1, showed that the mutant allele copy number can vary from one to three copies as the result of biologically distinct second-hit mechanisms (Cavenee, et al. (1983), *Nature*, Vol. 305, pp.779-84.). See also *Knudson, A. G., Cancer Res*. 45, 1437-1443 (1985). Thus regions undergoing LOH do not necessarily contain DNA copy number changes.

Approaches to measure genome wide increases or decreases in DNA copy number include comparative genomic hybridization (CGH) (Kallioniemi, et al. (1992), *Science*, Vol. 258, pp.818-21.), spectral karyotyping (SKY) (Schrock, et al. (1996), *Science*, Vol. 273, pp.494-7.), fluorescence in situ hybridization (FISH) (Pinkel et al. (1988), *Proc Natl Acad Sci* USA, Vol. 85, pp.9138-42), molecular subtraction methods, such as RDA (Lisitsyn et al. (1995), *Proc Natl Acad Sci* USA, Vol. 92, pp.151-5.; Lucito et al. (1998), *Proc Natl Acad Sci* USA, Vol. 95, pp.4487-92), and digital karyotyping (Wang, et al. (2002), *Proc Natl Acad Sci* USA, Vol. 99, pp.16156-61.). CGH, perhaps the most widely used approach, uses a mixture of DNA from normal and tumor cells that have been differentially labeled with fluorescent dyes. Target DNA is competitively hybridized to metaphase chromosomes or, in array CGH, to cDNA clones (Pollack et al. (2002), *Proc Natl Acad Sci* USA, Vol. 99, pp.12963-8) or bacterial artificial chromosomes (BACs) and P1 artificial chromosomes (PACs) (Snijders et al. (2001), *Nat Genet*, Vol. 29, pp.263-4, Pinkel, et al. (1998), *Nat Genet*, Vol. 20, pp.207-11). See also, Balmain et al. *Nature Genet*. 33:238 (2003) and Fridlyand et al *BMC Cancer* 6:96 (2006). Hybridization to metaphase chromosomes, however, limits the resolution to 10-20 Mb, precluding the detection of small gains and losses. While the use of arrayed cDNA clones allows analysis of transcriptionally active regions of the genome, the hybridization kinetics may not be as uniform as when using large genomic clones. Currently, the availability of BAC clones spanning the genome limits the resolution of CGH to 1-2 Mb. CGH, however, is not well-suited to identify regions of the genome which have undergone LOH such that a single allele is present but there is no reduction in copy number.

With the completion of the human genome, single nucleotide polymorphisms (SNPs), the most common sequence variation among individuals, are emerging as the marker of choice in large-scale genetic studies due to their abundance, stability, and relative ease of scoring. These same characteristics make SNPs powerful markers for LOH studies.

SUMMARY OF THE INVENTION

Methods of estimating copy number using high density arrays of probes that are allele specific probes to single nucleotide polymorphisms are disclosed. Algorithms and computer software programs that direct computer hardware to perform the steps of the method are also disclosed. Probe intensity information is used to infer copy number. In preferred aspects a Hidden Markov Model is used to estimate copy number and to identify regions of LOH.

BRIEF DESCRIPTION OF THE DRAWINGS

The accompanying drawings, which are incorporated in and form a part of this specification, illustrate embodiments of the invention and, together with the description, serve to explain the principles of the invention:

FIG. 25 shows four possible approaches where HMM may be applied.

FIG. 33 shows emission probability for LOH with matched tumor-normal samples.

Figure 1:
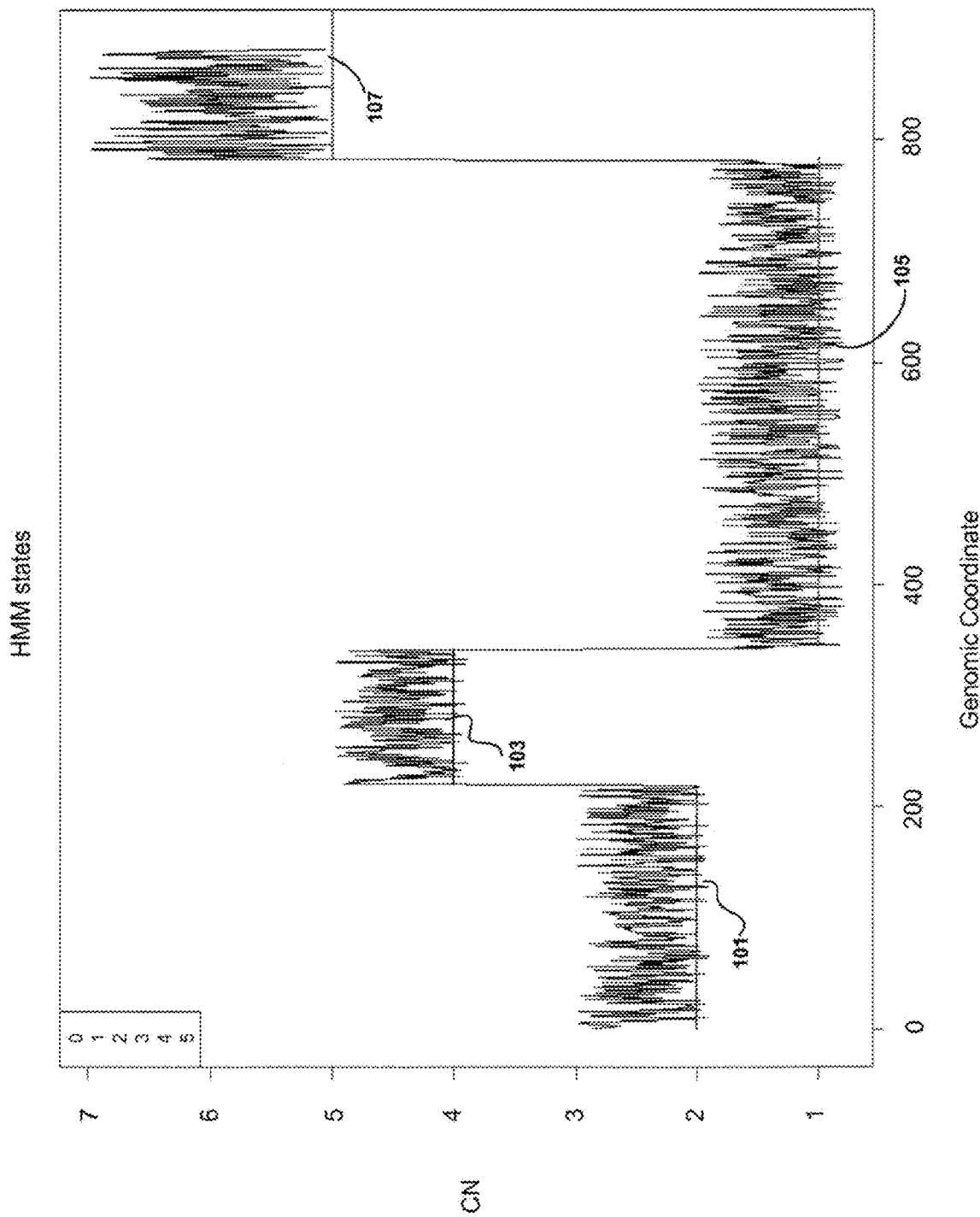
FIG. 1 is a plot of raw copy number distribution across a genomic region and illustrates change points in the distribution.

DETAILED DESCRIPTION OF THE INVENTION (A) General

The present invention has many preferred embodiments and relies on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. All references to the function log default to e as the base (natural log) unless stated otherwise (such as $\log_{10}$).

The practice of the present invention may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below.

However, other equivalent conventional procedures can, of course, also be used. Such conventional techniques and descriptions can be found in standard laboratory manuals such as *Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual* (all from Cold Spring Harbor Laboratory Press), Stryer, L. (1995) *Biochemistry* (4th Ed.) Freeman, N.Y., Gait, *"Oligonucleotide Synthesis: A Practical Approach"* 1984, IRL Press, London, Nelson and Cox (2000), *Lehninger, Principles of Biochemistry* $3^{rd}$ Ed., W. H. Freeman Pub., New York, N.Y. and Berg et al. (2002) *Biochemistry*, $5^{th}$ Ed., W. H. Freeman Pub., New York, N.Y., all of which are herein incorporated in their entirety by reference for all purposes.

The present invention can employ solid substrates, including arrays in some preferred embodiments. Methods and techniques applicable to polymer (including protein) array synthesis have been described in U.S Patent Pub. No. 20050074787, WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, which are all incorporated herein by reference in their entirety for all purposes.

Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

Nucleic acid arrays that are useful in the present invention include those that are commercially available from Affymetrix (Santa Clara, Calif.) under the brand name GeneChip®. Example arrays are shown on the website at affymetrix.com.

The present invention also contemplates many uses for polymers attached to solid substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses therefore are shown in USSN 60/319,253 (not available), and U.S. Pat. Nos. 5,856,092, 6,300,063, 5,858,659, 6,284,460, 6,361, 947, 6,368,799, 6,872,529 and 6,333,179. Other uses are embodied in U.S. Pat. Nos. 5,871,928, 5,902,723, 6,045, 996, 5,541,061, and 6,197,506.

The present invention also contemplates sample preparation methods in certain preferred embodiments. Prior to or concurrent with genotyping, the genomic sample may be amplified by a variety of mechanisms, some of which may employ PCR. See, e.g., *PCR Technology: Principles and Applications for DNA Amplification* (Ed. H. A. Erlich, Freeman Press, NY, NY, 1992); *PCR Protocols: A Guide to Methods and Applications* (Eds. Innis, et al., Academic Press, San Diego, Calif., 1990); Mattila et al., *Nucleic Acids Res.* 19, 4967 (1991); Eckert et al., *PCR Methods and Applications* 1, 17 (1991); *PCR* (Eds. McPherson et al., IRL Press, Oxford); and U.S. Pat. Nos. 4,683,202, 4,683,195, 4,800,159 4,965,188, and 5,333,675, and each of which is incorporated herein by reference in their entireties for all purposes. The sample may be amplified on the array. See, for example, U.S. Pat. No. 6,300,070 which is incorporated herein by reference.

Other suitable amplification methods include the ligase chain reaction (LCR) (for example, Wu and Wallace, *Genomics* 4, 560 (1989), Landegren et al., *Science* 241, 1077 (1988) and Barringer et al. *Gene* 89:117 (1990)), transcription amplification (Kwoh et al., *Proc. Natl. Acad. Sci.* USA 86, 1173 (1989) and WO88/10315), self-sustained sequence replication (Guatelli et al., *Proc. Nat. Acad. Sci.* USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al. 1992, Nucleic Acids Res. 20(7):1691-6, 1992, and rolling circle amplification, described in U.S. Pat. No. 5,648,245. Other amplification methods that may be used are described in, U.S. Pat. Nos. 5,242,794, 5,494,810, 4,988,617 and 6,582,938 and US Pub. No. 20030143599, each of which is incorporated herein by reference. In some embodiments DNA is amplified by multiplex locus-specific PCR. In a preferred embodiment the DNA is amplified using adaptor-ligation and single primer PCR. Other available methods of amplification, such as balanced PCR (Makrigiorgos, et al. (2002), *Nat Biotechnol*, Vol. 20, pp.936-9), may also be used.

Additional methods of sample preparation and techniques for reducing the complexity of a nucleic sample are described in Dong et al., *Genome Research* 11, 1418 (2001), in U.S. Pat. Nos. 6,361,947, 6,391,592 and U.S. Pat. Nos. 6,958,225, 6,632,611, and 6,872,529 and US Patent Pub. No. 20050079536.

Methods for conducting polynucleotide hybridization assays have been well developed in the art. Hybridization assay procedures and conditions will vary depending on the application and are selected in accordance with the general binding methods known including those referred to in: Maniatis et al. *Molecular Cloning: A Laboratory Manual* ($2^{nd}$ Ed. Cold Spring Harbor, N.Y., 1989); Berger and Kimmel *Methods in Enzymology*, Vol. 152, *Guide to Molecular Cloning Techniques* (Academic Press, Inc., San Diego, Calif., 1987); Young and Davism, *P.N.A.S*, 80: 1194 (1983). Methods and apparatus for carrying out repeated and controlled hybridization reactions have been described in U.S. Pat. Nos. 5,871,928, 5,874,219, 6,045,996 and 6,386, 749, 6,391,623 each of which are incorporated herein by reference The present invention also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent Pub. Nos. 20040012676 and 20050057676 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800, 992, 5,834,758; 5,856,092, 5,902,723, 5,936,324, 5,981, 956, 6,025,601, 6,090,555, 6,141,096, 6,185,030, 6,201,639; 6,218,803; and 6,225,625, in U.S. Patent Pub. Nos. 2004-0012676 2005-0057676 and in PCT Application PCT/US99/06097 (published as WO99/47964), each of which also is hereby incorporated by reference in its entirety for all purposes.

The practice of the present invention may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000) and Ouelette and Bzevanis *Bioinformatics: A Practical Guide for Analysis of Gene and Proteins* (Wiley & Sons, Inc., $2^{nd}$ ed., 2001).

The present invention may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911 and 6,308,170. Computer methods related to genotyping using high density microarray analysis may also be used in the present methods, see, for example, US Patent Pub. Nos. 20050250151, 20050244883, 20050108197, 20050079536 and 20050042654.

Methods for analysis of genotype using array data are described, for example, in Di, X., et al. (2005) *Bioinformatics*, 21, 1958-1963, Liu, W., et al. (2003) *Bioinformatics*, 19, 2397-2403 and Rabbee and Speed (2006) *Bioinformatics* 22:7-12. Methods for copy number analysis based on hybridization to arrays of oligonucleotides have been disclosed, for example, in US Patent Pub. Nos. 20040157243, 20060134674, 20050130217, and 20050064476.

Additionally, the present invention may have preferred embodiments that include methods for providing genetic information over networks such as the Internet as shown in U.S. Patent applications 20020183936, 20030100995, 20030120432, 20040002818, and. 20040049354.

(B) Definitions

Nucleic acids according to the present invention may include any polymer or oligomer of pyrimidine and purine bases, preferably cytosine, thymine, and uracil, and adenine and guanine, respectively. (See Albert L. Lehninger, *Principles of Biochemistry*, at 793-800 (Worth Pub. 1982) which is herein incorporated in its entirety for all purposes). Indeed, the present invention contemplates any deoxyribonucleotide, ribonucleotide or peptide nucleic acid component, and any chemical variants thereof, such as methylated, hydroxymethylated or glucosylated forms of these bases, and the like. The polymers or oligomers may be heterogeneous or homogeneous in composition, and may be isolated from naturally occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states.

An oligonucleotide or polynucleotide is a nucleic acid ranging from at least 2, preferably at least 8, 15 or 20 nucleotides in length, but may be up to 50, 100, 1000, or 5000 nucleotides long or a compound that specifically hybridizes to a polynucleotide. Polynucleotides of the present invention include sequences of deoxyribonucleic acid (DNA) or ribonucleic acid (RNA) or mimetics thereof which may be isolated from natural sources, recombinantly produced or artificially synthesized. A further example of a polynucleotide of the present invention may be a peptide nucleic acid (PNA). (See U.S. Pat. No. 6,156,501 which is hereby incorporated by reference in its entirety.) The invention also encompasses situations in which there is a nontraditional base pairing such as Hoogsteen base pairing which has been identified in certain tRNA molecules and postulated to exist in a triple helix. "Polynucleotide" and "oligonucleotide" are used interchangeably in this application.

The term fragment refers to a portion of a larger DNA polynucleotide or DNA. A polynucleotide, for example, can be broken up, or fragmented into, a plurality of fragments. Various methods of fragmenting nucleic acid are well known in the art. These methods may be, for example, either chemical or physical in nature. Chemical fragmentation may include partial degradation with a DNase; partial depurination with acid; the use of restriction enzymes; intron-encoded endonucleases; DNA-based cleavage methods, such as triplex and hybrid formation methods, that rely on the specific hybridization of a nucleic acid segment to localize a cleavage agent to a specific location in the nucleic acid molecule; or other enzymes or compounds which cleave DNA at known or unknown locations. Physical fragmentation methods may involve subjecting the DNA to a high shear rate. High shear rates may be produced, for example, by moving DNA through a chamber or channel with pits or spikes, or forcing the DNA sample through a restricted size flow passage, e.g., an aperture having a cross sectional dimension in the micron or submicron scale. Other physical methods include sonication and nebulization. Combinations of physical and chemical fragmentation methods may likewise be employed such as fragmentation by heat and ion-mediated hydrolysis. See for example, Sambrook et al., "Molecular Cloning: A Laboratory Manual," $3^{rd}$ Ed. Cold Spring Harbor Laboratory Press, Cold Spring Harbor, N.Y. (2001) ("Sambrook et al.) which is incorporated herein by reference for all purposes. These methods can be optimized to digest a nucleic acid into fragments of a selected size range. Useful size ranges may be from 100, 200, 400, 700 or 1000 to 500, 800, 1500, 2000, 4000 or 10,000 base pairs. However, larger size ranges such as 4000, 10,000 or 20,000 to 10,000, 20,000 or 500,000 base pairs may also be useful.

"Genome" designates or denotes the complete, single-copy set of genetic instructions for an organism as coded into the DNA of the organism. A genome may be multi-chromosomal such that the DNA is cellularly distributed among a plurality of individual chromosomes. For example, in human there are 22 pairs of chromosomes plus a gender associated XX or XY pair.

The term "chromosome" refers to the heredity-bearing gene carrier of a living cell which is derived from chromatin and which comprises DNA and protein components (especially histones). The conventional internationally recognized individual human genome chromosome numbering system is employed herein. The size of an individual chromosome can vary from one type to another with a given multichromosomal genome and from one genome to another. In the case of the human genome, the entire DNA mass of a given chromosome is usually greater than about 100,000,000 bp. For example, the size of the entire human genome is about $3 \times 10^9$ bp. The largest chromosome, chromosome no. 1, contains about $2.4 \times 10^8$ bp while the smallest chromosome, chromosome no. 22, contains about $5.3 \times 10^7$ bp.

A "chromosomal region" is a portion of a chromosome. The actual physical size or extent of any individual chromosomal region can vary greatly. The term "region" is not necessarily definitive of a particular one or more genes because a region need not take into specific account the particular coding segments (exons) of an individual gene.

The term subset or representative subset refers to a fraction of a genome. The subset may be 0.1, 1, 3, 5, 10, 25, 50 or 75% of the genome. The partitioning of fragments into subsets may be done according to a variety of physical characteristics of individual fragments. For example, fragments may be divided into subsets according to size, according to the particular combination of restriction sites at the ends of the fragment, or based on the presence or absence of one or more particular sequences.

An "array" comprises a support, preferably solid, with nucleic acid probes attached to the support. Preferred arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 5,800,992, 6,040,193, 5,424,186 and Fodor et al., Science, 251:767-777 (1991). Each of which is incorporated by reference in its entirety for all purposes.

Arrays may generally be produced using a variety of techniques, such as mechanical synthesis methods or light directed synthesis methods that incorporate a combination of photolithographic methods and solid phase synthesis methods. Techniques for the synthesis of these arrays using mechanical synthesis methods are described in, e.g., U.S. Pat. Nos. 5,384,261, and 6,040,193, which are incorporated herein by reference in their entirety for all purposes. Although a planar array surface is preferred, the array may be fabricated on a surface of virtually any shape or even a multiplicity of surfaces. Arrays may be nucleic acids on beads, gels, polymeric surfaces, fibers such as optical fibers, glass or any other appropriate substrate. (See U.S. Pat. Nos. 5,770,358, 5,789,162, 5,708,153, 6,040,193 and 5,800,992, which are hereby incorporated by reference in their entirety for all purposes.)

Preferred arrays are commercially available from Affymetrix under the brand name GENECHIP® and are directed to a variety of purposes, including genotyping and gene expression monitoring for a variety of eukaryotic and prokaryotic species. (See Affymetrix Inc., Santa Clara and their website at affymetrix.com.) Methods for preparing sample for hybridization to an array and conditions for hybridization are disclosed in the manuals provided with the arrays, for example, for expression arrays the GENECHIP Expression Analysis Technical Manual (PN 701021 Rev. 5) provides detailed instructions for 3' based assays and the GeneChip® Whole Transcript (WT) Sense Target Labeling Assay Manual (PN 701880 Rev. 2) provides whole transcript based assays. The GeneChip Mapping 100K Assay Manual (PN 701694 Rev. 3) provides detailed instructions for sample preparation, hybridization and analysis using genotyping arrays. Each of these manuals is incorporated herein by reference in its entirety.

An allele refers to one specific form of a genetic sequence (such as a gene) within a cell, an individual or within a population, the specific form differing from other forms of the same gene in the sequence of at least one, and frequently more than one, variant sites within the sequence of the gene. The sequences at these variant sites that differ between different alleles are termed "variances", "polymorphisms", or "mutations". At each autosomal specific chromosomal location or "locus" an individual possesses two alleles, one inherited from one parent and one from the other parent, for example one from the mother and one from the father. An individual is "heterozygous" at a locus if it has two different alleles at that locus. An individual is "homozygous" at a locus if it has two identical alleles at that locus.

Polymorphism refers to the occurrence of two or more genetically determined alternative sequences or alleles in a population. A polymorphic marker or site is the locus at which divergence occurs. Preferred markers have at least two alleles, each occurring at frequency of preferably greater than 1%, and more preferably greater than 10% or 20% of a selected population. A polymorphism may comprise one or more base changes, an insertion, a repeat, or a deletion. A polymorphic locus may be as small as one base pair. Polymorphic markers include restriction fragment length polymorphisms, variable number of tandem repeats (VNTR's), hypervariable regions, minisatellites, dinucleotide repeats, trinucleotide repeats, tetranucleotide repeats, simple sequence repeats, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms. A polymorphism between two nucleic acids can occur naturally, or be caused by exposure to or contact with chemicals, enzymes, or other agents, or exposure to agents that cause damage to nucleic acids, for example, ultraviolet radiation, mutagens or carcinogens. Single nucleotide polymorphisms (SNPs) are positions at which two alternative bases occur at appreciable frequency (>1%) in the human population, and are the most common type of human genetic variation.

The term genotyping refers to the determination of the genetic information an individual carries at one or more positions in the genome. For example, genotyping may comprise the determination of which allele or alleles an individual carries for a single SNP or the determination of which allele or alleles an individual carries for a plurality of SNPs. For example, a particular nucleotide in a genome may be an A in some individuals and a C in other individuals. Those individuals who have an A at the position have the A allele and those who have a C have the C allele. In a diploid organism the individual will have two copies of the sequence containing the polymorphic position so the individual may have an A allele and a C allele or alternatively two copies of the A allele or two copies of the C allele. Those individuals who have two copies of the C allele are homozygous for the C allele, those individuals who have two copies of the A allele are homozygous for the C allele, and those individuals who have one copy of each allele are heterozygous. The array may be designed to distinguish between each of these three possible outcomes. A polymorphic location may have two or more possible alleles and the array may be designed to distinguish between all possible combinations.

Linkage disequilibrium or allelic association means the preferential association of a particular allele or genetic marker with a specific allele, or genetic marker at a nearby chromosomal location more frequently than expected by chance for any particular allele frequency in the population. For example, if locus X has alleles a and b, which occur at equal frequency, and linked locus Y has alleles c and d, which occur at equal frequency, one would expect the combination ac to occur at a frequency of 0.25. If ac occurs more frequently, then alleles a and c are in linkage disequilibrium. Linkage disequilibrium may result, for example, because the regions are physically close, from natural selection of certain combination of alleles or because an allele has been introduced into a population too recently to have reached equilibrium with linked alleles. A marker in linkage disequilibrium can be particularly useful in detecting susceptibility to disease (or other phenotype) notwithstanding that the marker does not cause the disease. For example, a marker (X) that is not itself a causative element of a disease, but which is in linkage disequilibrium with a gene (including regulatory sequences) (Y) that is a causative element of a phenotype, can be detected to indicate susceptibility to the disease in circumstances in which the gene Y may not have been identified or may not be readily detectable.

Normal cells that are heterozygous at one or more loci may give rise to tumor cells that are homozygous at those loci. This loss of heterozygosity may result from structural deletion of normal genes or loss of the chromosome carrying the normal gene, mitotic recombination between normal and mutant genes, followed by formation of daughter cells homozygous for deleted or inactivated (mutant) genes; or loss of the chromosome with the normal gene and duplication of the chromosome with the deleted or inactivated (mutant) gene.

A homozygous deletion is a deletion of both copies of a gene or of a genomic region. Diploid organisms generally have two copies of each autosomal chromosome and therefore have two copies of any selected genomic region. If both copies of a genomic region are absent the cell or sample has a homozygous deletion of that region. Similarly, a hemizygous deletion is a deletion of one copy of a gene or of a genomic region.

Genetic rearrangement occurs when errors occur in DNA replication and cross over occurs between nonhomologous regions resulting in genetic material moving from one chromosomal location to another. Rearrangement may result in altered expression of the genes near the rearrangement.

An aneuploid is a cell whose chromosomal constitution has changed from the true diploid, for example, extra copies of a chromosome or chromosomal region.

An individual is not limited to a human being, but may also include other organisms including but not limited to mammals, plants, bacteria or cells derived from any of the above.

The Whole Genome Sampling Assay (WGSA) reduces the complexity of a nucleic acid sample by amplifying a subset of the fragments in the sample. A nucleic acid sample is fragmented with one or more restriction enzymes and an adapter is ligated to both ends of the fragments. A primer that is complementary to the adapter sequence is used to amplify the fragments using PCR. During PCR fragments of a selected size range are selectively amplified. The size range may be, for example, 400-800 or 400 to 2000 base pairs. Fragments that are outside the selected size range are not efficiently amplified.

The fragments that are amplified by WGSA may be predicted by in silico digestion and an array may be designed to genotype SNPs that are predicted to be amplified. Genotyping may be done by allele specific hybridization with probes that are perfectly complementary to individual alleles of a SNP. A set of probes that are complementary to the region surrounding each SNP may be present on the array. Perfect match probes are complementary to the target over the entire length of the probe. Mismatch probes are identical to PM probes except for a single mismatch base. The mismatch position is typically the central position so for a 25 base probe the mismatch is position 13.

The methods may be combined with other methods of genome analysis and complexity reduction. Other methods of complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592, 6,458,530 6,872,529, 6,958,225, and 6,632,611 and U.S. Patent Pub. Nos. 20030039069, 2004-0067493 and 2004-0067493, which are incorporated herein by reference in their entireties.

The design and use of allele-specific probes for analyzing polymorphisms is described by e.g., Saiki et al., *Nature* 324, 163-166 (1986); Dattagupta, EP 235,726, Saiki, and WO 89/11548. Allele-specific probes can be designed that hybridize to a segment of target DNA from one individual but do not hybridize to the corresponding segment from another individual due to the presence of different polymorphic forms in the respective segments from the two individuals. Hybridization conditions should be sufficiently stringent that there is a significant difference in hybridization intensity between alleles, and preferably an essentially binary response, whereby a probe hybridizes to only one of the alleles.

A regression tree is a type of decision tree that deal with continuous variables. Regression trees are non-parametric models, an advantage of which is a high computational efficiency and a good compromise between comprehensibility and predictive accuracy. The regression tree method can be applied to very large datasets in which only a small proportion of the predictors are valuable for classification. See Breiman et al. *Classification and Regression Trees*, Wardsworth. 1984.

A "translocation" or "chromosomal translocation" is a chromosome abnormality caused by rearrangement of parts between nonhomologous chromosomes. The two most common types of translocations are reciprocal (also known as non-Robertsonian) and Robertsonian. Reciprocal translocations result in an exchange of material between nonhomologous chromosomes and are usually harmless. Robertsonian translocations involve two acrocentric chromosomes (chromosomes with centromeres near their ends) that fuse near the centromere region with loss of the short arms. Carriers of Robertsonian translocations are phenotypically normal but have increase risk of miscarriages or abnormal offspring. Translocations can be balanced (in an even exchange of material with no genetic information extra or missing, and ideally full functionality) or unbalanced (where the exchange of chromosome material is unequal resulting in extra or missing genes).

A hidden Markov model (HMM) is a statistical model where the system being modeled is assumed to be a Markov process with unknown parameters, and the challenge is to determine the hidden parameters from the observable parameters. The extracted model parameters can then be used to perform further analysis, for example, for pattern recognition applications. A HMM can be considered as the simplest dynamic Bayesian network. In a regular Markov model, the state is directly visible to the observer, and therefore the state transition probabilities are the only parameters. In a hidden Markov model, the state is not directly visible, but variables influenced by the state are visible. Each state has a probability distribution over the possible output values. Therefore the sequence of values generated by an HMM gives some information about the sequence of states. Hidden Markov models are especially known for their application in temporal pattern recognition such as speech, handwriting, gesture recognition and bioinformatics. See Lior Pachter and Bernd Sturmfels, Algebraic Statistics for Computational Biology, Cambridge University Press, 2005, ISBN 0-521-85700-7, Eddy, *Nature Biotechnology* 22:1315-1316 (2005) and Pavel Pevzner, Computational Molecular Biology: An Algorithmic Approach, MIT Press, 2000, especially pp. 145-149. See also, Rabiner, L, A Tutorial on Hidden Markov Models and Selected Applications in Speech Recognition, Proceedings of the IEEE, Vol 77, pp 257-86. (1989). A HMM is typically defined by a set of hidden states, a matrix of state transition probabilities and a matrix of emission probabilities. Each hidden state has different statistical properties Ergodic theory is a mathematical concept wherein a measure-preserving transformation T on a probability space is said to be ergodic if the only measurable sets invariant under T have measure 0 or 1. Another term for this property is metrically transitive. Ergodic theory is the study of ergodic transformations. Ergodic theory forms the basis for the work now referred to as chaos theory.

(C) A Hidden Markov Model Based Estimation of Chromosomal Copy Number Aberrations and LOH Genetic alterations including in copy number, for example, allelic imbalances, chromosomal copy number changes, such as amplifications, deletions, aneuploidy, loss of heterozygosity, and micro-satellite instability are often found to be associated with a disease state, for example, cancer. It has been observed that alterations in chromosomal copy number and loss of heterozygosity (LOH) are forms of genetic changes that often signal the activation of oncogenes and inactivation of tumor suppressor genes (anti-oncogenes). Variations in the form of copy number polymorphisms (CNP) can also occur in normal individuals. Identification of the loci implicated in these aberrations can generate anchor points which facilitate oncogenomics and toxicogenomics studies. Subsequently the shared LOH and aberrant CN regions can be used to partition the transcriptome data and track the differential transcript expression in the affected genomic segments. Locating and exploring such alteration events is an important research approach toward understanding the cause and progression of disease.

For diploid organisms, the abnormal chromosomal state results when the normal diploid distribution is perturbed, resulting in changes that can include, for example, deletions, amplifications and translocations. Deletions can be of a partial chromosome ranging from micro-deletions on the order of several kb to macro-deletions of mega bases, entire arms of a chromosome or entire chromosomes. Amplifications can range from partial chromosomal amplifications to gains of a single copy of a chromosome to multiple copy gains of one or more chromosomes. Translocations generally comprise parts of a first chromosome being translocated to another chromosome.

Methods for estimating copy number using high density oligonucleotide arrays have been disclosed. See, for example, US Patent Pub. Nos. 2006-0134674 A1, 2005-0130217 A1, 2005-0064476 A1, 2006-0194243 A1, 2006-0035258 and 2004-0157243 A1, which are incorporated herein by reference in their entireties.

For many of the methods disclosed herein a distribution of log2ratios derived from the intensity measure for the allele specific probes for a given region in a test or unknown sample compared to a normal sample is used to estimate copy number. As shown in FIG. 1, this generates a raw CN distribution across the genome or a genomic region. The plot in FIG. 1 shows the genomic coordinate on the X-axis and the copy number distribution states of intensity ratios on the Y-axis. Change points in the distribution along the genomic coordinate axis can be identified to locate discrete regions of the genome that have an alteration in CN. CN states are assigned based on the predicted log2(sample/reference). State 2 is the normal or copy neutral and has a $\log_2$ approximately equal to 0.0 ($\log_2(2/2)=\sim 0$). State 1 is the hemizygous deletion state and is predicted to have a $\log_2$ of about $-1$. State 3 is a single copy gain ($\log_2(3/2)=\sim 0.58$). State 4 is 2 copy gain ($\log_2(4/2)=\sim 1$).

A Hidden Markov Model (HMM) based framework to quantify allele-specific copy-number (ASCN), total copy number (TCN) changes and LOH is disclosed herein. In many embodiments, the Affymetrix, GENECHIP human mapping 500K array platform which provides consistently high coverage for NspI and StyI restriction enzymes, with a median inter-SNP distance of 2.5 kb may be used for the analysis. Incorporation of the disclosed methods significantly improves the copy-number estimation, even for minimally smoothed data. The methods include 1) optimization of global reference estimation; 2) a non-stationary transition matrix which incorporates inter-SNP distances; and 3) an expectation-maximization based approach for partitioning the different copy number states. These algorithmic enhancements are particularly beneficial for accurate identification of deletions. The accuracy of delineating change-points, where change points correspond to switching in copy number states, is enhanced by adopting a Hidden Semi-Markov framework where the duration density for the SNPs in each of the states can be explicitly modeled. LOH and aberrant CN regions are derived from both paired (tumor-normal) and unpaired samples. The analysis correlates the association and the extent of localization of the ASCN and LOH changes. Estimation of LOH changes is possible via an ethnicity matched or unmatched and family matched or unmatched manner.

For copy number analysis, the methods provide a genome-wide estimation of the copy-number status in normal, paired tumor-normal and tumor versus pooled normal samples. The methods provide identification of the SNP markers where copy-number changes relative to the normal state are observed.

For LOH the methods provide identification of SNP markers which correspond to regions of LOH as well as segmentation of the regions of LOH and regions of retention of heterozygosity. The methods may be applied to the comparison of paired tumor-normal samples as well as tumor to pooled normal comparisons. The tumor versus pooled normal estimation can be done in an ethnicity versus un-matched fashion, enabling the user to estimate the effects of contamination due to inter-population sampling.

The methods disclosed herein may be used for analysis of unpaired samples or paired tumor-normal samples. For unpaired samples, samples that are potentially unrelated and may span a diverse population are analysis together. The methods for analyzing unpaired samples are preferably used for total copy number (TCN) and LOH estimates. For paired tumor-normal samples the tumor and normal control are derived from tissues of the same individual, the normal preferably being obtained from blood and the tumor from tumor tissue. The paired methods are preferably used to generate TCN, ASCN or LOH estimates.

Figure 2:
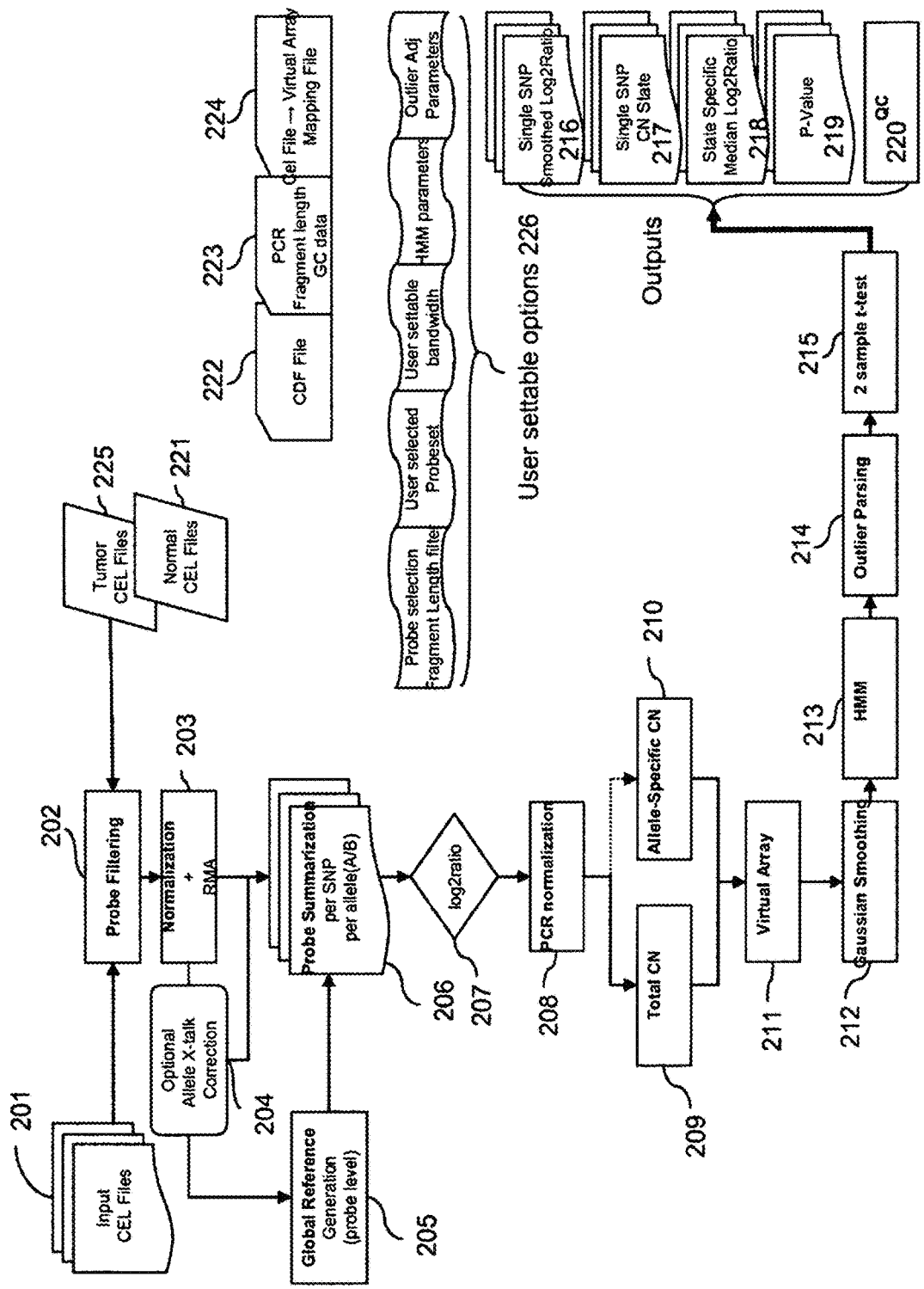
FIG. 2 is a workflow for copy number analysis.
Figure 3:
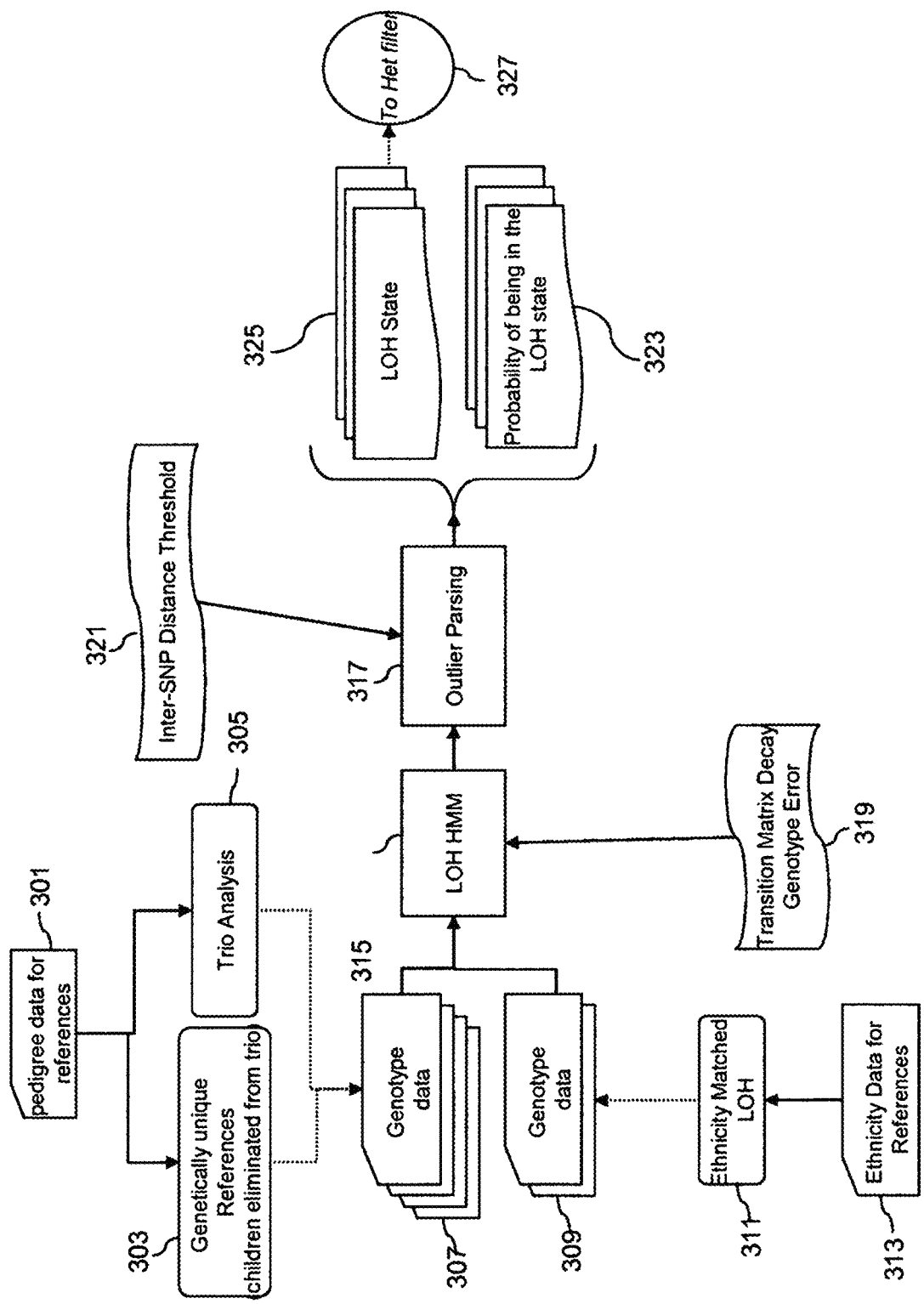
FIG. 3 is a workflow for LOH analysis.

In general the methods include four basic workflows. The basic flowcharts are shown in FIGS. 2 and 3. FIG. 2 shows the copy number (CN) flowchart and FIG. 3 shows the LOH flowchart. The shaded boxes are optional steps. The workflows are similar for paired and un-paired but differences will be discussed below.

The workflow shown in FIG. 2 shows probe level steps 202, 203 and 205; SNP level steps 206-215; input files 201, 221, 222, 223, 224 and 225, user settable options 226, outputs 216-220 and optional step 204. The allele cross talk correction is calculated as a per probe term.

Each of the Copy number and LOH algorithms may be used with two preferred workflows. One workflow, handles the scenario where the tumor and normal samples are obtained from the same person and is referred to as the matched (or paired) workflow. The un-matched (un-paired) workflow refers to the case where the test sample is compared against a pooled set of normal references.

In a preferred aspect the analysis is performed using PM only probes and the MM probes present on the current 500/100/10K arrays are not utilized. The SNPs may be pre-filtered based on the size of the PCR fragment they are derived from or their GC content. This enables handling of fresh-frozen paraffin embedded samples, where the integrity and quality of the underlying DNA is often questionable. SNPs or probes may be filtered on the basis of a variety of QC metrics, for example, probes which are saturated (scanner and/or chemical saturation) can be eliminated from the analysis. The algorithm also enables Copy Number estimation using a set of pre-filtered SNPs which might be of particular interest to the researcher.

Figure 4:
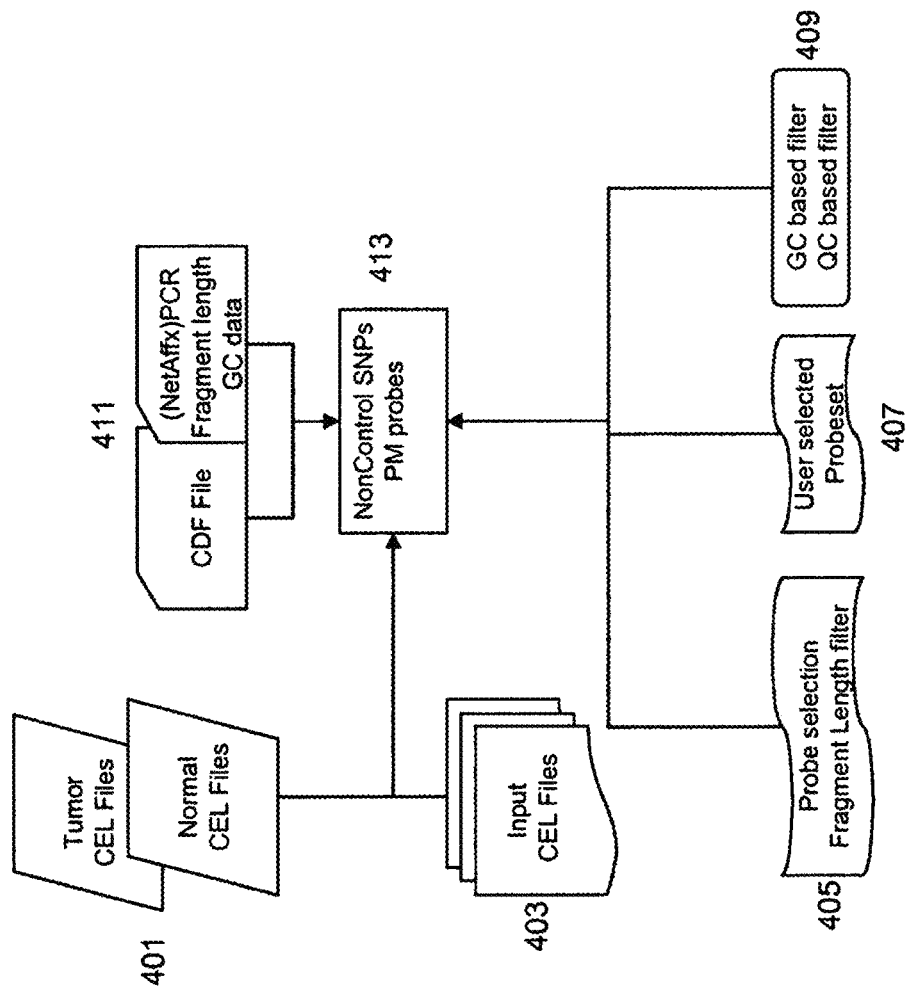
FIG. 4 is a workflow for probe filtering for PCR correction using covariates GC content of PCR fragment and length of PCR fragments.

FIG. 4 shows a workflow representing step 1 of one embodiment of the method. Input files containing intensities [401 and 403], CDF files, PCR fragment lengths and GC data [411] may be used. The filters may include probe selection fragment length filter [405], a user selected probe-set filter [407] and optionally GC or QC based filters. In this step the data to be used is subjected to one or more user defined filters to obtain a set of SNPs and probes for further analysis [413]. The SNPs and probes can be filtered using one or more quality metrics, for example, probes that are saturated, for example, scanner, chemical or enzymatic saturation can be eliminated from the subsequent analysis. SNPs can be filtered, for example, based on the size of the PCR fragment, GC content of the region surrounding the SNP (see Freeman et al., Genome Res. 16:949-61 (2006), and Nannya et al., Cancer Res. 65:6071-9 (2005)) or other indicators of SNP performance. In particular, samples that are derived from fresh-frozen paraffin embedded samples, where the integrity and quality of the underlying DNA is uncertain, may be subjected to filters based on fragment length. The intensity measurements that are used are for the perfect match probes and not the mismatch or control probes. The output of this step is a data file of intensities for the selected probes for the selected SNPs (SNPs and probes that were not filtered out during this step) along with a list of the selected SNPs and probes.

The list of SNPs and probes from FIG. 4 is then input to the second step (shown in FIG. 5). Filtered SNP and probe information from FIG. 4 (413) is applied to normalization and generation of a reference (either matched or virtual). A ratio of the intensities for the probes for a selected SNP in the tumor sample to the intensity of the probes for the same SNP in the normal sample is obtained. This ratio is calculated for each of the SNPs and each ratio value is log2 transformed.

In case of the matched (or paired analysis) the normal tissue obtained from the same person (as the tumor sample is acquired from) serves as the specific reference. In case of the un-matched, since no matched dataset is available a pooling approach is taken, whereby a global (virtual) reference is generated from a set of normal female samples. By undertaking a pooled approach, impact from outliers, random variations across the samples can be mitigated.

As described earlier, the estimation of copy number is essentially generating a ratio of the SNP intensity in the tumor sample to the intensity of the same SNP in the normal tissue or reference. This ratio is log2 transformed and is performed for all SNPs on the array.

In preferred embodiments, probe-level quantile normalization is applied to the data. Hierarchical clustering data generated for an all sample versus all sample Spearman's correlation coefficient was generated for 40 normal male samples generated as part of a study researching the effect of a variety of experimental covariates. These covariates used were operators, scanners, sample replicates, and DNA sources. Dendrograms were generated before and after quantile normalization. The dendrogram of the correlation data prior to the quantile normalization did not shown any strong correlations in the experiment. The dendrogram post quantile normalization showed 4 strong correlative blocks corresponding to the samples from the same DNA sources (there were 4 sources in total). Quantile normalization is quite effective in removal of experimental batch artifacts. The dendrograms also identified two samples with the lowest correlations to the remainder of the samples in the sample set. In some embodiments of the CN/LOH analysis, a threshold on the all-versus-all correlation measure is used to filter out sub-optimal samples.

In some embodiments the global reference that is created from a pool of normal samples is optimized using quantile normalization. In one dataset of 40 samples the distribution of the all-versus-all Spearman's correlation coefficient was calculated and the overall median distribution of the coefficient was found to be less than 0.6 with 4 samples being distinct outliers. After quantile normalization the median correlation coefficient improved to greater than 0.7 and the correlations observed for the outliers were improved.

In one aspect, an optimization method is employed to generate the optimal global reference by sampling at random from a set of available references. In one aspect the method builds upon fundamental methods of numerical analysis, but unlike previous methods the test has been implemented to address the issue dynamically. A minimum number of cel files required to generate a stable "sketch" normalization distribution may be identified. In one embodiment the log of the probe intensity is plotted on the x-axis and the density on the y-axis. The sketch normalization is the distribution against which all the cel files are quantile normalized. Stabilization of the sketch normalization is tested, starting with a nominal number of files, for example 2 and increasing the set gradually until the difference in the normalization difference converges to a small number. In the observed data for a titration based on 2, 5, 10, 15, 20, 25, 30, 35 and 38 samples, the convergence was reached at approximately 25 cel files (or 25 different samples). Finally, this approach obviates the need for selection of optimal cel files as reference, provided the cel files are quantile normalized to the final sketch. In a preferred embodiment, a random sampling of 25 cel files suffices is used to generate a global or virtual reference.

In some embodiments a PCR normalization method as previously described, may be included. See Freeman et al., Genome Res. 16:949-61 (2006), and Nannya et al., Cancer Res. 65:6071-9 (2005)) The theory behind the PCR normalization is quadratic correction using the covariates of GC content of PCR fragments and length of PCR fragments. The implementation of the this concept in the software CNAT V4.0 uses the singular value decomposition method and the normalization is performed via a linear model fit and also combines the two different covariates or predictors in a single equation, as shown via {q(x,y)}. The authors of the correction implemented the methodology in two steps as shown via equation p(x). In one embodiment, the equations are as follows:

$$\Lambda_i^{1,2} = \log_2\left(\frac{S_i^1}{S_i^2}\right) \text{ for ith SNP}$$

$$\Lambda_i^{1,2} = {}^c A_i^{1,2} + p(x)$$

$$p(x) = \sum_{j=1}^{2}(a_j + b_j x_j + c_j x_j^2) \text{ where } j = GC, \text{ fragment length}$$

$$q(x, y)) = (A + bx + b'y + cx^2 + c'y^2) \text{ where } x = GC/y = \text{fragment length}$$

Where $^c A_i^{1,2}$ represents the corrected copy number, p(x) represents PCR amplification kinetics and $x_1$ and $x_2$ represent the length and GC content of the fragment that contains SNP and coefficients $a_1$, $a_2$, $b_1$, $b_2$, $c_1$ and $c_2$ are determined by a series of linear regressions from the observed log 2 ratios. In preferred aspects a more robust, non-linear regression is performed. This makes a significant difference to fitting the tails of the distribution.

Figure 5A:
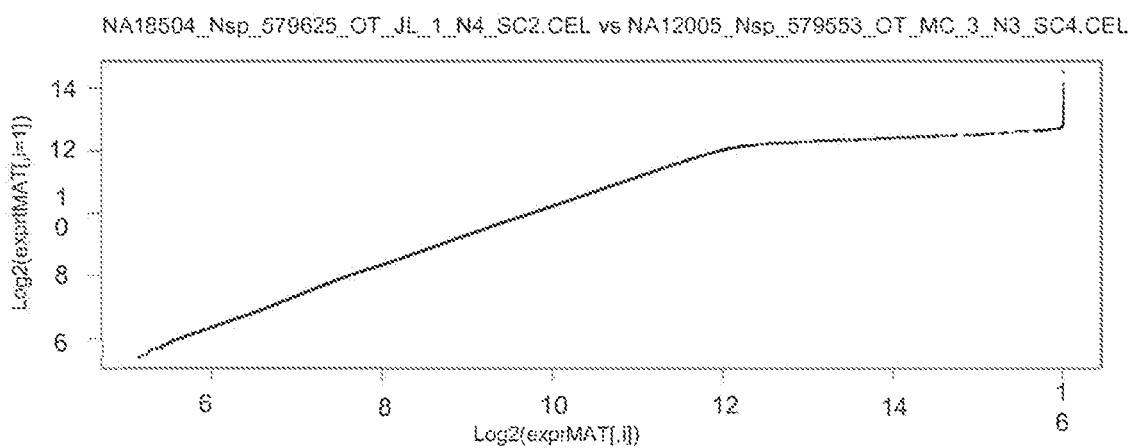
FIG. 5A and FIG. 5B illustrate saturation curves for two different probes over a range of analysis.
Figure 5B:
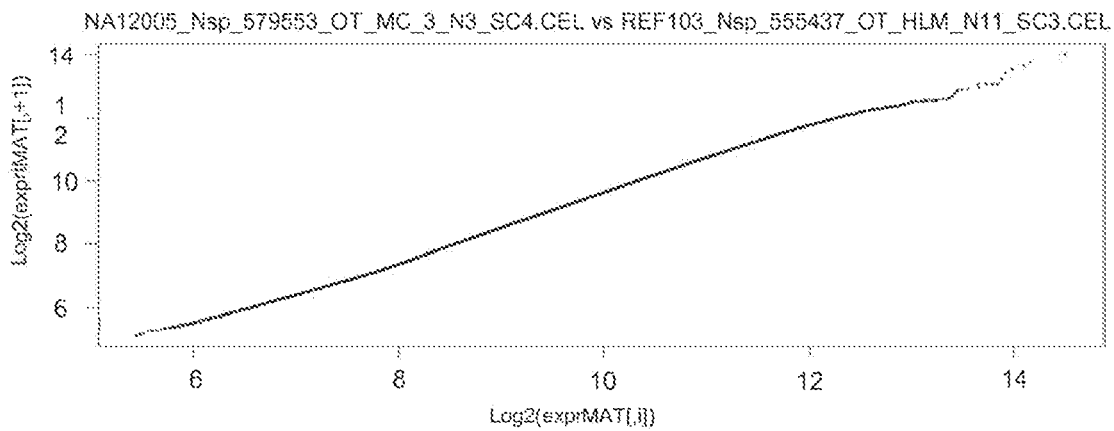

FIG. 4 shows a workflow for probe filtering. Analysis is performed using perfect match probes and does not require the use of mismatch probes. SNPs can also be pre-filtered to remove SNPs that may not perform as well, for example, SNPs that are on PCR fragments within a selected range or SNPs that have similar GC content may be selected for analysis while SNPs that are on the array but don't meet the pre-selected requirements may be left out of the analysis. Pre-filtering based on fragment size or GC content facilitates analysis of fresh-frozen paraffin embedded samples or other samples where the integrity or quality of the DNA may be compromised. SNPs or probes can also be filtered on the basis of other QC or user defined metrics. FIG. 5A shows a probe that shows saturation, for example scanner or chemical saturation, after about 12, while FIG. 5B shows a probe that performs well over the range of the analysis.

When the analysis is performed using Affymetrix GENECHIP Mapping arrays the input files are CEL files with Perfect Match and Mismatch {PM, MM} intensities and genotype calls {AA, AB, BB} generated using the Dynamic Model (DM) algorithm (Di X, et al, Bioinformatics, Vol. 21(9), pp 1958-63. (2005)) or the Bayesian Robust Linear Model with Mahalanobis (BRLMM) distance classified algorithm (see, BRLMM: an Improved Genotype Calling Method for the GeneChip® Human Mapping 500K Array Set, Affymetrix white paper. (2006), available on the Affymetrix website).

For CN estimation the steps are generally as follows: (1) probe and SNP level filtering, (2) probe-level normalization of signal intensity, (3) allele-specific summarization for each SNP, (4) global reference generation for un-paired experiments, (5) raw CN estimation, (6) PCR normalization, (7) virtual set generation, (8) Gaussian smoothing, (9) HMM based segmentation, (10) P-value estimation and (11) total versus allele-specific CN estimation.

CN analysis is preferably performed using only perfect match probes, for example, the PM probes on the mapping arrays (10K, 50K, 250K) so probes that are not PM can be filtered out. SNPs can be filtered based on a number of criteria, including the length of the PCR fragment the SNP resites on, the GC content or sequence specificity or other QC metrics. PCR fragment length based filtration may be particularly useful for CN estimation in degraded samples such as FFPE samples (see, Jacobs S et al, Cancer Res. 2007 March 15; 67(6):2544-51.). The fragment length filter is particularly applicable when using the WGSA amplification method because SNPs on larger fragment lengths may not amplify as efficiently as SNPs on smaller fragments. The fragment sizes are defined by the proximity of the selected restriction sites, for example, XbaI for the 10K arrays. Similarly the GC content of a fragment may alter the efficiency of amplification and bias the CN estimation and can be taken into consideration when filtering SNPs. SNPs can also be filtered out if they show a high level of "no calls" or are error prone. Other user defined metrics can be used to remove SNPs from the analysis prior to the next step.

| Array Resolution | Restriction Enzyme | PCR fragment length (base pairs) | | GC content (%) | |
|---|---|---|---|---|---|
| | | Max | Min | Max | Min |
| 10K | Xba | 202 | 1700 | 23.716 | 64.841 |
| 50K | Xba | 200 | 2122 | 22.702 | 69.377 |
| 50K | Hind | 245 | 2270 | 21.912 | 72.299 |
| 250K | Nsp | 100 | 1143 | 17.108 | 68.762 |
| 250K | Sty | 115 | 1093 | 17.162 | 71.556 |

After probe and SNP filtering probe-level normalization of signal intensity and summarization is performed across multiple arrays to reduce experimental noise due for example, to array to array variation, background, or relative variation in the performance of probes interrogating a given SNP. The underlying data normalization methods include (1) intra and inter array quantile normalization, (2) allele-specific cross talk correction and (3) normalization for PCR correction.

In some embodiments median scaling is used. Median scaling uses a linear operation, where the scale factor is based on the median of the median from all arrays. A single array median is computed from the intensity of all probes on the array. Median scaling alone may be used for paired sample analysis. For un-paired analysis quantile normalization is preferred in some embodiments.

Quantile normalization may be used to normalize non-linearities in the data. See, Bolstad, B. M., Irizarry, R. A., et. al., A Comparison of Normalization Methods for High Density Oligonucleotide Array Data Based on Bias and Variance. Bioinformatics, 19(2), pp. 185-93. (2003). Probe-level quantile normalization may be used to eliminate biases introduced by experimental covariates such as scanners, operators and replicates, for example. The sketch distribution against which all samples are quantile normalized may be determined from a set of user selected references. In a preferred embodiment the quantile distribution for each array is interpolated from a subset of the probes sampled across each of the references, for example, approximately 50,000 perfect match probes. Sampling over a subset instead of all available probes facilitates computational efficiency. The sample may be about 0.5%, 1%, 5%, 10% or 25% of the perfect match probes for example. In some embodiments the quantile normalization is performed across all samples in a batch. In other embodiments a subset of reference samples are selected to be used for quantile normalization.

After normalization, allele-specific summarization may be performed for each SNP. Intensity values are summarized for the A and B alleles of each SNP. The allele designation may be based on the alphabetical order of the base represented by the mutation. For example, for a SNP with a sequence AT(G/A)TTT the A allele may be designated as the AT(A)TTT allele and the B allele as the AT(G)TTT allele. A median polish operation may be performed after probe-level normalization, to generate a SNP level, allele specific summarization across all relevant probes. Alternatively, plier in RMA mode may be used for the summarization operation. Both methods take into account sample-level effects arising from chip-to-chip (sample-to-sample) variation and feature-level effects arising from systemic differences in feature intensities due to the hybridization specificity of different probe sequences. For N experiments performed, each SNP has a 2XN summary matrix, corresponding to the A and B alleles.

Figure 6:
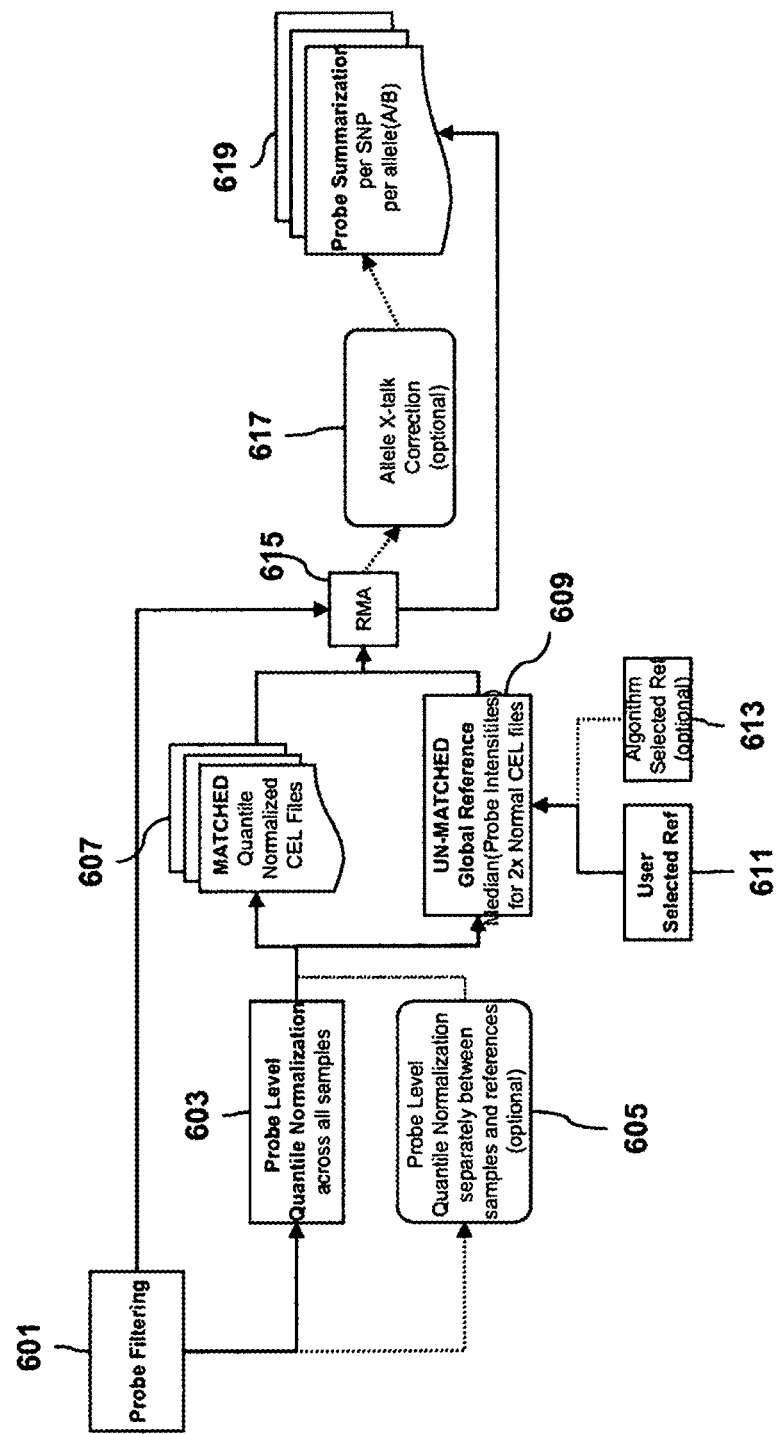
FIG. 6 is a workflow for normalization with global reference generation.

In the un-paired analysis mode a global reference may be computed based on a multi chip-set model. A workflow for generation of a global reference is shown in FIG. 6. Steps 601, 603, 607, 609 and 615 are preformed at the probe level. Step 619 is performed at the SNP level. Steps 605, 617 and 613 are optional. Step 611 represents an input.

A pool of normal female references may be used to generate the reference. Preferably the number of normal controls pooled to form the reference sketch is large enough to generate a stable sketch. At least 2 samples are used and increasing numbers may be used until the quantile distributions converge to within 1 e-4. In a preferred embodiment 25 normal samples are used. All references are preferably quantile normalized to improve the pair-wise correlation of the references. The global reference eliminates the need for selection of references via pair-wise optimization [Nannya Y., et. al, Cancer Res. Vol. 65(14), pp. 6071-79. (2005)].

Figure 7A:
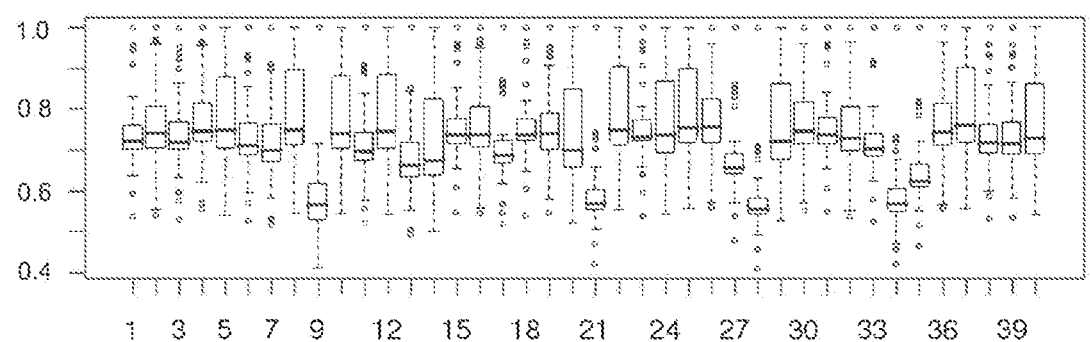
FIG. 7A and FIG. 7B show two box plots of all-versus-all correlation of a global reference pre- and post-quantile normalization respectively.
Figure 7B:
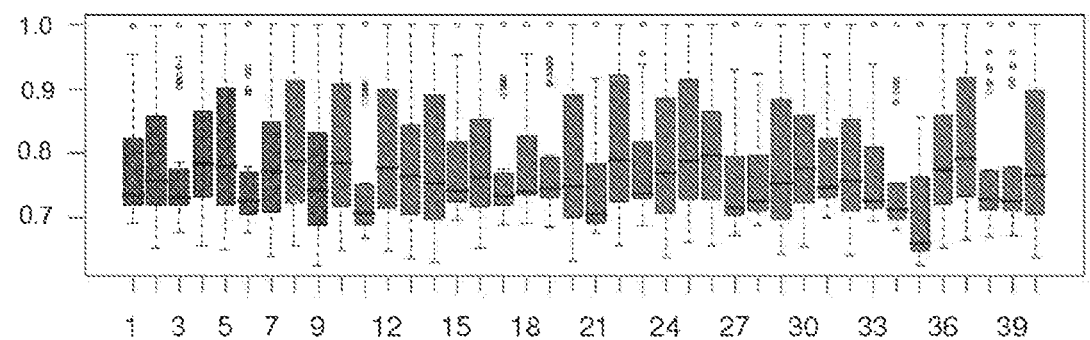

To illustrate the benefits of probe-level quantile normalization an analysis of 40 normal male samples was performed to research the effect of experimental covariates including: operators, scanners, sample replicates and DNA sources. A hierarchical clustering map of the data was generated for an all sample versus all sample Spearman's correlation coefficient for either pre or post quantile normalization. Analysis of the data pre-normalization showed no obvious strong correlations. Analysis of the data post-normalization showed 4 strong correlative blocks corresponding to the samples with the same DNA sources (there were 4 different sources). This demonstrated that quantile normalization is effective at identification of experimental batch artifacts. Two samples with the lowest correlations to the remainder of the samples were also identified and may be sub-optimal. For CN or LOH, a threshold may be set on an all-versus-all correlation measure to filter out sub-optimal samples. FIG. 7 shows box plots of all versus all correlation of the 40 normal male samples pre (FIG. 7A) and post (FIG. 7B) quantile normalization.

Figure 8:
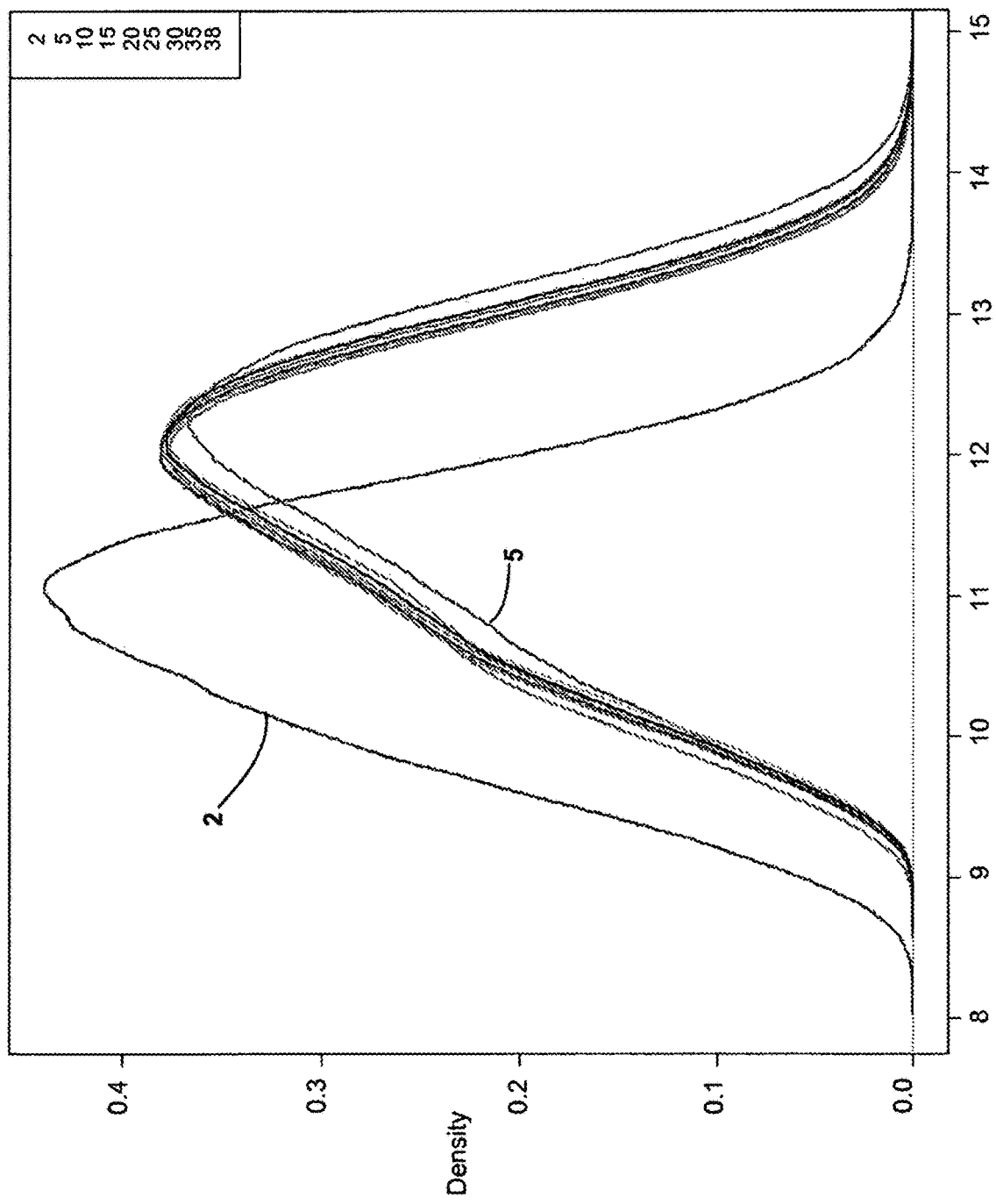
FIG. 8 shows a titration across different number of reference samples used to generate a global reference.

In preferred aspects, the gender of the samples used for reference generation is female. If non-female samples or a mixture of males and females is used this may make it difficult to estimate changes observed in the X chromosome. If CN estimation of the X chromosome is not a concern a pools set of male and female samples may be used to increase the reference sample-size. FIG. 8 shows a titration across different numbers of reference samples. The line for 2 and 5 samples are identified. The lines for 10, 20, 25, 30, 35 and 38 are largely overlapping. In preferred aspects 5 to 10 samples are used to generate a global reference, but more preferably the global reference is generated using about 10 samples, for example, 10-15, 10-30, or 20-40. In some aspects, the references may be ethnically matched to the test sample.

The theory behind the PCR correction is as follows. For the raw CN estimation the relative copy number at the $i^{th}$ SNP between two samples (1 and 2) is estimated based on the $\log_2$ ratio of the normalized signals (S) using Equation 1.

$$\Lambda_i^{1,2} = \log_2\left(\frac{S_i^1}{S_i^2}\right) \text{ for ith SNP}$$

When doing un-paired analysis, the global reference is preferably used. The total copy number (TCN) is a summation of the allele-specific copy number (ASCN) and is referred to as the logSum and can be calculated using Equation 2:

$$TCN = \log_2\left(\frac{S_A}{R_A + R_B} + \frac{S_B}{R_A + R_B}\right)$$

In another embodiment an approximation of the TCN, referred to as the "sumLog" may be obtained using Equation 3:

$$TCN = \log_2\left(\frac{S_A}{R_A}\right) + \log_2\left(\frac{S_B}{R_B}\right)$$

In Equations 2 and 3, S and R refer to the test and reference samples respectively and A and B refer to the alleles. The logSum approach is optimized for variance reduction at the cost of an increased bias offset, the bias is primarily compressed toward the copy nenutral (CN=0) state. The approach provides improvements in discrimination and statistical confidence estimation. The sumLog approach optimizes for bias at the cost of variance.

If PCR amplification has been used, after estimation of raw copy-number, an allelic and SNP-level normalization may be performed to correct for potential artifacts introduced by the PCR process (see, Nannya Y., et. al, Cancer Res., 65(14):6071-79, (2005) and Ishikawa S, et. al, Biochem Biophys Res Commun.,12; 333(4):1309-14 (2005). The relative copy number, $A_i^{1,2}$, for the $i^{th}$ SNP is given by Equation 1 and The different PCR conditions are compensated for by assuming, Equation 5:

$$\Lambda_i^{1,2} = \log_2\left(\frac{S_i^1}{S_i^2}\right) \text{ for ith SNP}$$

-continued $$\Lambda_i^{1,2} = {}^c A_i^{1,2} + p(x)$$

$$p(x) = \sum_{j=1}^{2}(a_j + b_j x_j + c_j x_j^2) \text{ where } j = GC, \text{ fragment length}$$

$$q(x, y)) = (A + bx + b'y + cx^2 + c'y^2) \text{ where } x = GC/y = \text{fragment length}$$

Where ${}^c A_i^{1,2}$ represents the corrected CN and p(x) denotes the PCR amplification kinetics. In the quadratic PCR correction implemented as a linear regression, GC content and length of the PCR fragment that a SNP resides on are the covariates and q(x,y) represents a variant on the implementation of p(x).

Figure 9:
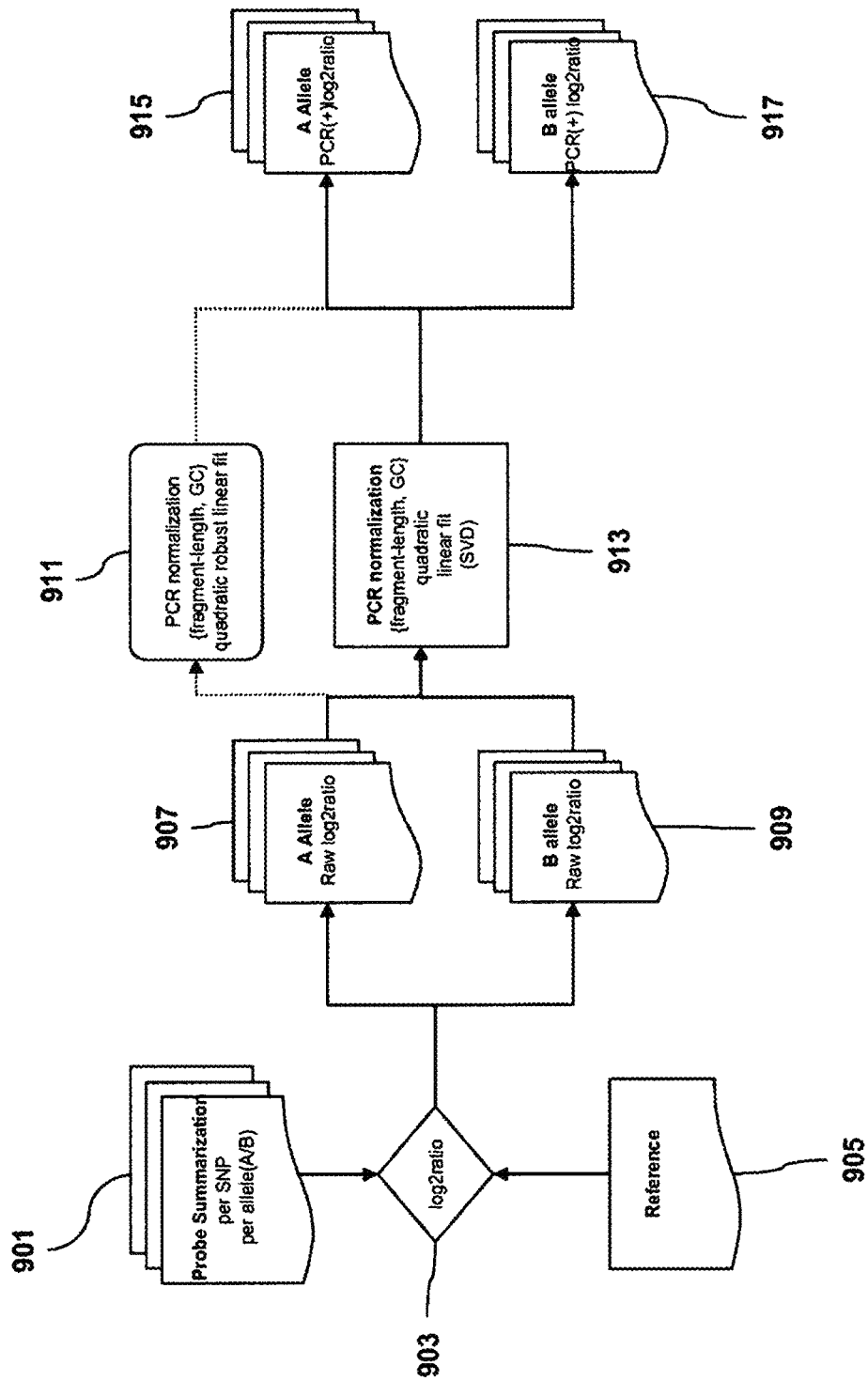
FIG. 9 is a workflow of PCR normalization using covariates GC content and length of PCR fragments.

The theory behind PCR correction generally is to use quadratic correction using the covariates GC content of PCR fragment and length of PCR fragment. The core idea was described in Nannya et al., Cancer Res. 65(14):6071-79 (2005). As implemented in CNATv4.0 the correction {q(x, y)} is implemented via a singular value decomposition fit and the normalization is performed using a linear model fit that combines the two covariates in a single equation represented above by q(x,y). In Nannya et al. the method was implemented in two steps as represented above by p(x). In another aspect a non-linear regression may be performed, which may facilitate fitting the tails of the distribution. FIG. 9 shows a workflow of an implementation of the PCR correction. The analysis are SNP level and 911 is optional.

Figure 10:
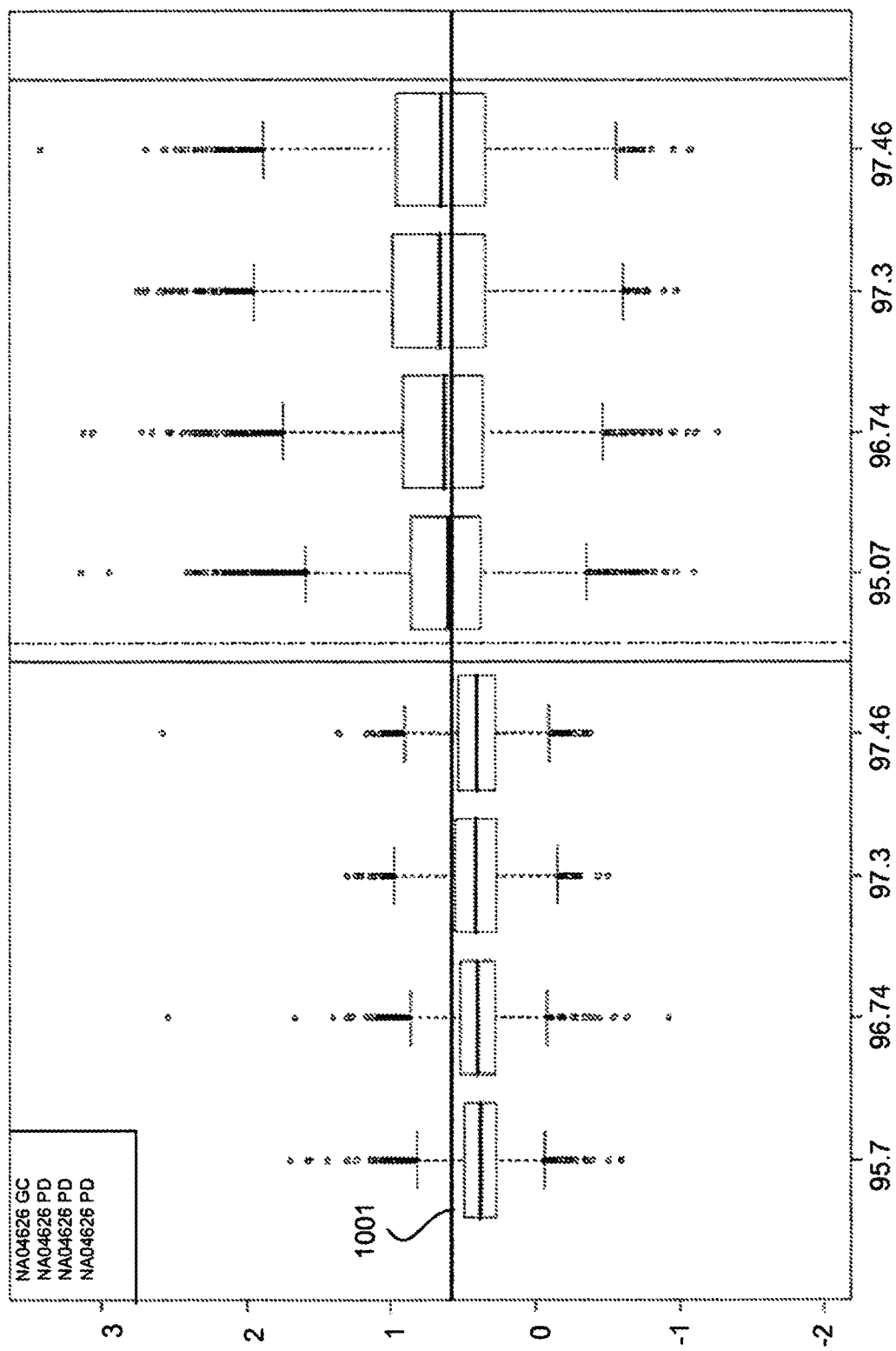
FIG. 10 shows the effect of PCR correction on samples with known copy number.

FIG. 10 shows the effect of PCR correction on samples with 3 copies of the X chromosome. These box plots represent the distribution of CN estimates in chromsome X, in 4 different samples. The datasets are also part of a 3X titration study (samples spiked with 3 copies of chromosome X). This implies the data has experimentally spiked in 3 copies of chromosome X. The plots on the left hand side represent the datasets pre PCR-normalization and the ones on the right represent the same datasets post PCR-normalization. The x-axis corresponds to the array call-rates and the y-axis to the CN estimate in log2ratio space. Since this is a 3X titration study, ideally all SNPs on chromosome X should be present in the 3x state, which is equal to log2(3/2)~0.58. The line [1001] reflects the expected value of 0.58 and serves as a 'line of truth'. As evident from the plots, not all SNPs corroborate the 3X state, but there exists distribution of CN states with a non-zero variance. In case of the datasets where no PCR normalization has been applied the distribution is NOT centered about the 'line of truth' but post PCR-normalization the data gets more centered about the 'line of truth' indicating the efficacy of the PCR normalization. Similar improvement was observed for sets of 4X and 5X data.

A portion of the compression may be the result of an aberration resulting from cross hybridization to the non-target allele. For example, if the A allele is amplified, the signal associated with the A allele perfect match probe may approach saturation and A allele sample may increasingly hybridize to the B allele perfect match probe. This issue of the accuracy versus variance described before may be due to allele cross-talk as discussed here. Or simply the compression in the estimate of copy number arises due to the allele-crosstalk. In preferred aspects some type of normalization is used to adjust for this effect which is not addressed by the PCR normalization correction. All data shown in this section is for SNPs exclusively on chromosome X, unless mentioned otherwise.

Figure 11:
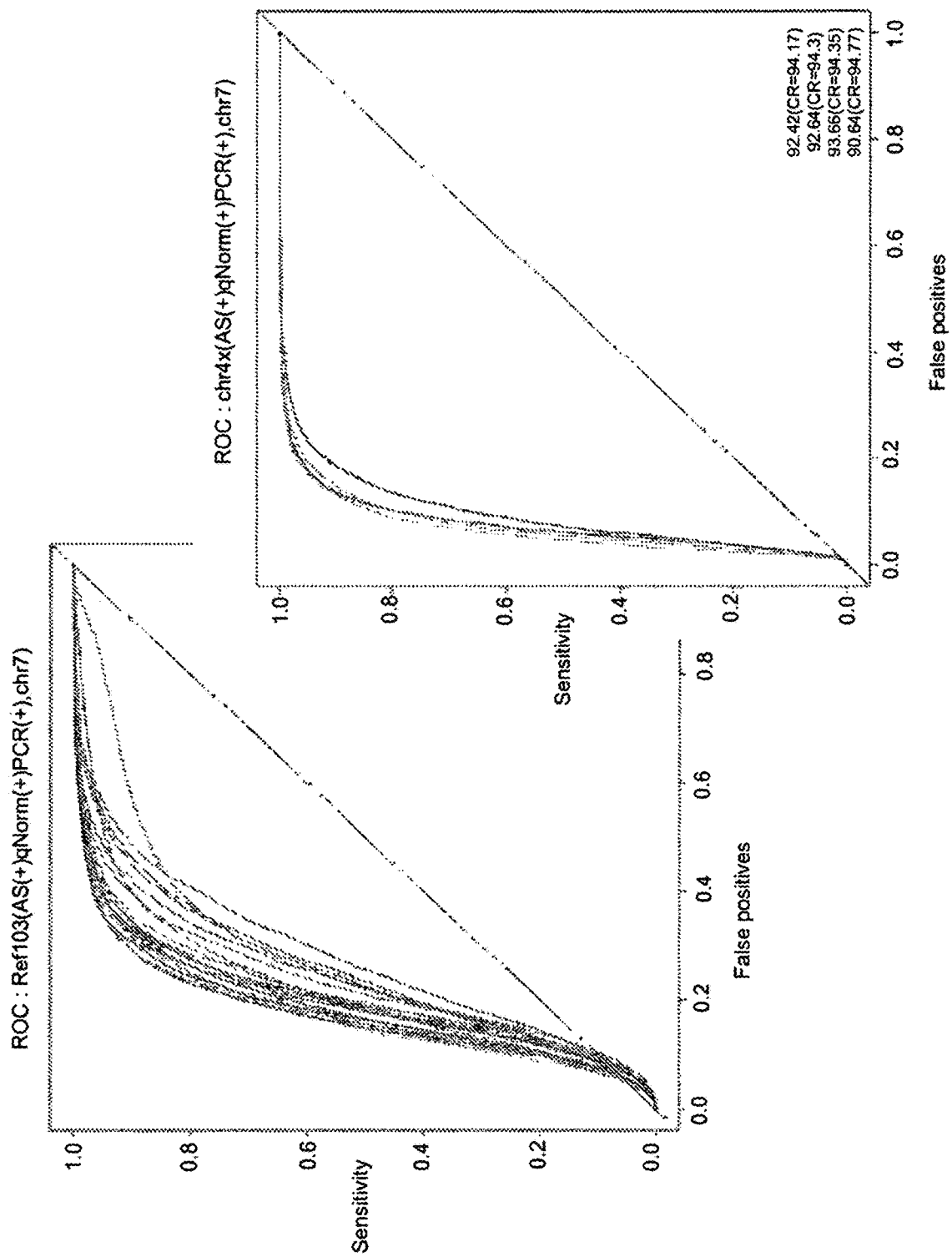
FIG. 11 shows ROC curves for 1X to 4X titration data after PCR normalization.

FIG. 11 shows ROC curves for the 1X to 4X titration data. The data is shown for the post PCR normalization status. In this rendering of the ROC curves, the positive regions are determined from Chr 7 which is expected to be in a diploid state and the negative regions are determined from Chr X which is either in the haploid or multiploid (4X) state.

Figure 12:
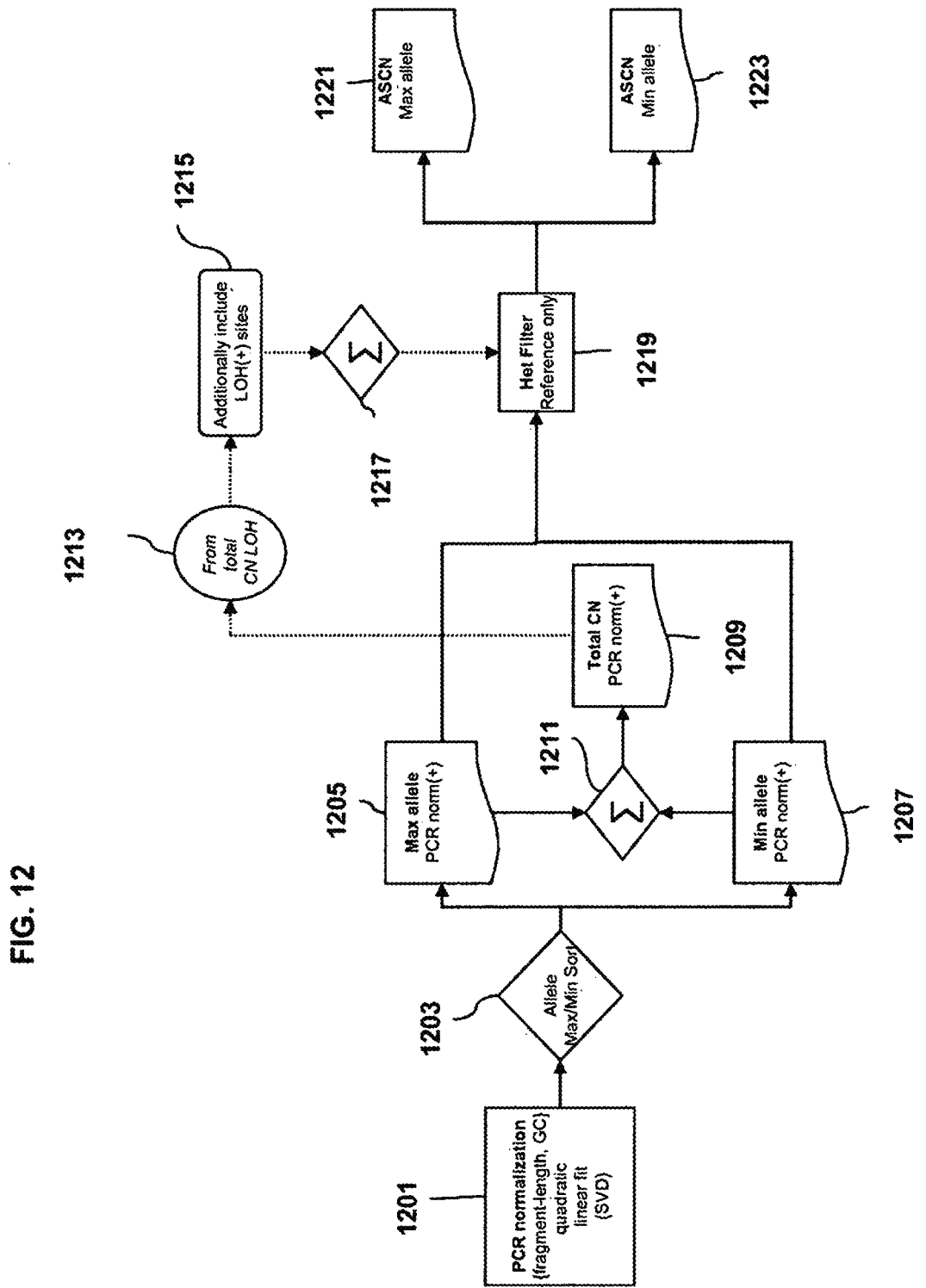
FIG. 12 shows a workflow of total copy number versus allele specific copy number.

FIG. 12 shows a workflow of total copy number versus allele specific copy number analysis. Optional steps are represented by 1213, 1215 and 1217. A workflow for the generation of the estimate of total copy number is shown. The analysis is done at the SNP level. Optional steps include determining LOH from total CN.

Two different estimates of the TCN are shown below. The first is the equation for logSum estimating and the second is the equation for sumLog estimating.

$$TCN = \log_2\left(\frac{S_A}{R_A + R_B} + \frac{S_B}{R_A + R_B}\right)$$

$$TCN = \log_2\left(\frac{S_A}{R_A}\right) + \log_2\left(\frac{S_B}{R_B}\right)$$

Where $R_A$ is the copy number of the allele A of the reference, $R_B$ is the copy number of the allele B of the reference, $S_A$ is the copy number of the allele A of the sample being tested and $S_B$ is the copy number of the allele B of the sample being tested. The logSum estimate for the TCN is the conventional one where $R_A + R_B = 2$ since in the diploid sample one copy of the chromosome is paternal and the other is maternal. The sumLog estimate is an approximation of the logSum estimate. The logSum equation is appropriate if there is no or minimal cross-talk between A and B alleles, that is they are independent for homozygous calls. If there is cross-talk, the signal measured in alleles A and B have a cross-talk or contamination component from the opposite allele.

Figure 13:
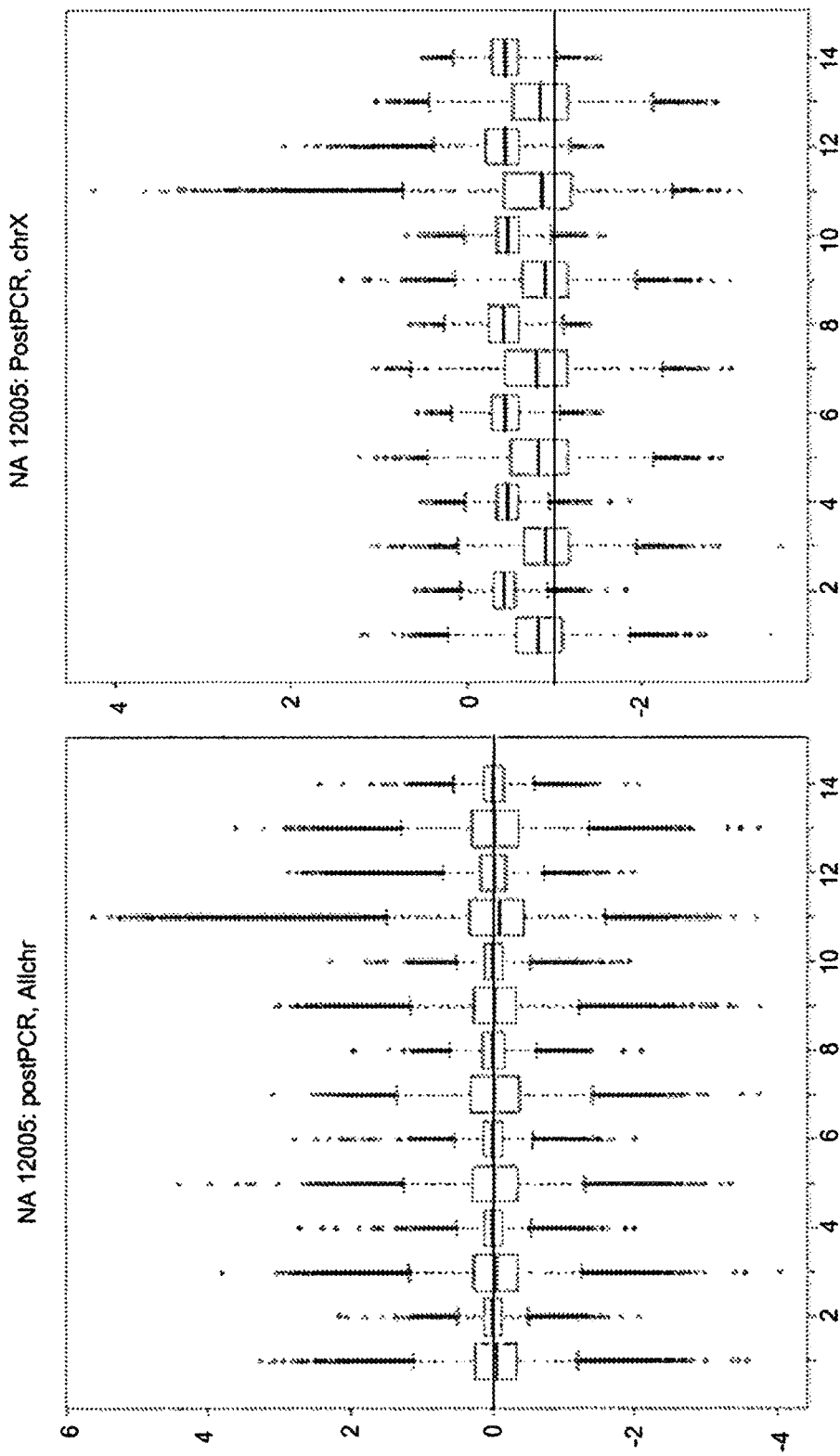
FIG. 13 shows an analysis of data for 7 samples using both sumLog and logSum approaches for all chromosomes (13A) or the X chromosome (13B)

FIG. 13 shows the data for 7 samples and 12 references. FIG. 13A shows all chromosomes and FIG. 13B shows chromosome X. Odd numbered data is sumLog and even is logSum. The data is post PCR correction, chr 1x data. The data is paired, for example, 1 on the X axis is sample 1 with sumLog estimation applied and 2 on the X axis is sample 1 with logSum estimation applied. The line at 0 in A and −1 in B shows the expected value. Where all chromosomes are analyzed en-masse (FIG. 13A) which is primarily diploid in the normal male samples, both TCN estimates yield similar results with the logSum estimate having a slightly tighter variance. When the analysis is specifically the chromosome X data (FIG. 13B), it becomes apparent that for the logSum estimate the accuracy of CN estimate is sacrificed (even numbers on the X axis) although a tighter variance is observed. The results suggest that copy number compression is being observed. That is, the logSum estimate gives a higher CN estimate than the truth in case of a deletion.

Figure 14:
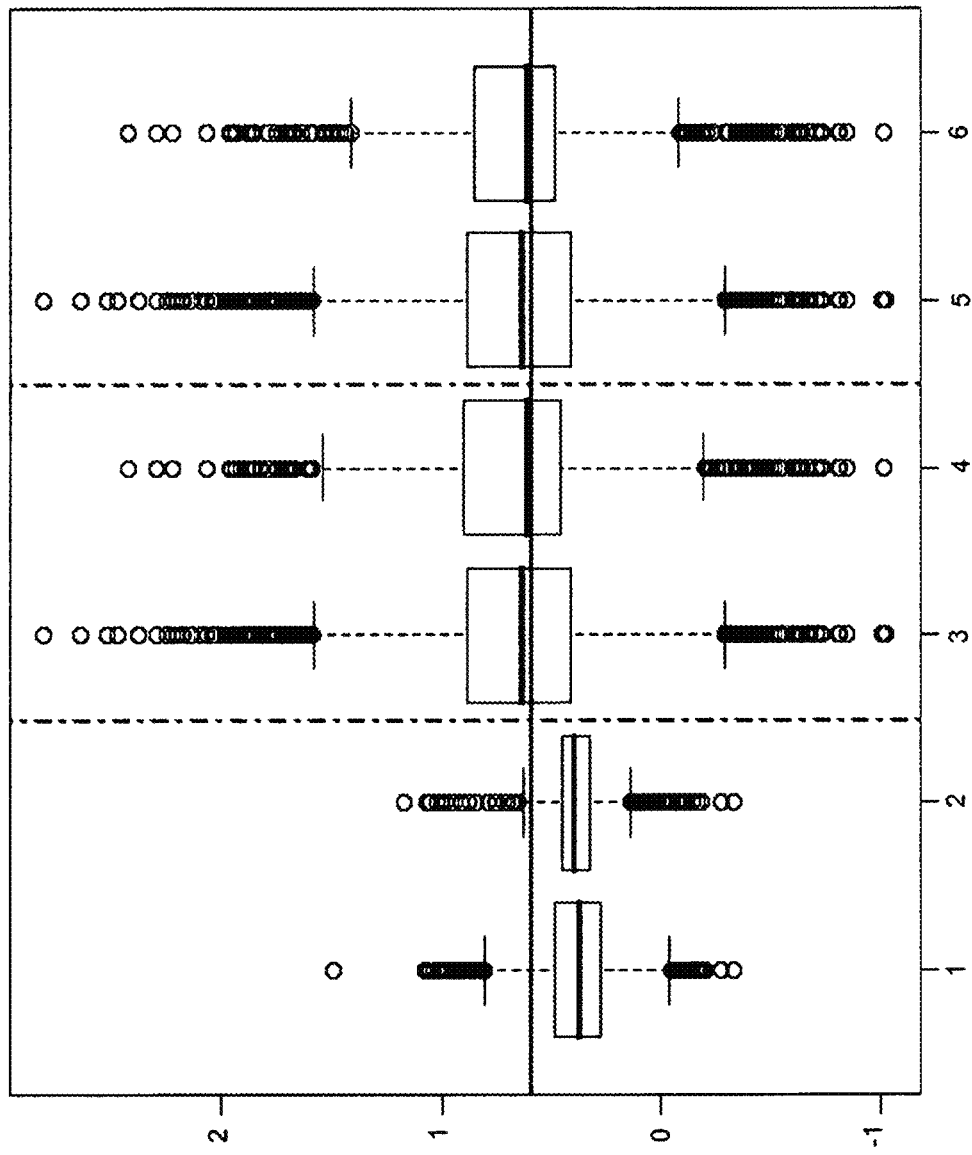
FIG. 14 shows logSum compared to sumLog for a 3X dataset.

The effect is also observed in the 3X datasets (FIG. 14). Plots 1, 3 and 5 are logSum and plots 2, 4 and 6 are sumLog. The expected value is shown by the horizontal line at ~0.58 (log2(3/3)~0.58). Again the logSum estimate gives a lower CN estimate than expected for the level of amplification. The data is shown for a single sample compared to 27 reference samples. The data is post HMM and the HMM parameters are sigma=10% equal priors (1 and 2), sigma=10% transition-matrix decay: 1e6 (3 and 4) and sigma=10 and 20% (state 2) EM optimized.

Figure 15A:
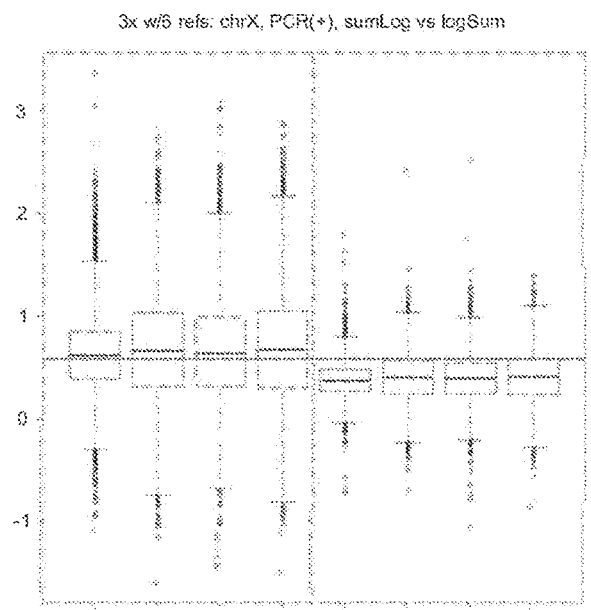
FIG. 15A illustrates a plot of sumLog compared to logSum estimates for a potentially mixed sample.
Figure 15B:
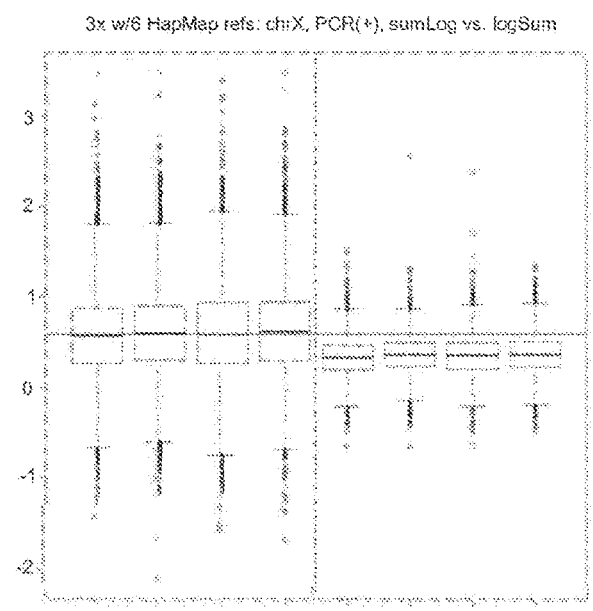
FIG. 15B illustrates a plot of sumLog compared to logSum estimates for a reference of HapMap samples.

The consequence of mixing artifacts in the reference is illustrated by the data represented in FIG. 15. One possible explanation for the variance versus accuracy issue is that the normal samples used to create the reference distribution might not be completely normal tissue and might have some mixture component from the tumor samples. The data in FIG. 15A is for the reference created from a potentially mixed sample. The data in FIG. 15B is from a reference constructed from samples that are known to be normal. While the tissue-types of the references are varied the number of cel files used to create the global reference are held constant (n=6) in each case. In each plot, 4 samples are shown with sumLog estimates to the left of the dashed vertical line and logSum estimates to the right of the line. The vertical blue line represents the 'line of truth' for the 3x sample and is located at log2(3/2)~0.58. This data demonstrates that mixing in sample tissue is not likely to cause the accuracy versus variance bias. Similar analysis was performed to determine if the number of cel files used to generate the reference has an effect on accuracy versus variance, but no obvious consequence was observed.

To investigate if the variance versus accuracy effect results from mixture of tumor tissue in the normal samples used to create the reference distribution, well characterized normal HapMap samples were compared to "normal" samples that have the potential for some mixing of tumor and normal tissue. The data in FIG. 15A is reference created from a potentially mixed sample mode while FIG. 15B shows data for a reference constructed from HapMap samples, where the samples were known to be normal and the experiments show the least degree of technical issues. While the tissue-types of the references are varied, the number of .cel files used to create the global reference are held constant (n=6) in each case. Again in each plot, 4 samples are shown with sumLog estimates on the left (left of the dashed line) and logSum estimates to the right of the dashed line. The horizontal line between 0 and 1 represents the 'line of truth' for the 3x sample and is therefore at $\log_2(3/20) \approx 0.58$. This data demonstrates that mixing in sample tissue is not the cause of the accuracy versus bias effect.

Figure 16A:
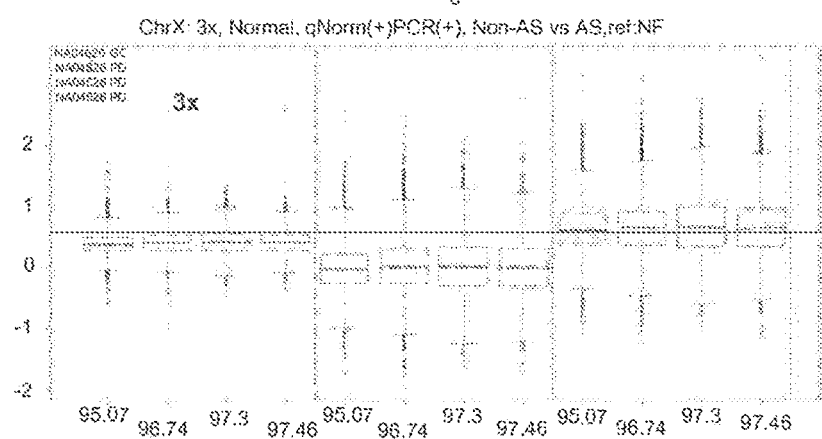
FIGS. 16A, 16B, and 16C illustrate the effect of PCR correction for 3X, 4X, and 5X copy number amplifications, respectively.
Figure 16B:
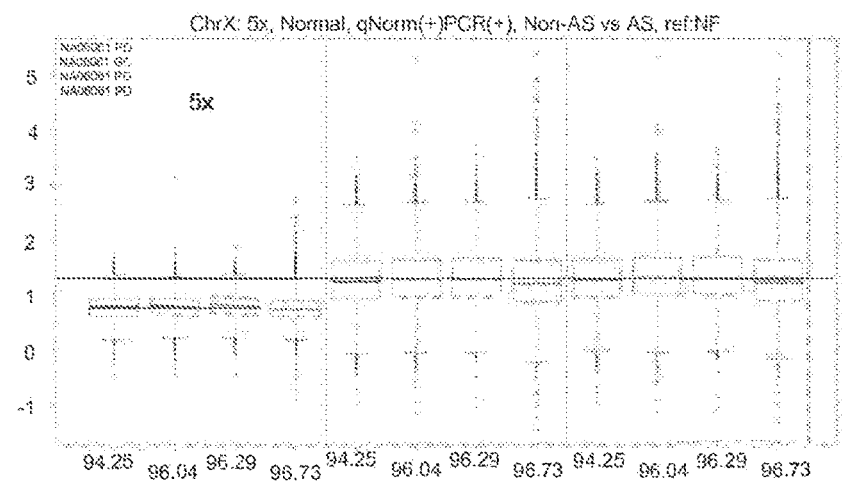
Figure 16C:
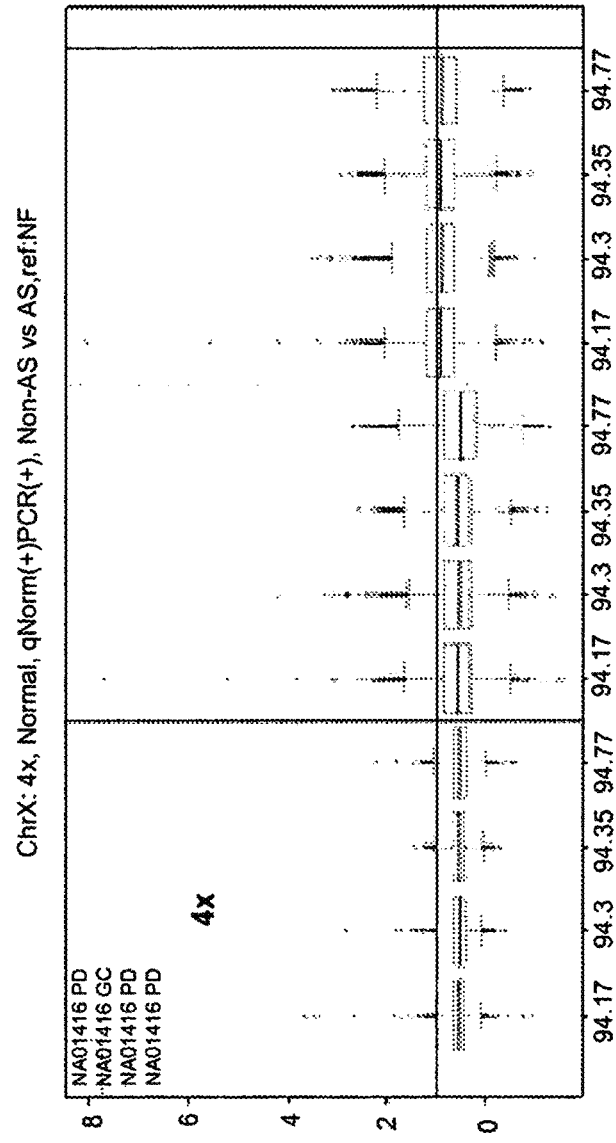

The effect of PCR correction is illustrated by the data in FIGS. 16A, 16B, and 16C. Each panel is divided into left, center and right panels. The left panels are pre-PCR correction, the center is logSum and the right is sumLog. FIG. 16A is for 3X, FIG. 16B 5X and FIG. 16C is 4X. Compression artifacts are observed in all cases of chromosomal copy number amplifications, 3, 4, or 5 copy gains, but it is more dramatic without PCR correction.

Figure 17A:
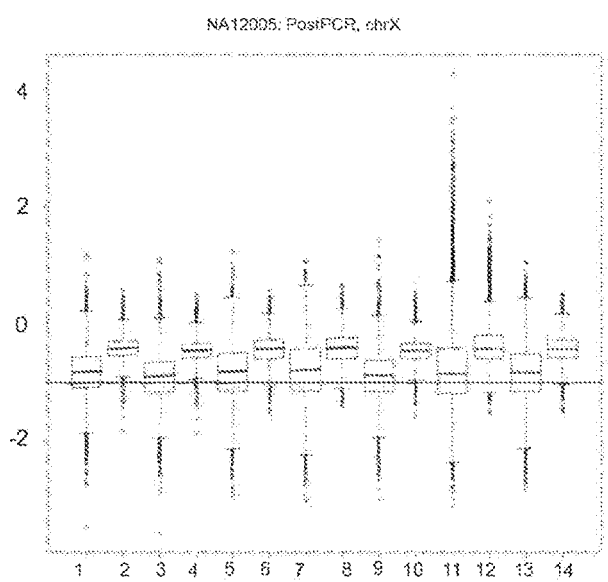
FIG. 17A illustrates the effect of PCR correction on 1X data.
Figure 17B:
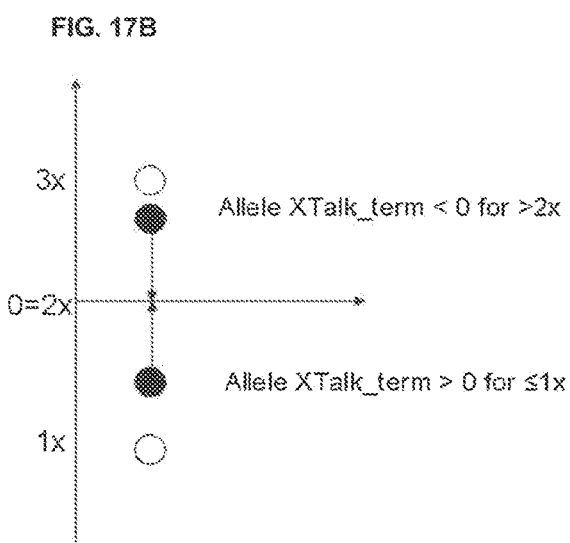
FIG. 17B illustrates the nature of the compression artifact.

The effect of PCR correction on 1x data is shown in FIG. 17. The data is for 1X in chromosome X, or 1 copy loss. The logSum generates an estimate of CN that is higher than expected (shown by horizontal line in FIG. 17A). FIG. 17B illustrates the nature of the compression artifact. The white circles represent the expected value or the "truth" and the black circles represent the outcome following compression. As shown above, in case of the amplifications, the compression artifact lowers the estimate of CN (that is it moves the estimate of the CN closer to that of the Copy neutral state, $\log_2(2/2)=0$). In case of the deletions, the compression artifact raises the estimate of CN (that is it moves the estimate of the CN closer to that of the copy neutral state, $\log_2(2/2)=0$). As a result, in case of amplifications, the allele cross-talk term is less than 0 and in case of deletions the allele cross-talk term is greater than 0.

The theory behind allele cross talk correction is as follows. The following equation for the estimate of total coy number (TCN) is appropriate if there exists no cross-talk between the A and B alleles, that is they are independent for homozygous calls:

$$TCN = \log_2\left(\frac{S_A}{R_A + R_B} + \frac{S_B}{R_A + R_B}\right)$$

where S is sample signal and R is reference signal for alleles A and B. Due to cross-talk, the signal measured in alleles A and B have a cross-talk or contamination component from the opposite allele. The cross-talk parameters are modeled by $\alpha$ and $\beta$. Hence $\hat{S}_A = \alpha S_A + \beta S_B$, $\hat{S}_B = \alpha S_B + \beta S_A$ $$\log_2\left(\frac{\hat{S}_A}{R_A + R_B} + \frac{\hat{S}_B}{R_A + R_B}\right) =$$

$$\log_2\left(\frac{\hat{S}_A}{R_A}\right) + \log_2\left(\frac{\hat{S}_B}{R_B}\right) + \log_2\left(\frac{(\hat{S}_A + \hat{S}_B)/\hat{S}_A \times \hat{S}_B}{(R_A + R_B)/R_A \times R_B}\right) =$$

$$\log_2\left(\frac{\hat{S}_A}{R_A}\right) + \log_2\left(\frac{\hat{S}_B}{R_B}\right) + XTalk - \text{term}$$

$$XTalk - \text{term} = \log_2\left(\frac{(\hat{S}_A + \hat{S}_B)/\hat{S}_A \times \hat{S}_B}{(R_A + R_B)/R_A \times R_B}\right) =$$

$$\log_2((\hat{S}_A + \hat{S}_B)/\hat{S}_A \times \hat{S}_B) - \log_2((R_A + R_B)/R_A \times R_B) =$$

$$k' - k = \log_2[(\alpha + \beta)(S_A + S_B)] - \log_2[(\alpha S_A + \beta S_B)(\beta S_A + \alpha S_B)] - k$$

Figure 18:
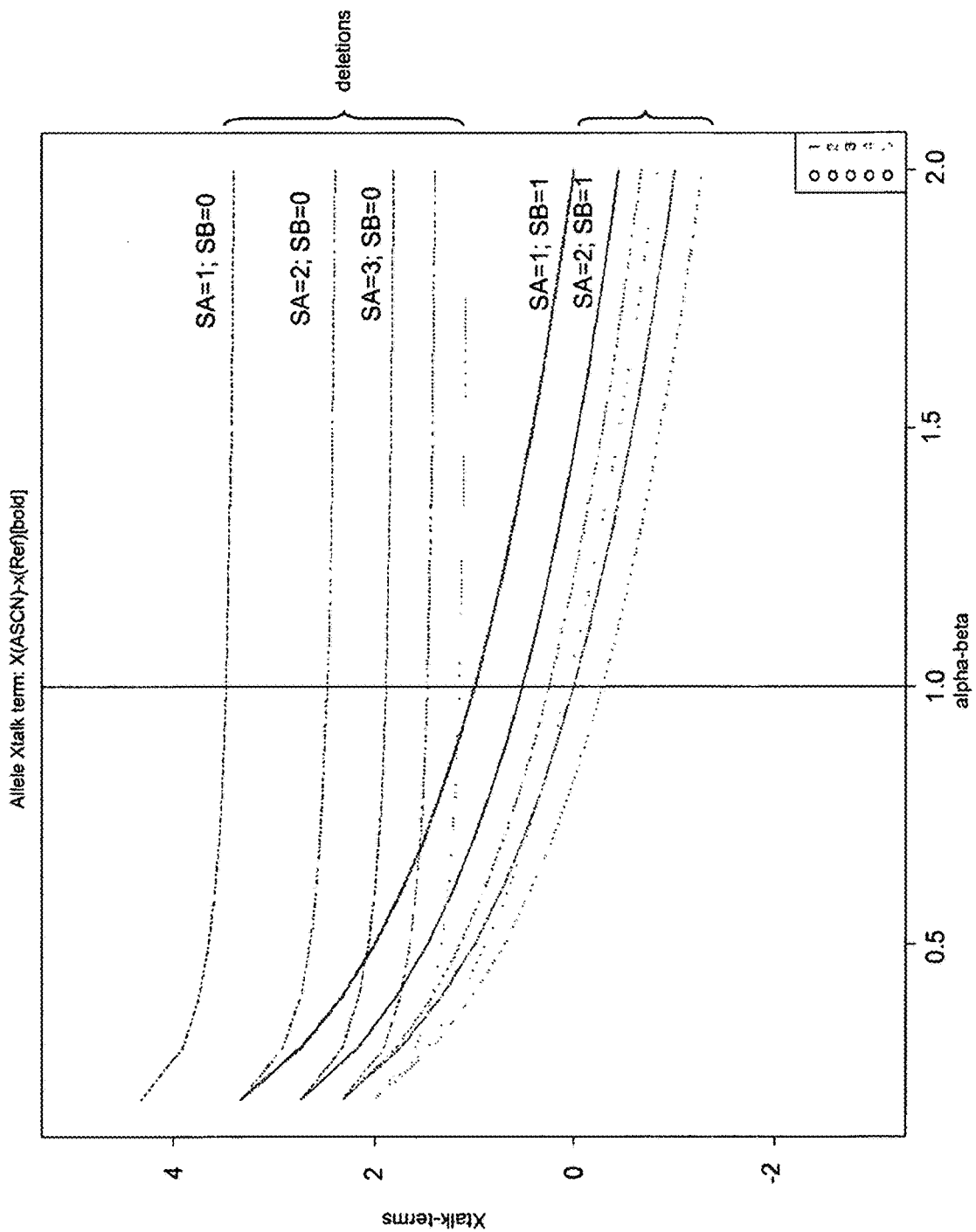
FIG. 18 shows increased cross talk for deletion regions.
Figure 19:
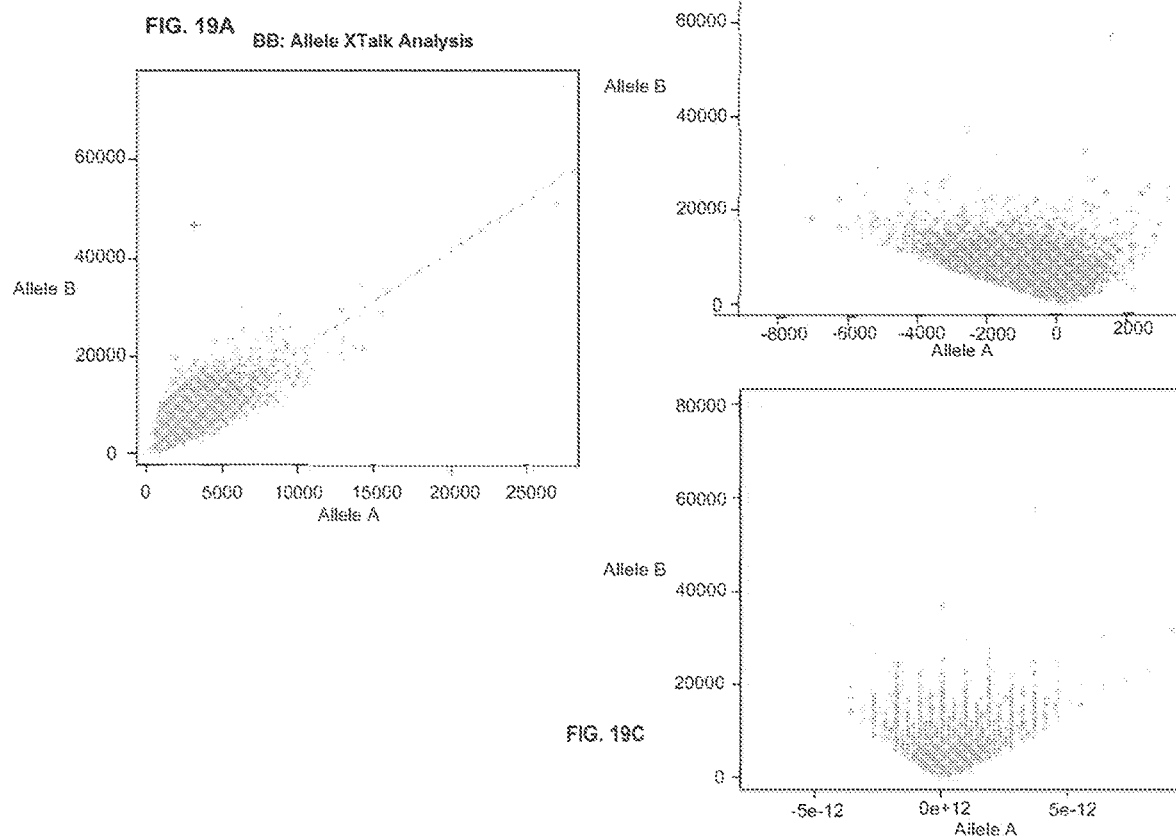
FIG. 19A illustrates an allele cross-talk analysis.
FIG. 19B shows the results of global rotation transformation of the data in FIG. 19A.
FIG. 19C illustrates the results of local rotation transformation of the data in FIG. 19A.

For $R_A = R_B$ if $\alpha + \beta = 1 \rightarrow k = 1$ if $\alpha + \beta \geq 1 (\alpha > \beta) \rightarrow k < 1$ For $2x: k' \rightarrow k \therefore \text{XTalk\_term} \rightarrow 0$ For $1x: k' > k \therefore \text{XTalk\_term} > 0$ For $> 2x: k' < k \therefore \text{XTalk\_term} < 0$ if $\alpha + \beta < 1 (\alpha > \beta) \rightarrow k > 1$ For $2x: k' \rightarrow k \therefore \text{XTalk\_term} \rightarrow 0$ For $1x: k' > k \therefore \text{XTalk\_term} > 0$ For $> 2x: k' < k \therefore \text{XTalk\_term} < 0$ FIG. 18 shows the increase in cross-talk for deletion cases as a function of alpha and beta where alpha and beta refer to the degree of cross-talk. Rotation transformation may be used to correct for allele cross-talk. The correction may be effected as a correction based on a global transformation or a correction based on a local transformation. For 1X SA=1, SB=0, for 2X SA=1, SB=1 or SA=2, SB=0, for 3X SA=2, SB=1 or SA=3, SB=0, for 4X SA=2, SB=2 or SA=3, SB=1 or SA=4, SB=0, and for 5X SA=3, SB=2 or SA=4, SB=1 or SA=5, SB=0. When SB=0 denotes a deletion. FIG. 19 shows the results of global (FIG. 19B) or local (FIG. 19C) rotation transformation of the data shown in FIG. 19A.

Figure 20:
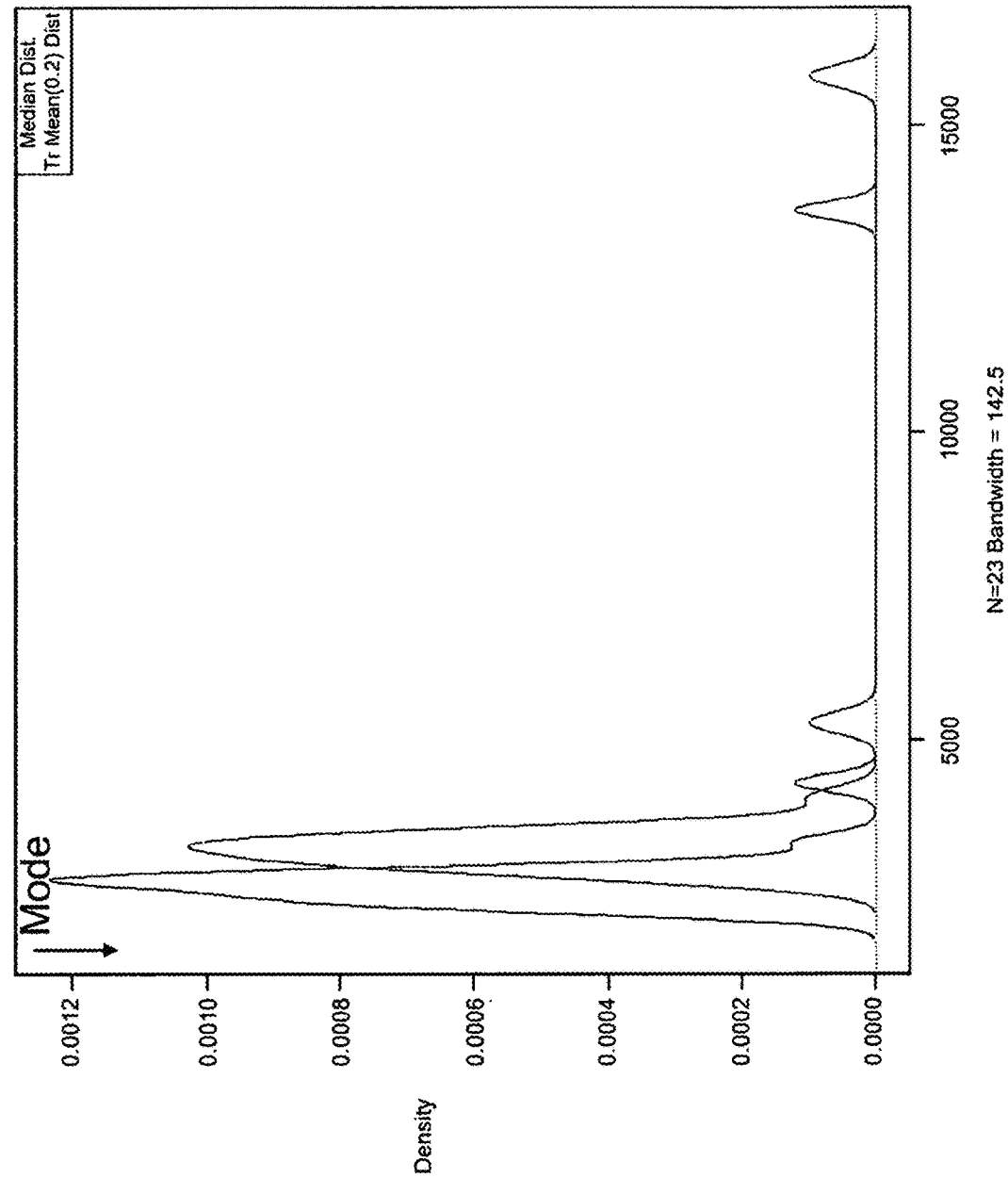
FIG. 20 shows the dynamic estimation of the Gaussian smoothing bandwidth.

Cross talk term equations are as follows:

$\hat{S}_A = (\alpha \times S_A + \beta \times S_B)$ $\hat{S}_B = (\beta \times S_A + \alpha \times S_B)$ where $\alpha > \beta$ $t1 = \log_2((\alpha + \beta)(S_A + S_B))$ $t2 = \log_2((\alpha S_A + \beta S_B) \times (\beta S_A + \alpha S_B))$ $ASCN_{XTalk} - REF_{XTalk} = k' = t1 - t2$ FIG. 20 shows the dynamic estimation of the Gaussian smoothing bandwidth. The estimation of the Gaussian bandwidth is 14K, which is a conservative estimate. The trimmed mean (0.2) chromosomal ISD distribution. D=density distribution (T_ISD$_1$ ... T_ISD$_x$), μ=Mode(D), σ=Stdev(d) and BW=μ+1.5σ. Where ISD is the inter-SNP distance, ISD$_1$+ [10, 40, 500, 400, 20000]T_ISD$_1$=TrMean(0.2)(ISD$_1$)=313. MD_ISD$_1$=Median(ISD$_1$)=400, ME_ISD$_1$= Mean(ISD$_1$)=4190, and Default BW=14890. The X axis shows default bandwidth estimation and the Y axis is density.

The data shown in FIG. 16 demonstrate that the compression artifact may be observed in all cases of chromosomal copy number amplifications. That is in case of 3, 4 or 5 copy gains of the X chromosome, the logSum generates an estimate of the CN which is lower than that of the truth (blue horizontal line). FIG. 17 shows that the compression artifact is observed in chromosomal copy number deletions as well (data shown for 1X in chromosome X). That is in the case of 1 copy loss, the logSum generates an estimate of the CN which is higher than that of the truth (red horizontal line between 0 and −2). The cartoon in FIG. 17B demonstrates the compression artifact schematically. The green circles represent the "truth" the circles in red represent the outcome following the compression. As shown in the results in the prior sections, in case of the amplifications, the compression artifact decreases the estimate of CN (that is moves the estimate of the CN closer to that of the Copy neutral state, log2(2/2)=0). In case of the deletions, the compression artifact raises the estimate of CN (that is moves the estimate of the CN closer to that of the Copy neutral state, log2(2/2)=0). Therefore in case of amplifications, the allele cross-talk term is less than 0 and in case of deletions the allele-cross-talk term is greater than 0. FIG. 18 is a plot showing increase in allele cross-talk term for deletion cases (notation in red) as a function of alpha & beta where alpha and beta from the prior slides refer to the degree of cross-talk. FIG. 19 demonstrates the rotation transformation that may be implemented to correct for allele cross-talk.

The correction can be effected in two ways (1) A correction based on a global transformation or (2) Correction based on a local transformation.

FIG. 20 describes the dynamic estimation of the gaussian smoothing bandwidth. The estimation of the gaussian bandwidth=14K, a very conservative one.

Figure 21:
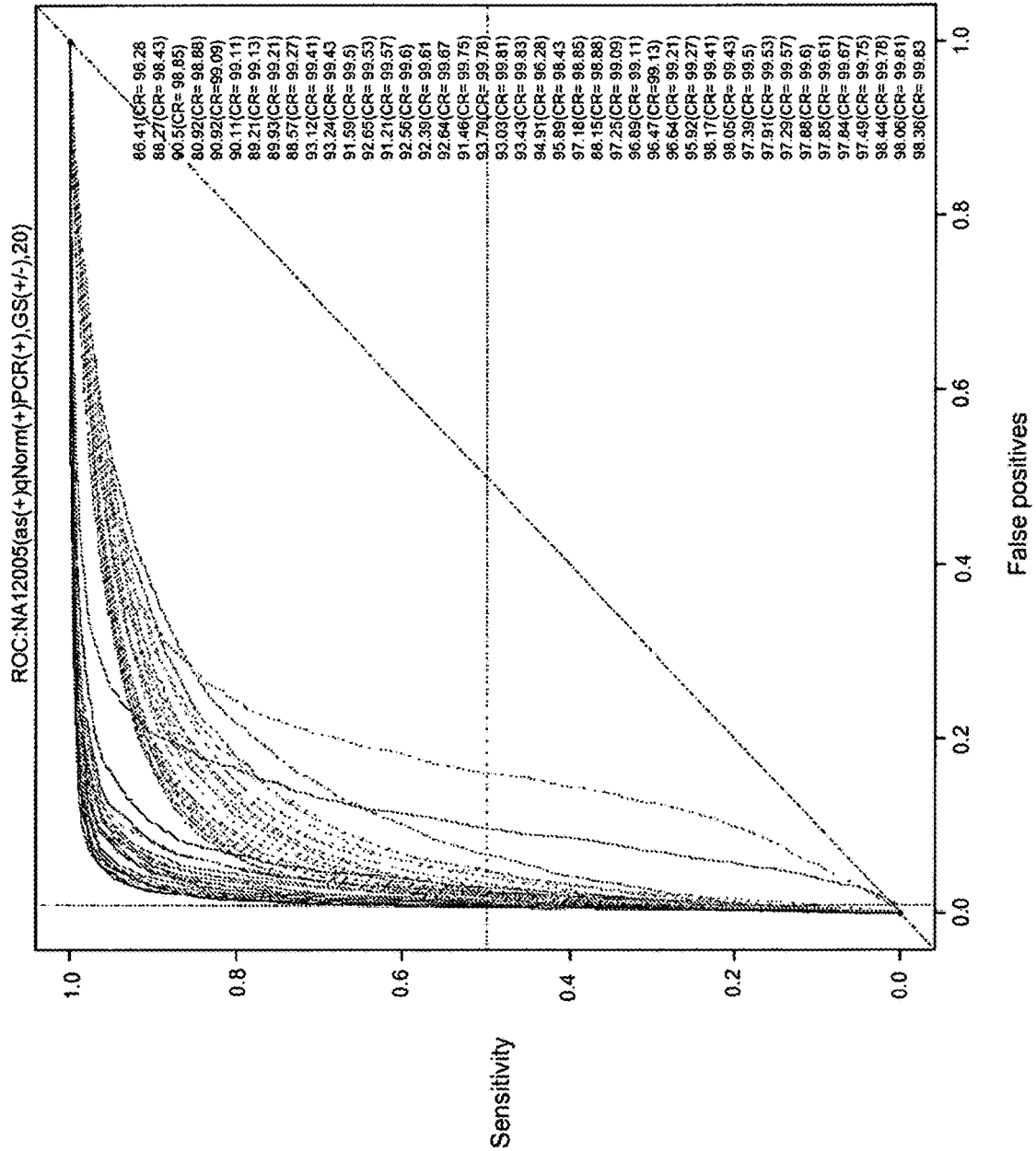
FIG. 21 ROC curves are shown post Gaussian smoothing (solid curves) dashed curves refer to data that has undergone PCR normalization but no Gaussian smoothing.

FIG. 21 ROC curves are shown post gaussian smoothing (solid curves); dashed curves refer to data that has undergone PCR normalization but no gaussian smoothing.

Figure 22:
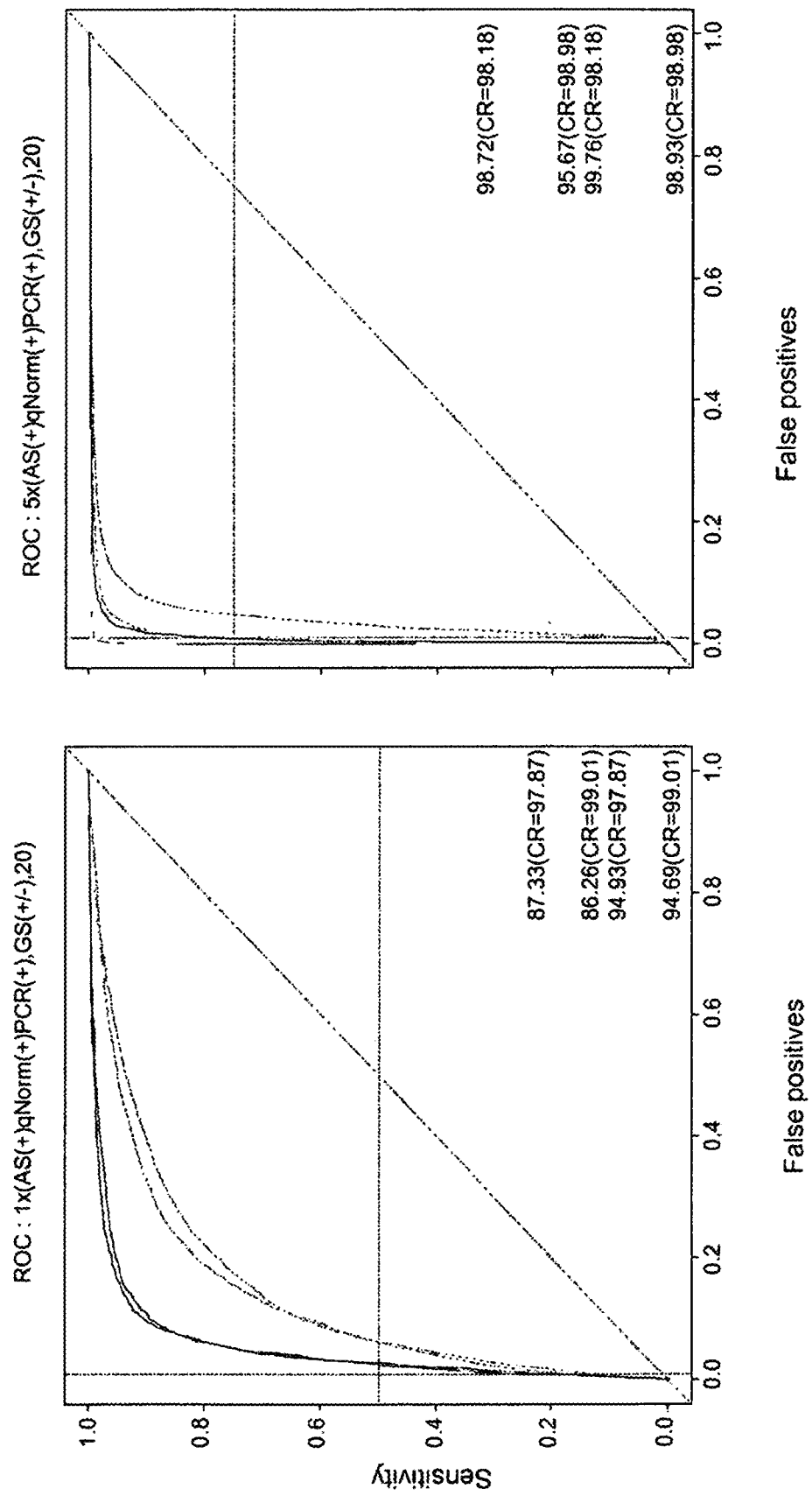
FIG. 22 shows that a 1x to 5x improvement in sensitivity at 1% false positive rate may be obtained following Gaussian smoothing (bandwidth~14K.).
Figure 26:
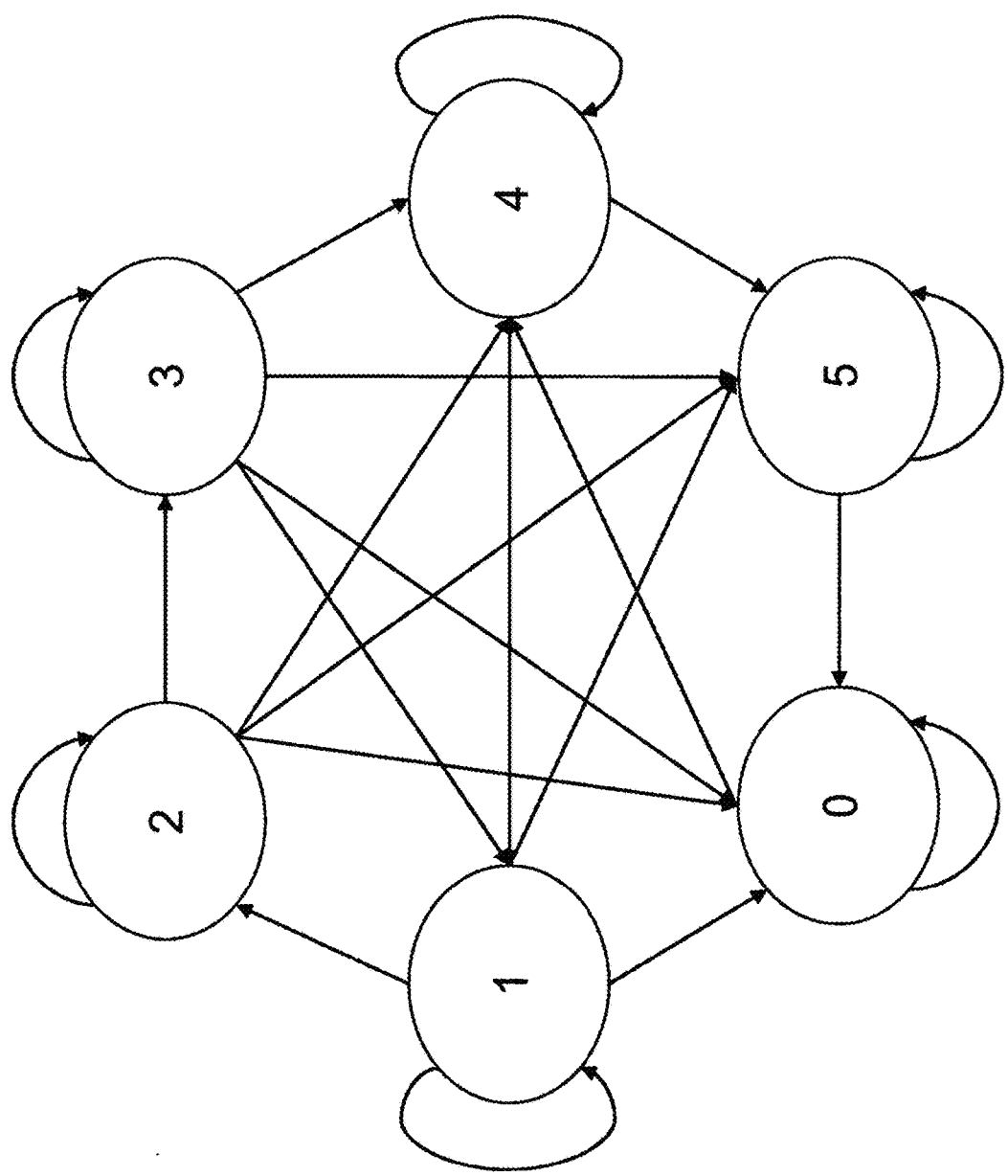
FIG. 26 shows an ergodic model with 6 states.

FIG. 22 Generally 1x-5x fold improvement in sensitivity at 1% false positive rate is obtained following gaussian smoothing—even a very conservative one with bandwidth~14K FIG. 2625 shows the four possible approaches where HMM may be applied: CN Matched HMM, CN un-matched HMM, LOH matched HMM, LOH un-matched HMM. FIG. 26 shows an all-state to all-state transition model where any given state can transition to any other state. In preferred aspects one of two methods is used to set the number of states: (1) Hardwiring of a 5 state model or (2) A dynamic determination of the number of optimal states based on the dataset. This uses the optimization methodologies via the Akaike Information Criteria (AIC) and Bayesian Information Criteria (BIC).

The model shown in FIG. 26 is an Ergodic Model with all state to all state transitions permitted. The components are observations (0), states (true underlying) (N) and probabilities. Probabilities can be divided into prior (π), transition (A) and emission (B). The model: λ=(A, B, π). O={0$_1$, 0$_1$, 0$_3$, 0$_5$, 0$_2$, ... 0$_n$} for 1, 2, 3, 4, 5, ... d. Evaluate the probability of the observation sequence given the model λ. The transition probability is the probability of moving from a first state to another state. Each state has its own emission probabilities which model features of the state.

In preferred aspects the observations for copy number are the Log$_2$ ratios of normalized signals and for LOH the observation is genotype. The states or N for copy number may be, for example, State 0 is homozygous deletion (log$_2$(0.5/2)), state 1 is heterozygous deletion (log$_2$(1/2)), state 2 is copy neutral (log$_2$(2/2)), state 3 is single copy gain (log$_2$(3/2)), state 4 is amplification (log$_2$(≥4/2)), but this may be varied. For LOH a 2 state model may be used with state 0 being LOH and state 1 being normal or retention. All state to all state transitions may be permitted. For matched tumor and normal samples LOH=AB in reference and AA or BB in the tumor sample. Normal or retention=AB in reference and AB in tumor sample. For unmatched samples, the probability of being in LOH or retention state may be determined using the SNP heterogeneity rate across a reference pool and the genotyping error rate.

Figure 27:
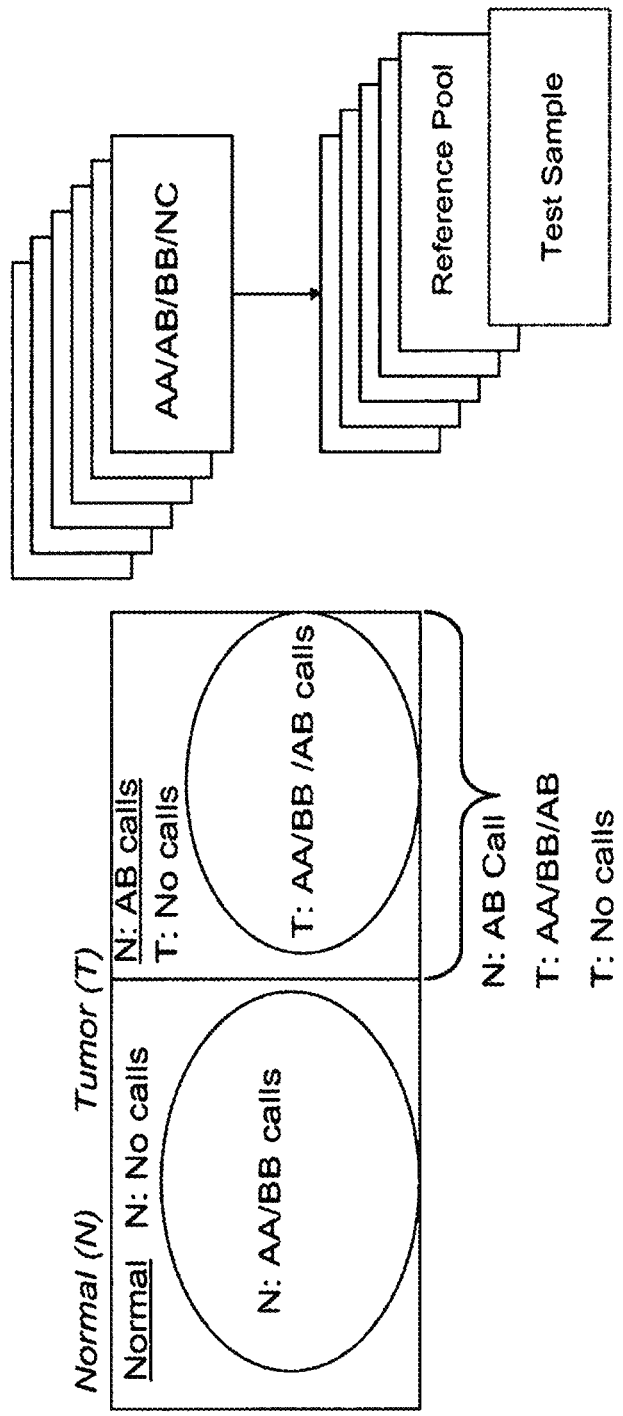
FIG. 27 is a schematic of a set up of the analysis for matched tumor-normal tissue pairs versus un-matched samples.

FIG. 27 shows how the analysis is set up for the matched tumor-normal tissue pair sample versus un-matched sample. For matched tumor (T) and normal (N) the AA and BB calls from the normal aren't considered. The normal AB calls, tumor AA, BB and AB and no calls are considered. For unmatched the AA, AB, BB and NC calls for the reference pool and test sample.

Figure 28:
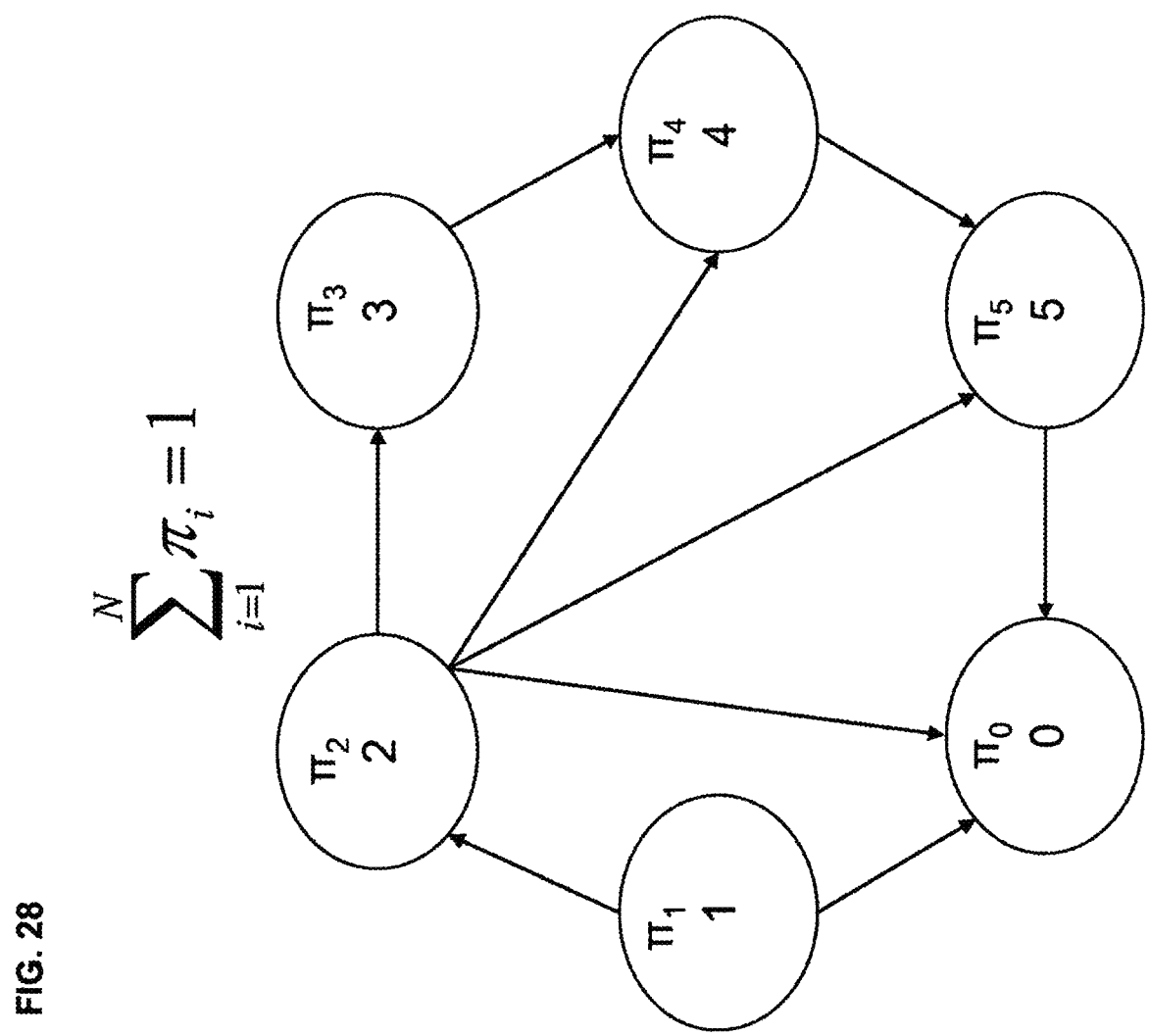
FIG. 28 illustrates prior knowledge about a given state.

FIG. 28 illustrates the prior probabilities. Determine what if any prior knowledge about a given state is available. The sum of the probabilities is 1 over the N states.

$$\sum_{i=1}^{N} \pi_i = 1.$$

For copy number with states: [0,1,2,3,4,5], for normal samples the probabilities of the states are [0.05, 0.05, 0.9, 0.05, 0.05], for unknown samples the probabilities for each state are even [0.2, 0.2, 0.2, 0.2, 0.2]. For LOH with 2 states[0,1], for matched samples the probabilities may be estimated based on a rate of LOH for AB in the reference, for unmatched samples the probabilities may be estimates based on SNP heterogeneity rate and genotyping error in a reference pool.

Figure 29:
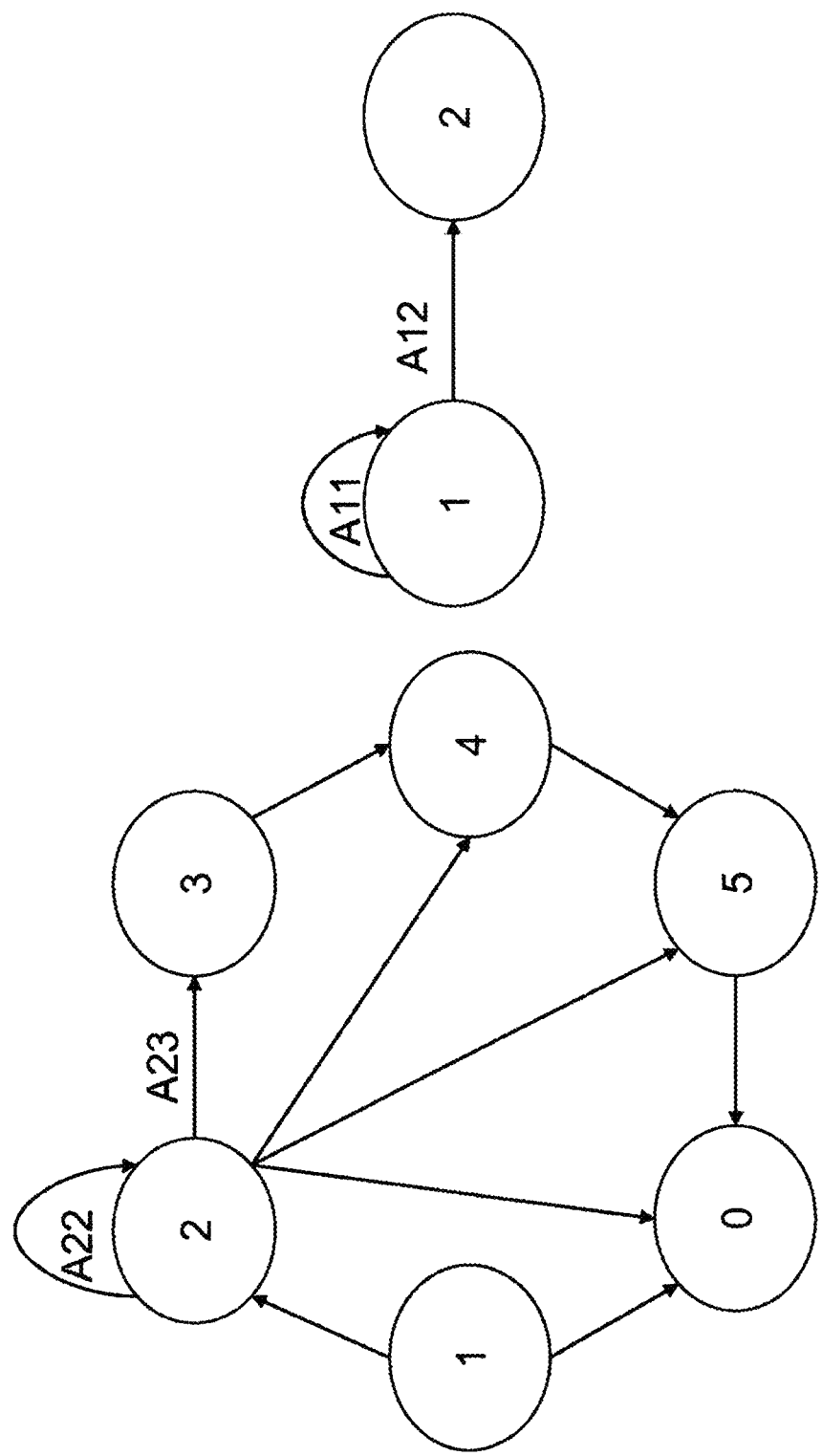
FIG. 29 illustrates the probability of transitions occurring from one state to another.

For estimation of prior probabilities for LOH in un-matched samples, in general ObsHets→{LOH,RET} and ObsHetCalls$_{sample}$=(($\pi_{RETsample}$)(HetRate$_{RETsample}$))+(($\pi_{LOHsample}$)(HetRate$_{LOHsample}$)). In tumors ObsHetCalls$_{sample}$=(($\pi_{RETsample}$)(HetRate$_{RET}$))+(($\pi_{LOHsample}$)(ε)) where ε is genotyping error rate, for ε→0 ObsHetCalls$_{sample}$≈$\pi_{RETsample}$×HetRate$_{RET}$. HetRate$_{RET}$≈Avg (HetRate$_{RET}$) (No Calls may be included or excluded) UpperBound ($\pi_{RETsample}$)=ε and $\pi_{LOHsample}$=1−$\pi_{RETsample}$ FIG. 28 and FIG. 29 illustrate the transition probability component of the model. Probability of transitions occurring from one state to another are provided. Transitions may be self transitions (no change in copy number) or no-self transitions (change in copy number). In preferred embodiments stationary transition matrix (STM) parameters are used and the probability of self transitions is set at 0.9 and the probabilities of all non-self transitions are assumed to be equal.

FIG. 26 shows an Ergodic model with 6 states and all state to state transitions are permitted. The components are (i) observations (O), (ii) states (true underlying)(N), and (iii)

probabilities: A. prior (π); B. transition (A) and C. Emission (B). In the model: λ=(A, B, π). There are different probabilities with an underlying state being the same as the prior state, Allowed transitions are shown by arrows and different states are numbered 0 to 5. The observations O={$O_1, O_1, O_3, O_5, O_2, \ldots O_n$} (for 1, 2, 3, 4, 5, . . . d). Evaluate the probability of the observation sequence given the model λ.

FIG. 27 shows how the analysis is set up for the matched tumor-normal tissue pair sample versus un-matched sample.

FIG. 28 relates to prior knowledge about a given state. For each given state a determination is made of what prior knowledge is available for that state. The sum of the probabilities of all states is 1. For CN[0,1,2,3,4] the probability of each state for normal samples is [0.05, 0.05, 0.9, 0.05, 0.05] (highest probability for CN=2). For unknowns the probabilities are equal [0.2, 0.2, 0.2, 0.2, 0.2]. For LOH [0,1] for matched samples estimate the prior state based on the rate of LOH for AB in the reference. For unmatched samples estimate the prior state based on the SNP heterogeneity rate and genotyping error in the reference.

FIG. 29 shows the probability of transitions occurring from one state to another. Copy number is shown on the left and LOH on the right. The transitions can be self transitions (A22 for CN or A11 for LOH) of non-self transitions (A23 for CN or A12 for LOH). The stationary transition matrix (STM) parameters are self transitions 0.9 and non-self transitions equal. Non-stationary transition materis (NSTM) parameters are priors and transition decay. A combination of STM and NSTM may be used.

Figure 30:
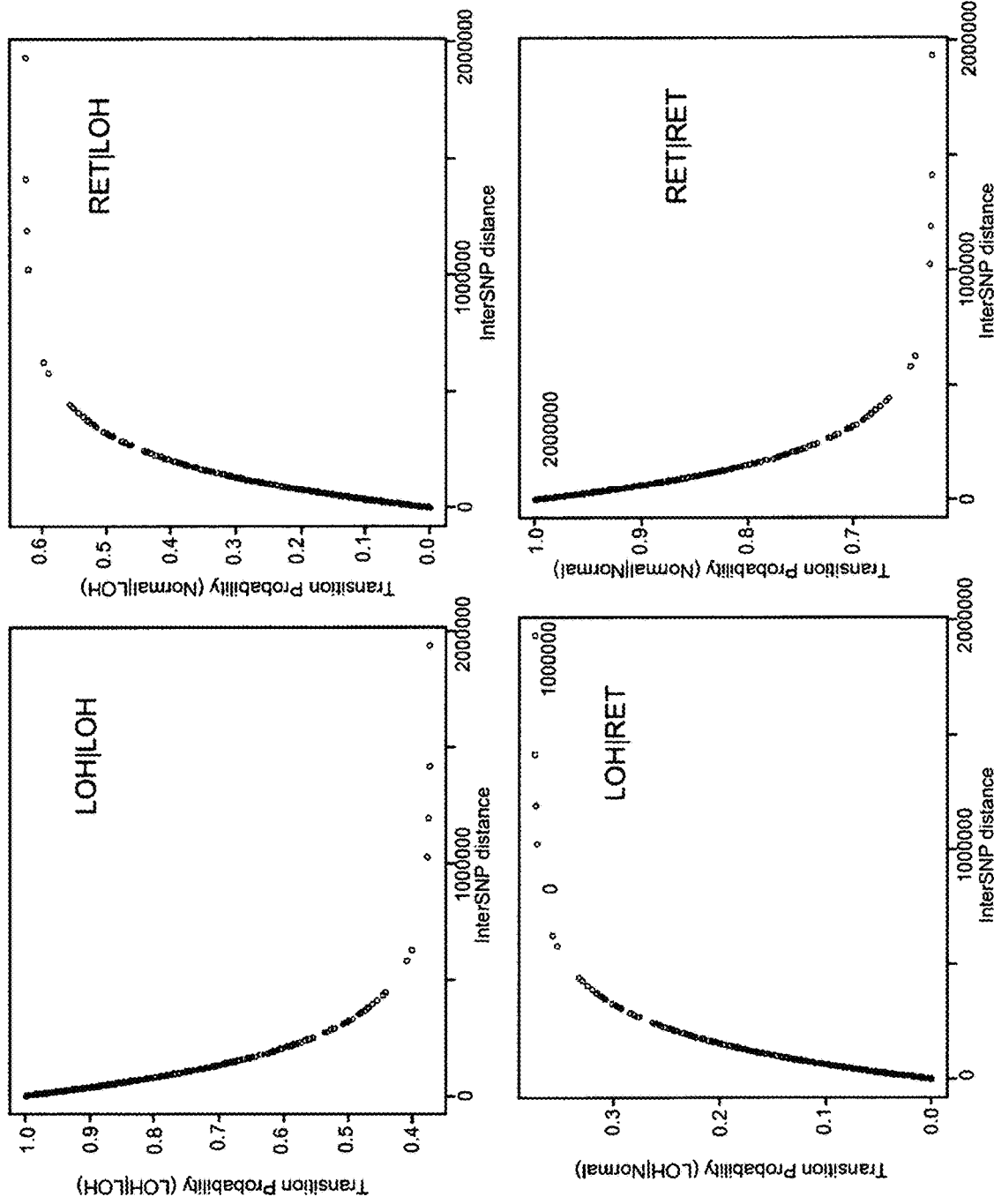
FIG. 30 shows a non-stationary transition matrix.

FIG. 30 shows a non-stationary transition matrix. The transition probabilities are plotted against the inter SNP distance for LOH/LOH, RET/LOH, LOH/RET and RET/RET. The following equation may be used:

$$\hat{i} \times (e^{-B\Delta d}) + \hat{\pi}(1 - e^{B\Delta d})$$

where $\pi_i$ is the prior associated with a state i, $\Delta d$ is the inter-SNP distance, LOH state of prior SNP i and β, β' is the decay parameter. The prior is [LOH, RET]:[0.3742, 0.6258]. Inter SNP distance is on the X axis and transition probabilities are on the y-axis.

Figure 31:
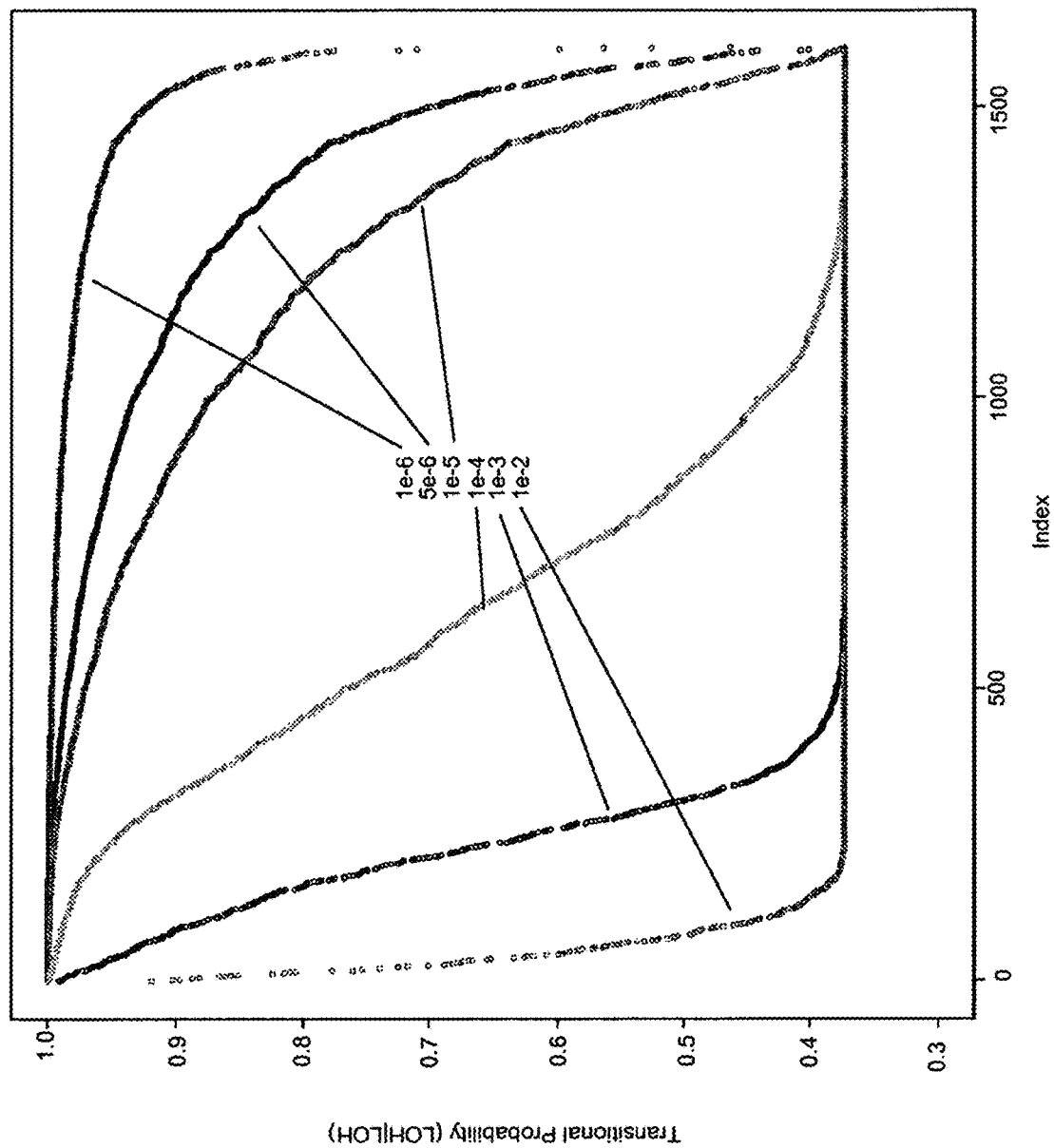
FIG. 31 shows transition probability for LOH/LOH v. index.

FIG. 31 shows transition probability for LOH/LOH v. index.

Figure 32:
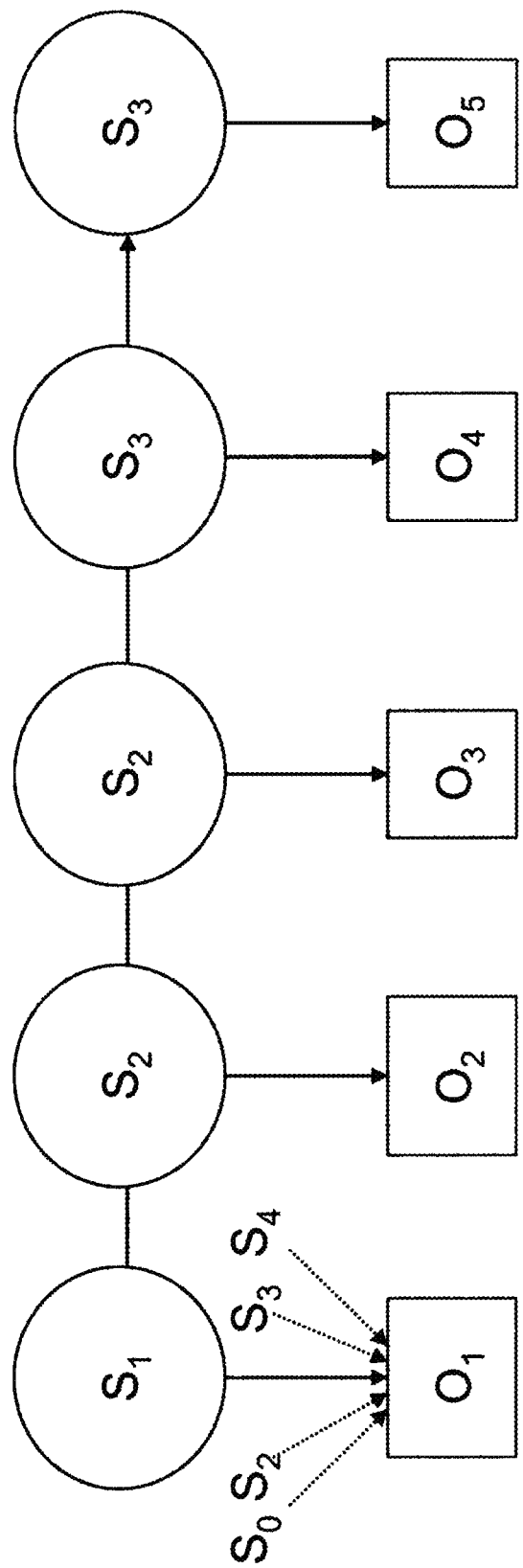
FIG. 32 shows emission probability for CN for emission from a hidden state.

FIG. 32 shows emission probability for CN for emission from a hidden state. States are indicated by S and observations by O. The emission parameters are (1) mean of a state: fixed or clustering based initial estimates: $\mu_0 \leq \mu_i \leq \mu_2 \leq \mu_3 \leq \mu_4$, and (2) variance of a state, equal or unequal.

FIG. 33 shows emission probability for LOH with matched tumor-normal samples. The genotyping error, ε, is 0.02.

Figure 34:
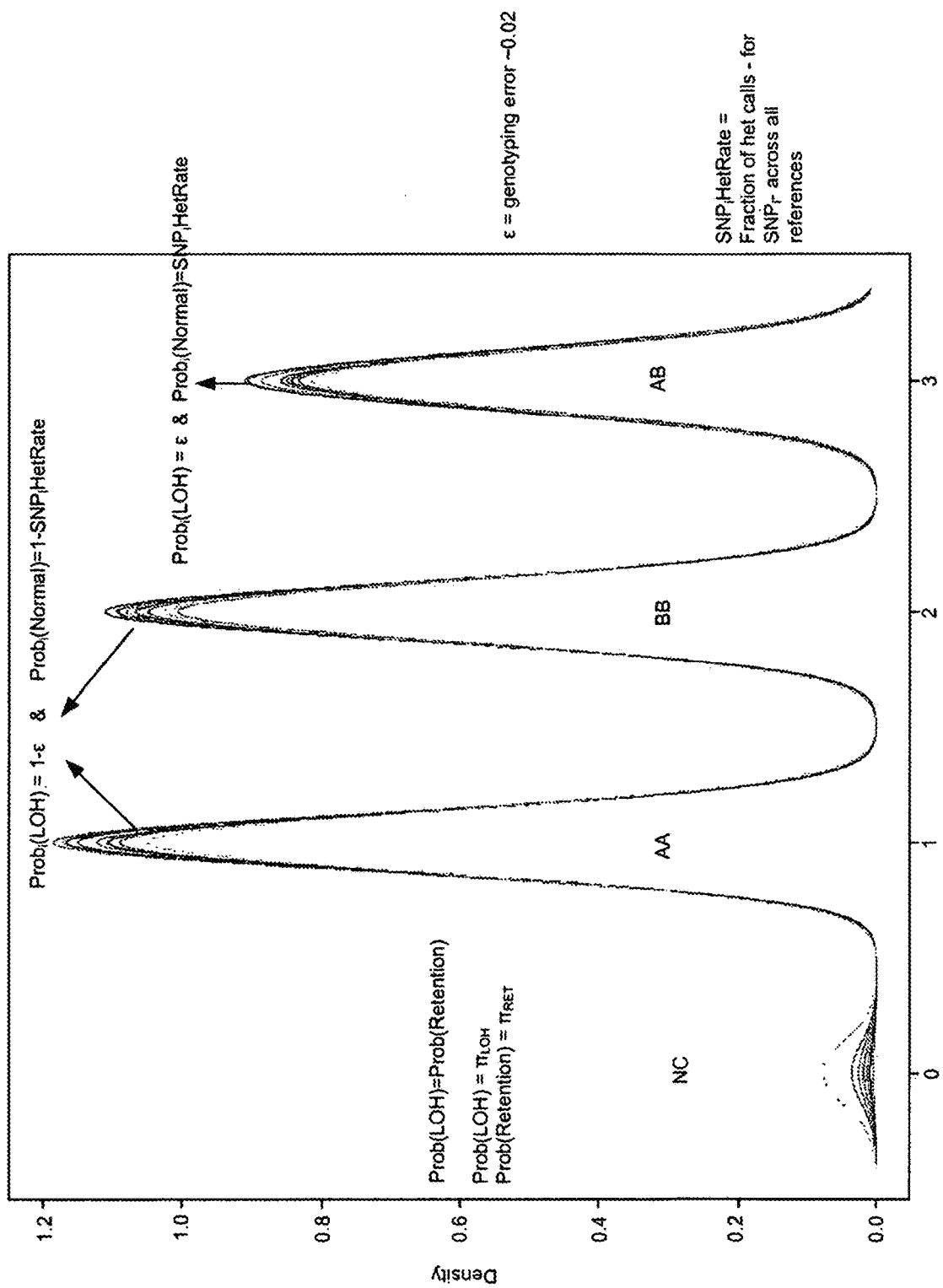
FIG. 34 shows emission probability for LOH with un-matched samples.

FIG. 34 shows emission probability for LOH with un-matched samples.

Figure 35:
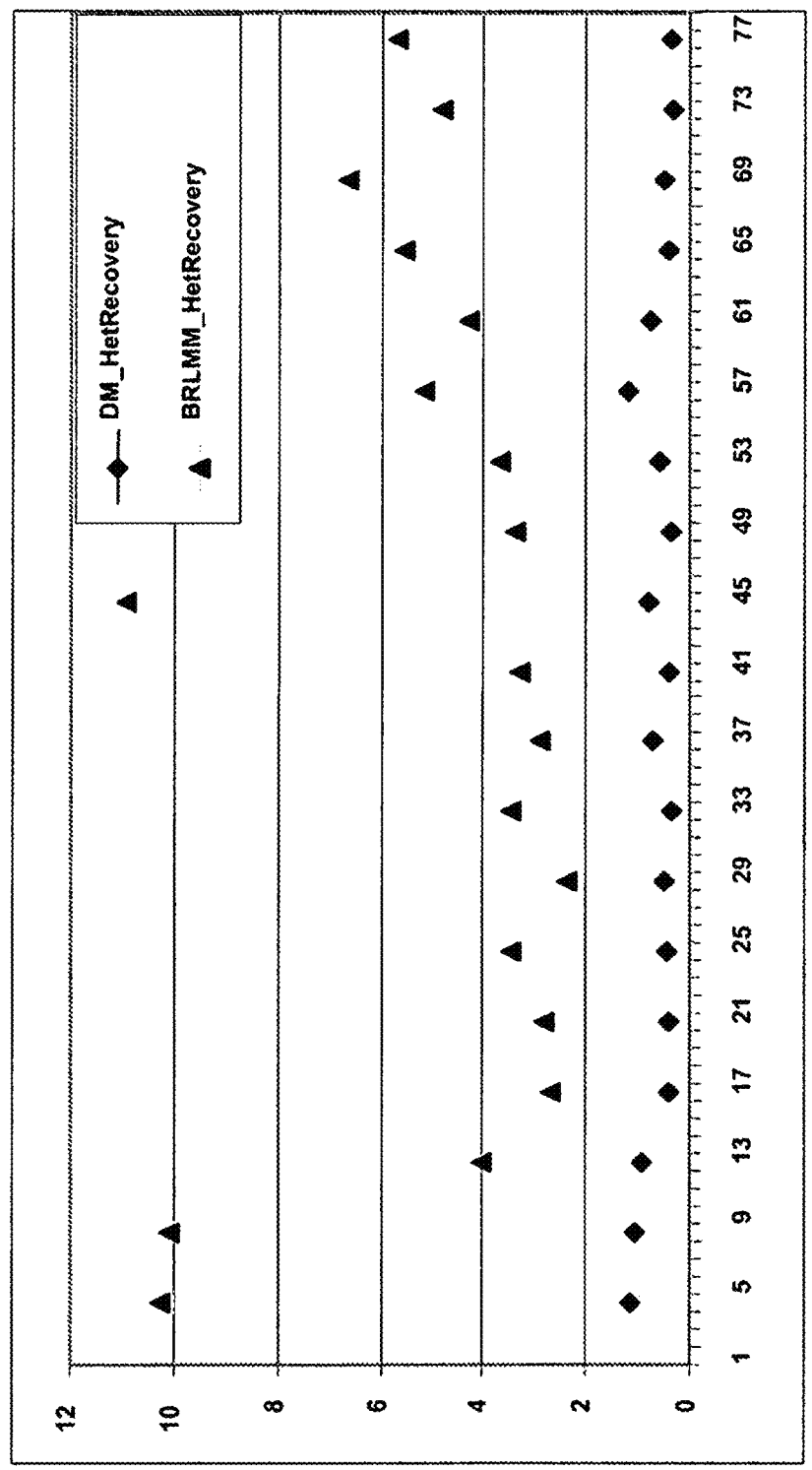
FIG. 35 shows recovery of heterozygous calls when BRLMM is used instead of DM.

FIG. 35 is discussed below.

Figure 36:
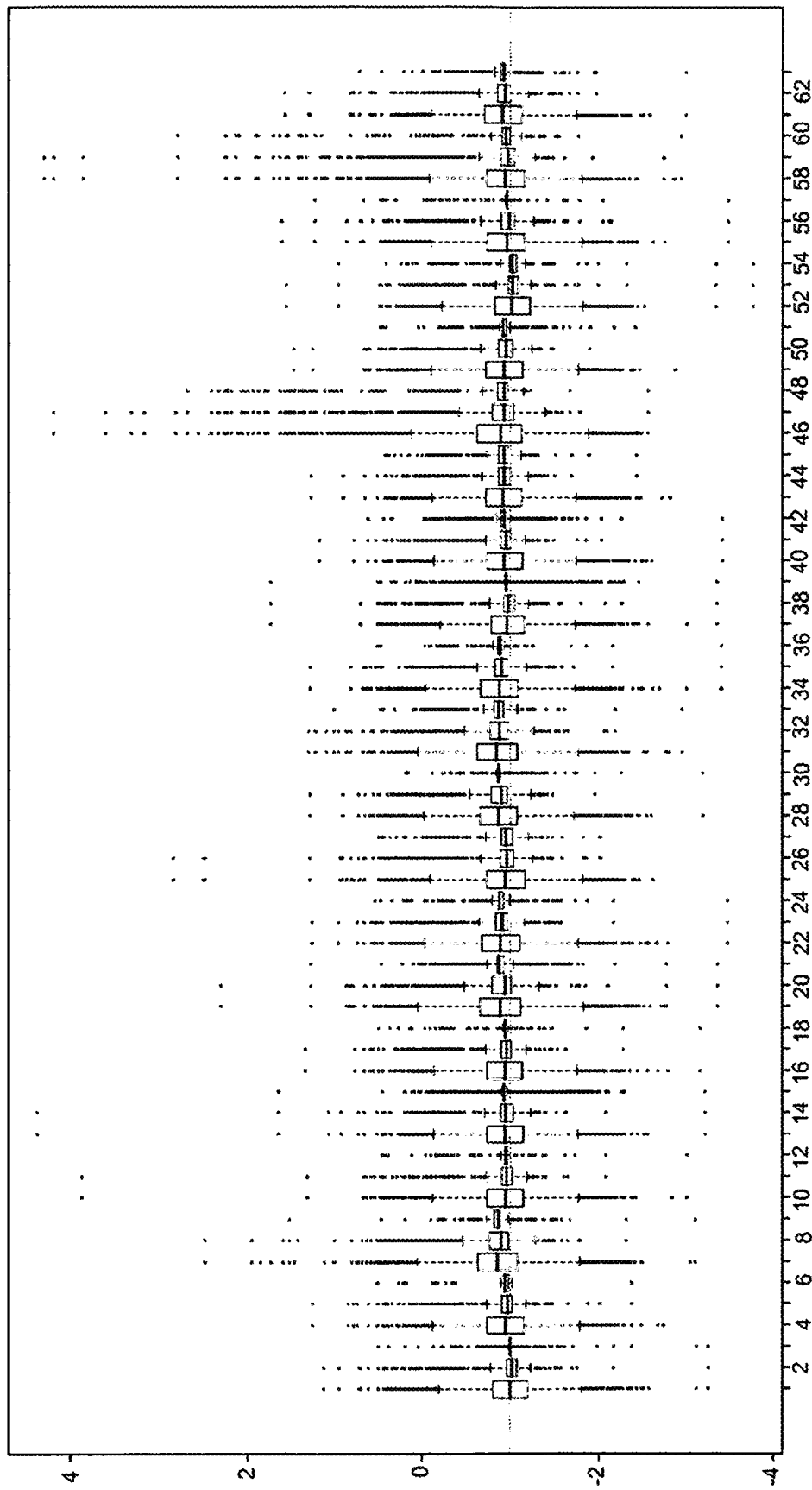
FIG. 36 shows variance reduction via EM optimization.
Figure 37:
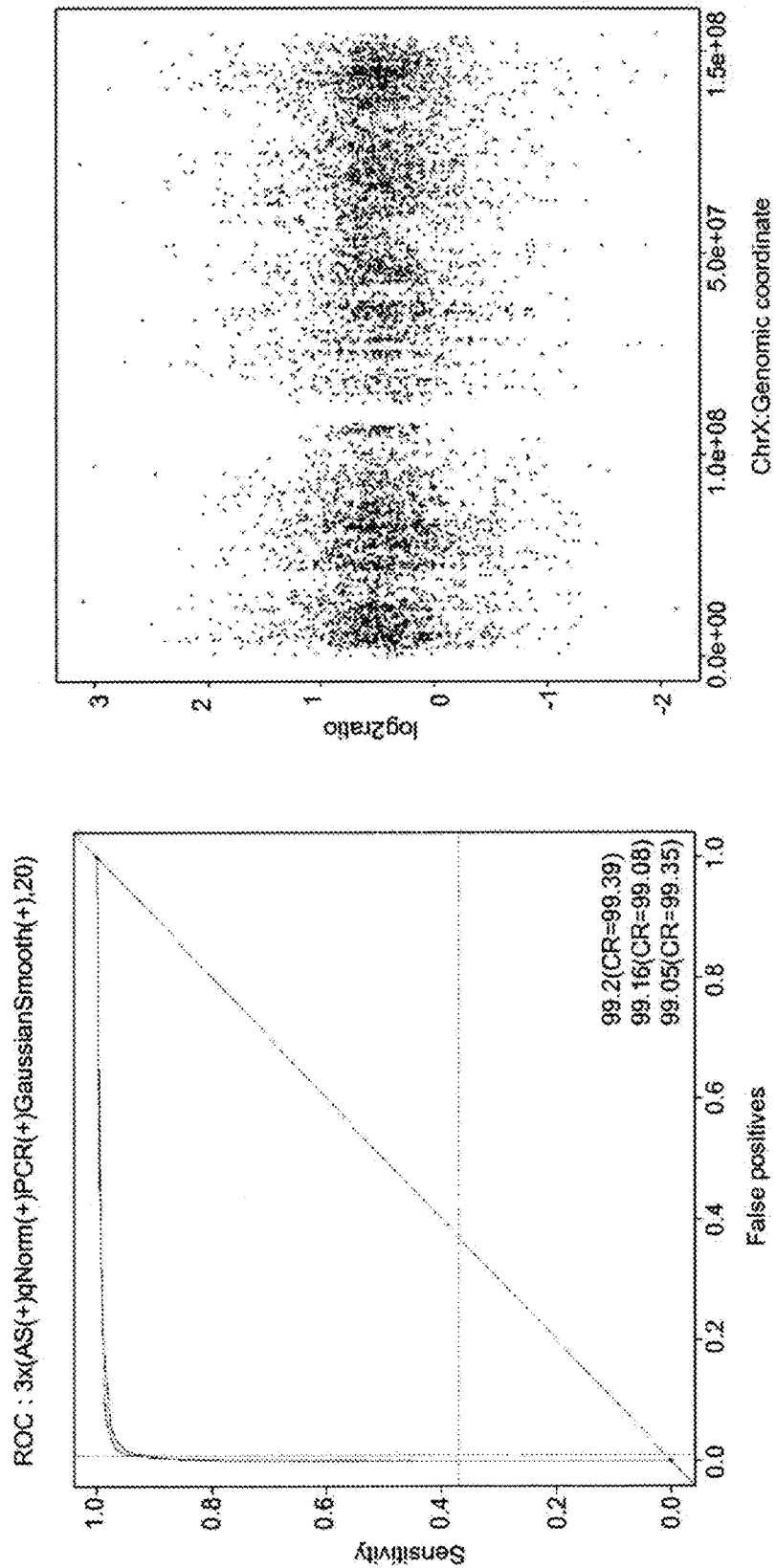
FIG. 37 shows CN performance metrics.

FIG. 36 shows variance reduction via EM optimization. HMM may be done with or without EM optimization. Using EM optimization decreases false positive rates.

FIG. 36 shows CN performance metrics. The graph on the left shows the area under the curve (AUC) which is a ROC based metric for detection of 1x versus 2x copies in chromosome X. Sensitivity on y-axis v. false positives on x-axis. The graph on the right shows IQR on inter-quartile range of loge ratio which is a measure of variance. Log2ratio is on the y-axis and the genomic coordinate on the chrX is on the x-axis.

Figure 38:
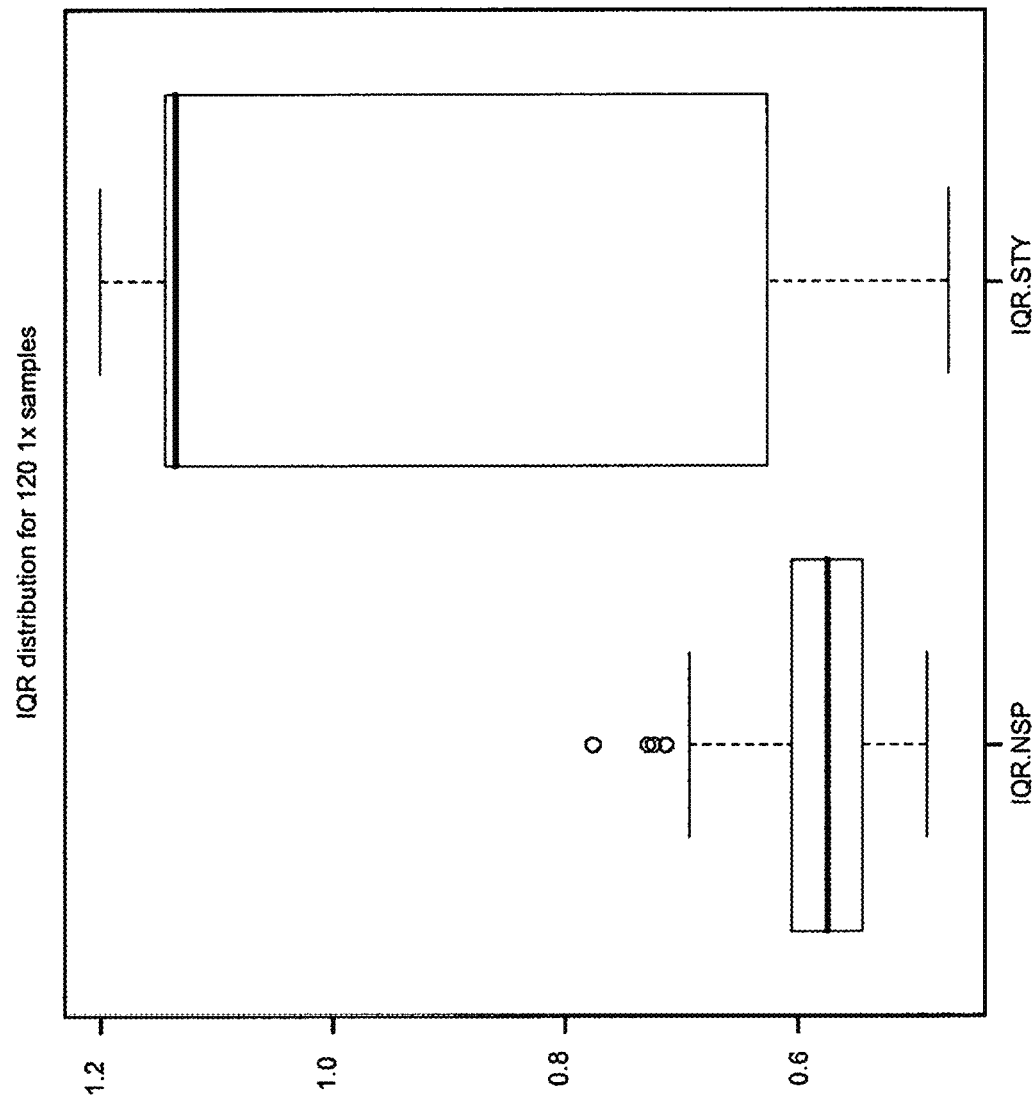
FIG. 38 shows IQR distribution for 120 IX samples.

FIG. 38 shows IQR distribution for 120 1X samples.

Figure 39:
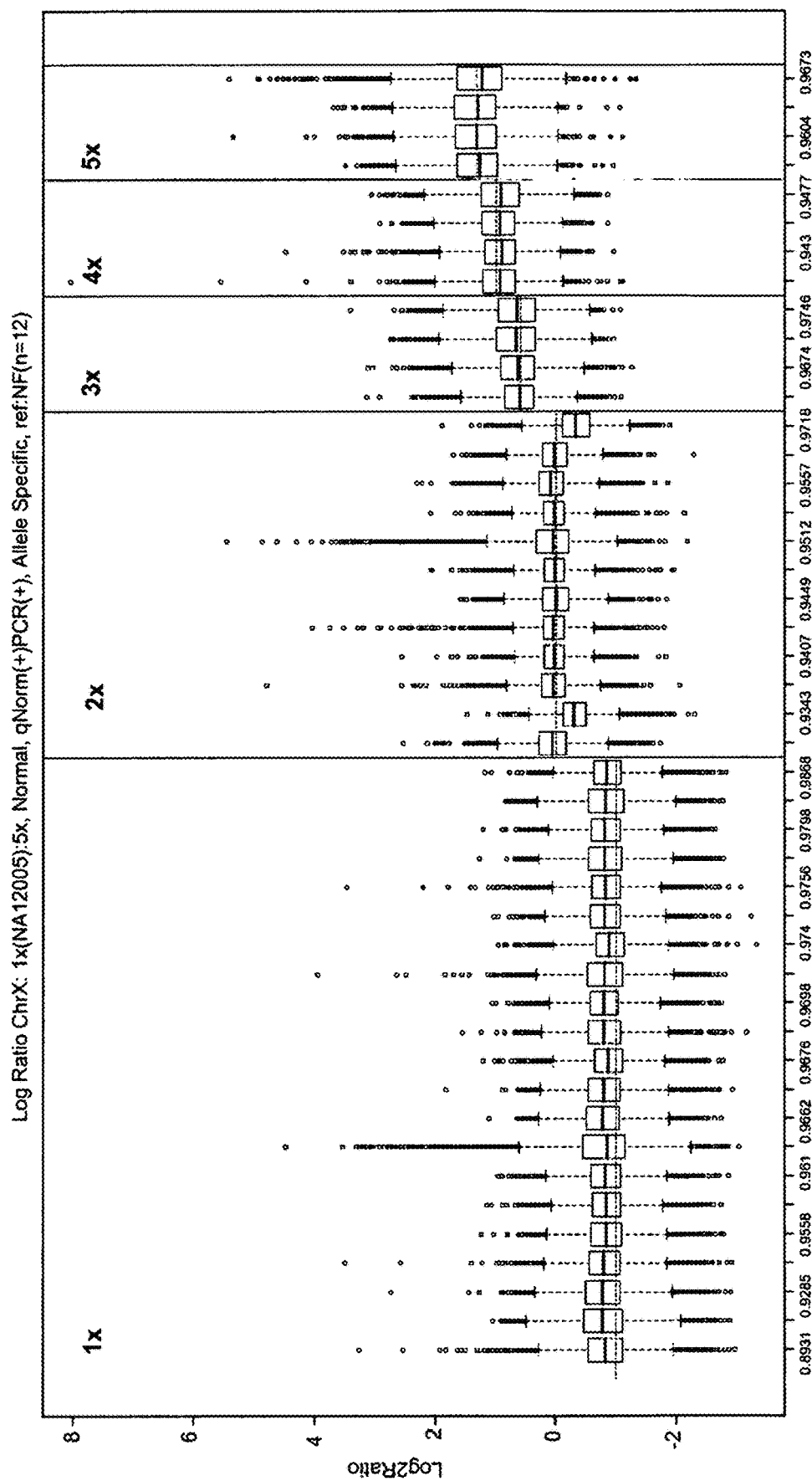
FIG. 39 shows data for 1, 2, 3, 4, or 5X post PCR correction using 12 references and looking at 5710 SNPs.

FIG. 39 shows data for 1, 2, 3, 4, or 5X post PCR correction using 12 references and looking at 5710 SNPs.

Figure 40:
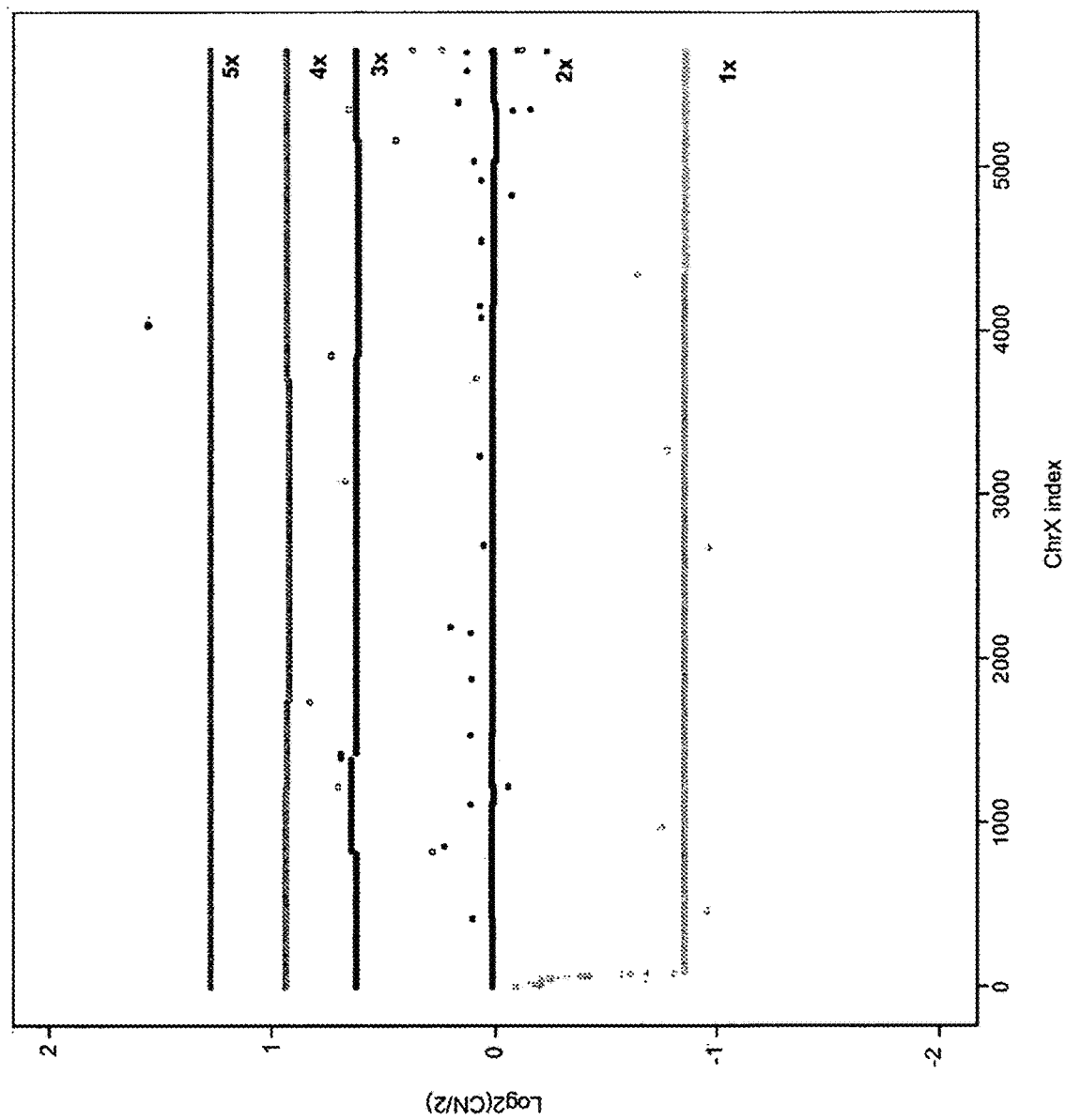
FIG. 40 shows the mean distribution per SNP across samples.

FIG. 40 shows the mean distribution per SNP across samples. For the IX there are 21 samples, 12 samples for 2x and 4 samples each for 3X-5X (same samples as FIG. 39). The data is post HMM and there are 5710 SNPs and 27 reference samples.

Figure 41:
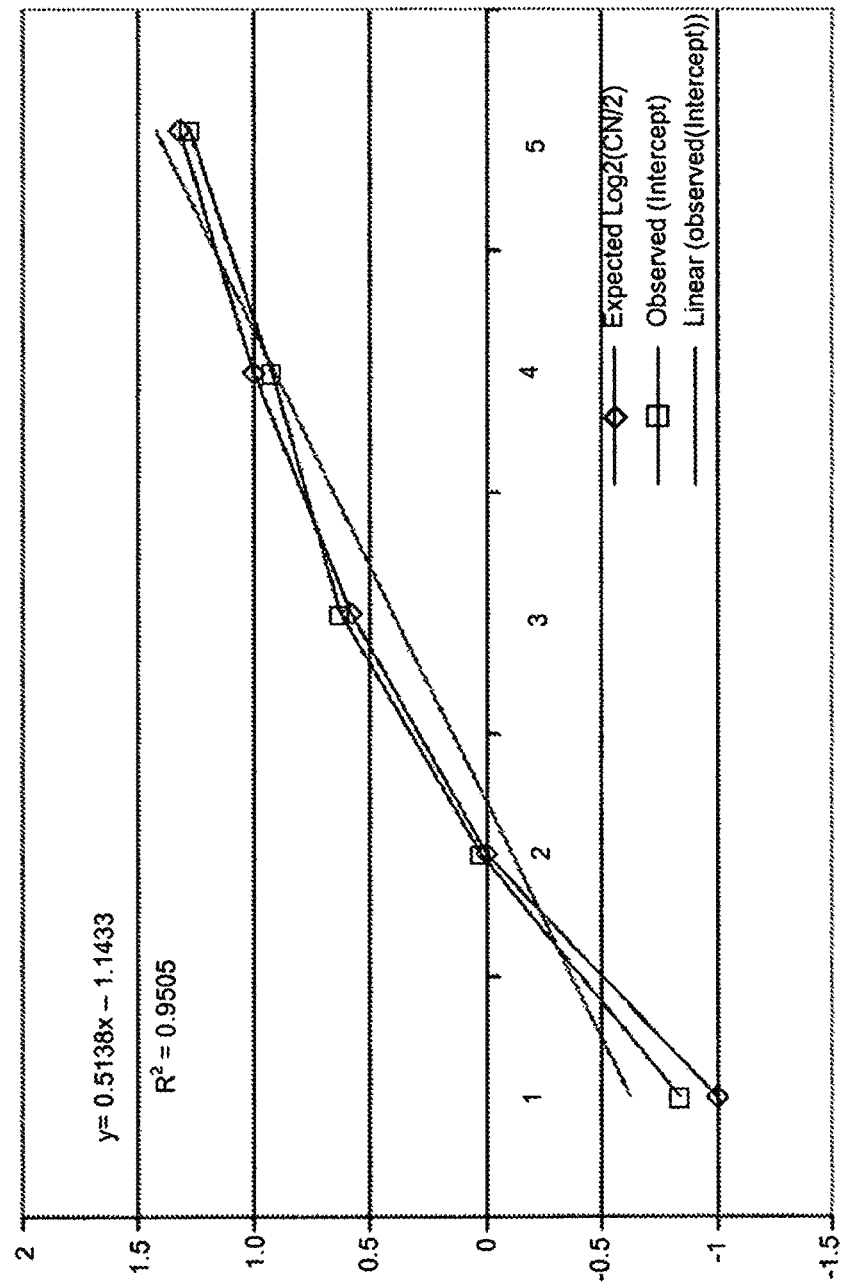
FIG. 41 shows a plot of the observed vs. expected.
Figure 42A:
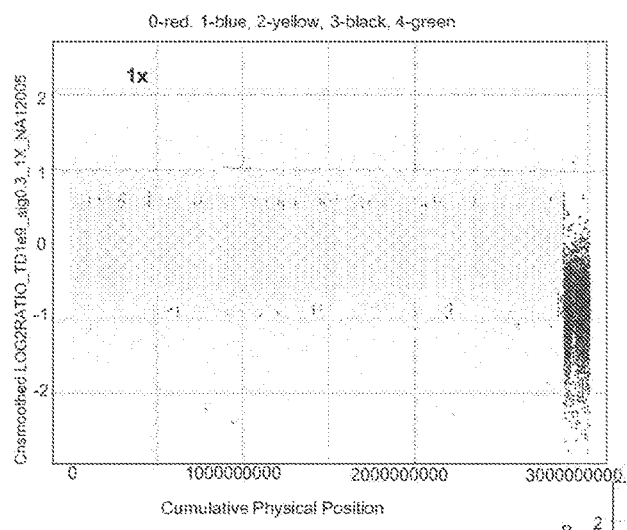
FIGS. 42A-42D illustrate representative examples of final HMM-based segmentation for CN states for 1x, 2x, 3x, and 4x respectively.
Figure 42B:
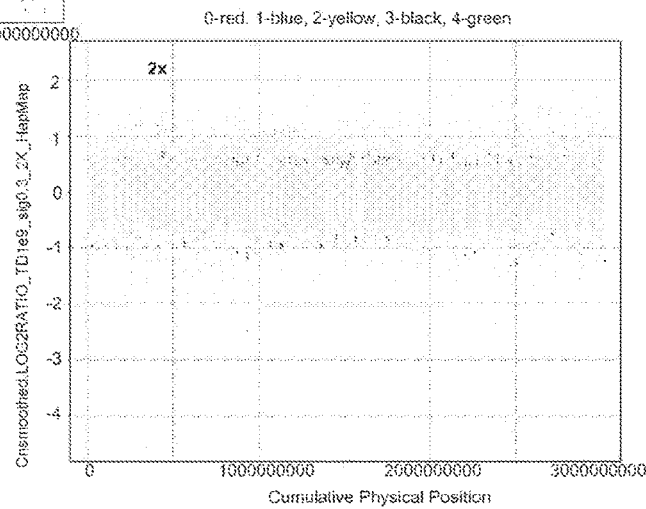
Figure 42C:
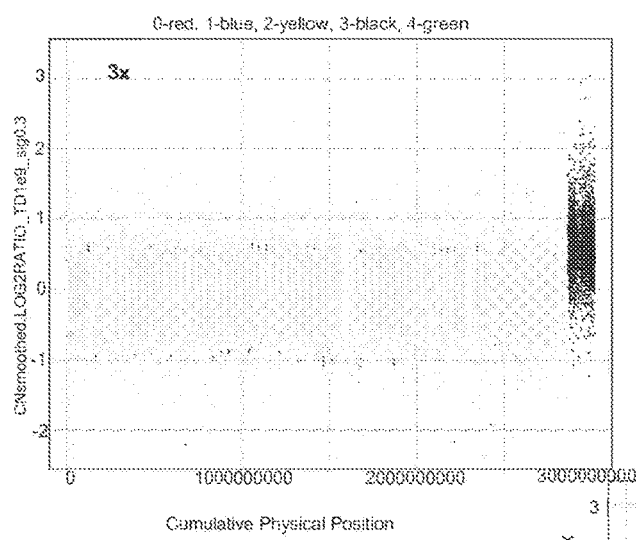
Figure 42D:
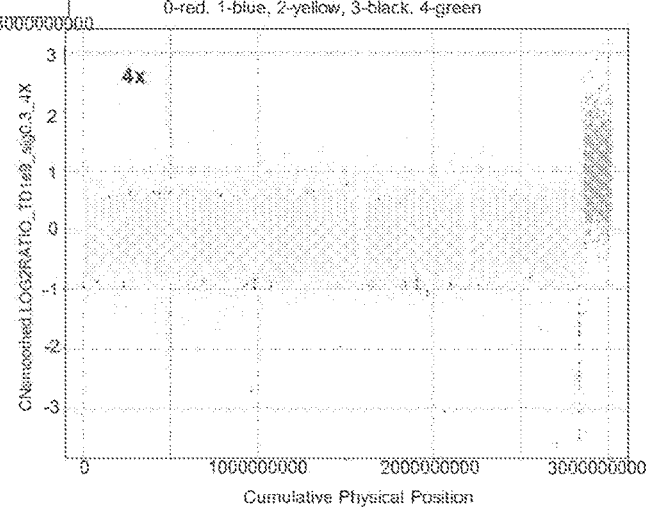

FIG. 41 shows a plot of the observed vs. expected. The observed and expected intercepts and the MAD and z-stat are shown in the table 1.

TABLE 1

| | Expected (intercept) | Observed (Intercept) | MAD | z-stat |
|---|---|---|---|---|
| 1x | −1 | −0.8426 | 0.0012 | −858.448 |
| 2x | 0 | 0.0129 | 0.0038 | 0 |
| 3x | 0.584963 | 0.6239 | 0.0015 | 1680.349 |
| 4x | 1 | 0.9265 | 0.009 | 2267.455 |
| 5x | 1.321928 | 1.26950 | 0.001 | 4719.845 |

The algorithmic performance has been characterized using the following chromosome X titration datasets which take into account inter-laboratory variability: o 1x: 21 samples o 2x:12 samples o 3x (NA04626): 4 samples where 3+1 experiments were performed in 2 different laboratories. O 4x (NA01416): 4 samples where 3+1 experiments were performed in 2 different laboratories. 0 5x (NA06061): 4 samples where 3+1 experiments were performed in 2 different laboratories. The results presented comprise two distinct sets of analyses: 1) Bias versus variance analysis performed for the logSum and sumLog approaches and 2) ROC analysis for estimation of specificity and sensitivity of the various algorithmic components. FIGS. 42A, 42B, 42C, and 42D is representative of the final HMM based segmentation of the CN states. In these panels all chromosomal positions are concatenated in chromosomal order (1-X). The x-axis represents the concatenated genomic position. The y-axis represents the smoothed log 2ratio value as generated via the sumlog option with a nominal smoothing bandwidth of 15k. The bulk of the data in all the titration samples is diploid and this is denoted via the yellow colormap. The single copy in chromosome X is denoted by blue; 3 copies in chromosome X are denoted by black; 4 copies are denoted by green and five copies denoted by cyan.

Subsequent to the co-optimization of both bias and variance, the logSum approach additionally optimizes for variance at the cost of bias; conversely the sumLog approach additionally optimizes for bias at the cost of variance. While this does not affect the segmentation of data into its different CN states corresponding to amplification/deletion or copy neutral status, in case of the former the absolute value corresponding to CN=3, which is ideally 0.58 is compressed towards 0. The latter of course preserves this precision of absolute value but suffers from higher variance.

Figure 43:
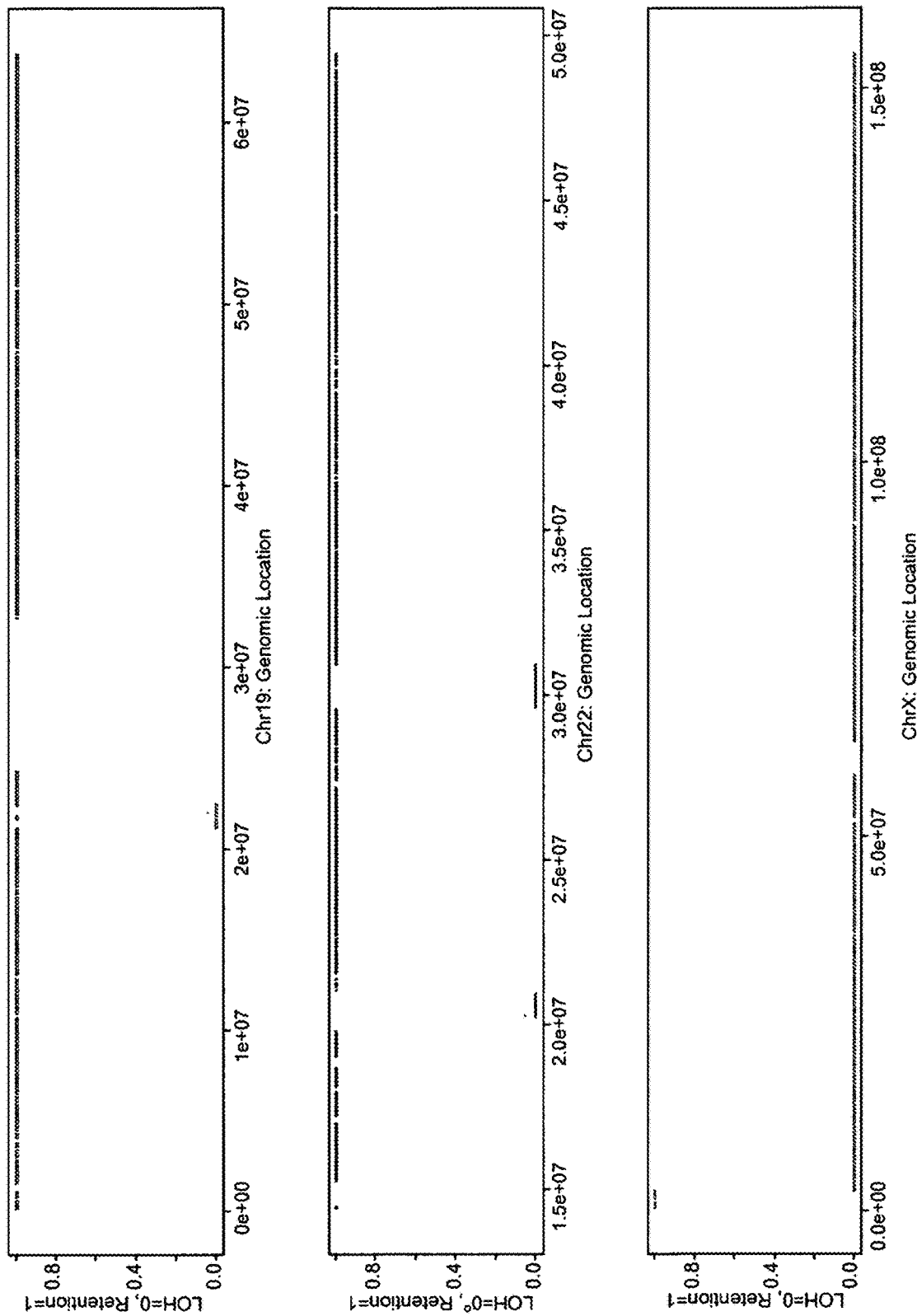
FIG. 43 shows LOH validation data for chromosome X.

FIG. 43 shows LOH validation in chromosome X. The sample is NA10851 which is HapMap male and reference is 15 HapMap females. The top panel is Chr19, the middle is Chr22 and the bottom is ChrX. As expected the data show a single copy of the X chromosome in the male as compared to the female reference.

Figure 44:
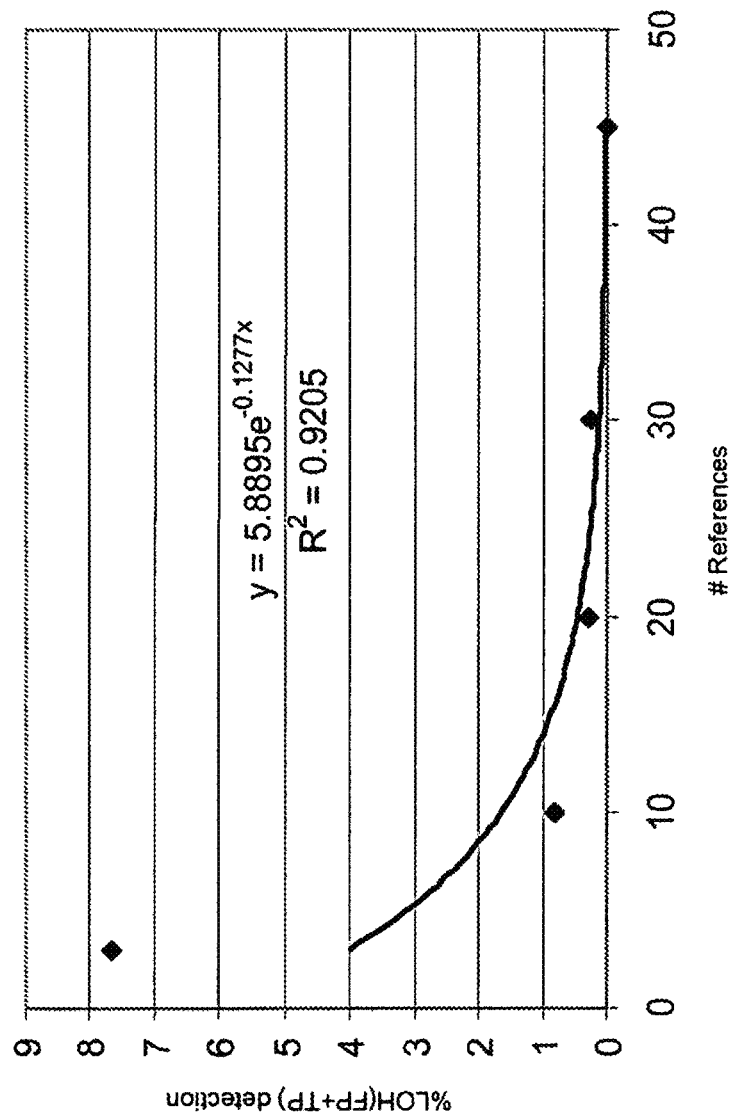
FIG. 44 shows optimization of reference sample size for LOH analysis.

For matched (tumor-normal) LOH analysis: S=total number of SNPs, H=total number of het SNPs in N(T-N), $LOH_{true}$=H called LOH in T-N, $RET_{true}$=H called RET in T-N, n=S[H], sensitivity=$\Sigma n[LOH_{TRUE}]/\Sigma\ LOH_{TRUE}$, specificity=$\Sigma n[LOH_{RET}]/\Sigma\ LOH_{RET}$ FIG. 44 shows optimization of reference sample size for LOH analysis. The reference samples are 90 CEU HapMap samples, intra-population sampling, test sample is excluded.

Figure 45:
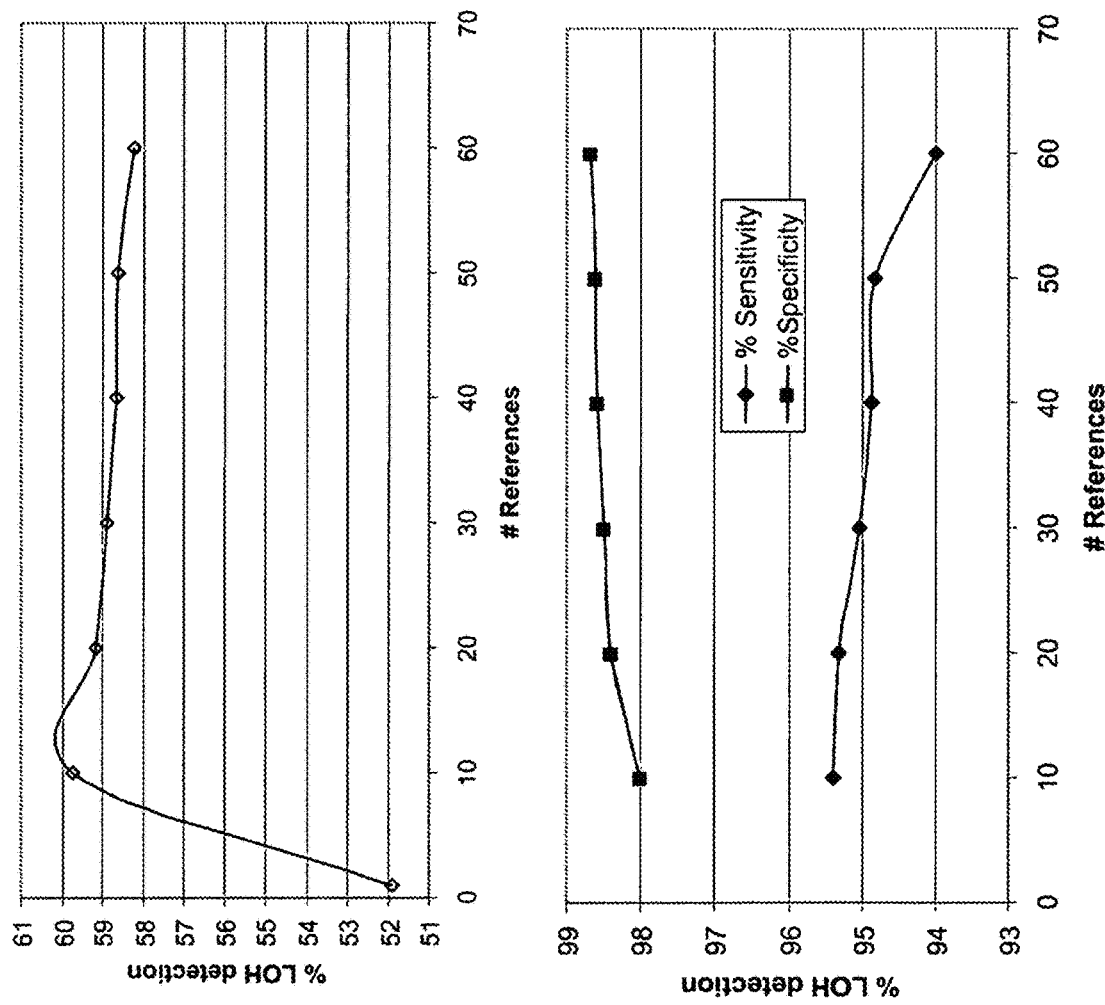
FIG. 45 also shows optimization of reference sample size for LOH analysis.

TRUTH: putatively NO LOH. FIG. 45 also shows optimization of a reference sample size for LOH analysis.

Figure 46:
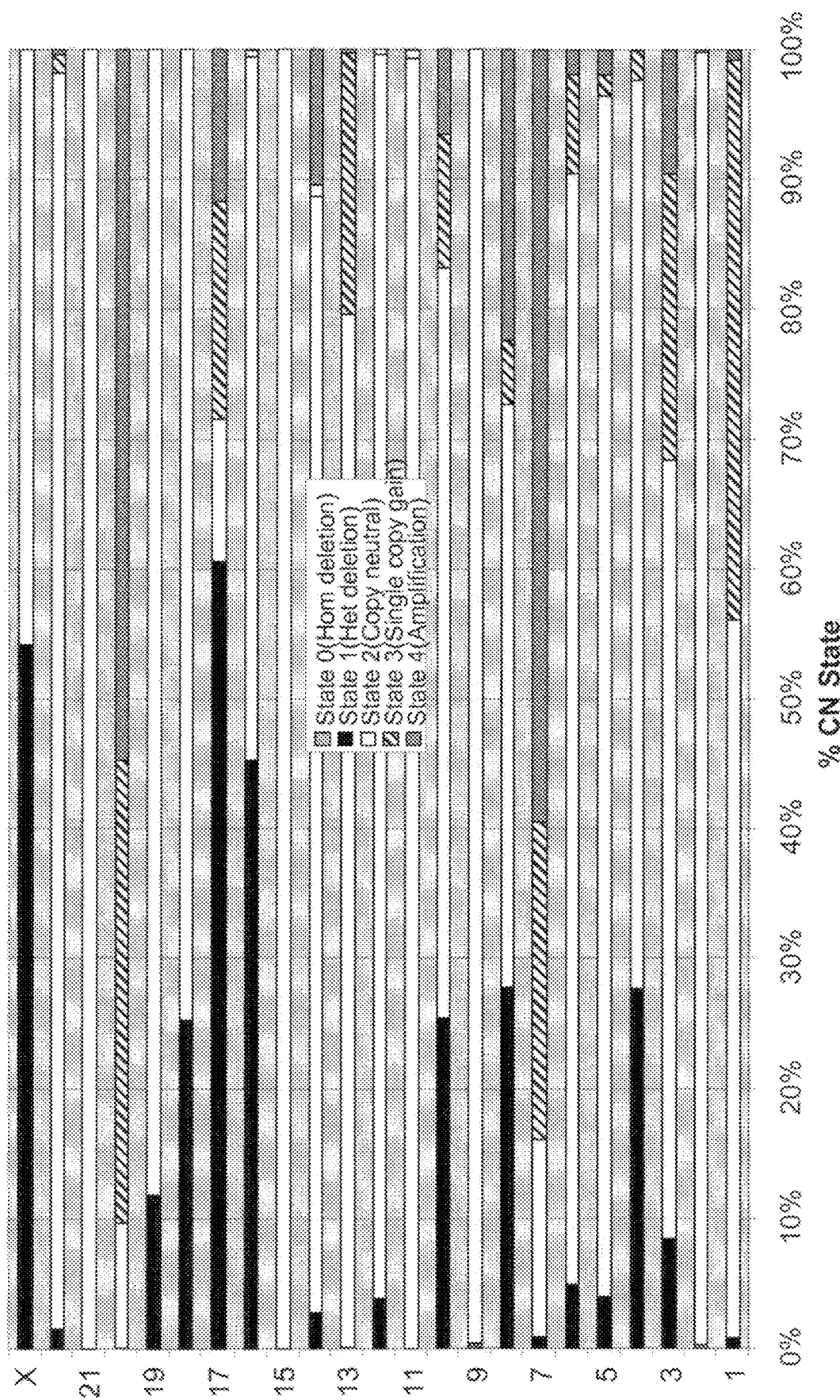
FIG. 46 shows HMM CN state distribution for each chromosome.
Figure 47:
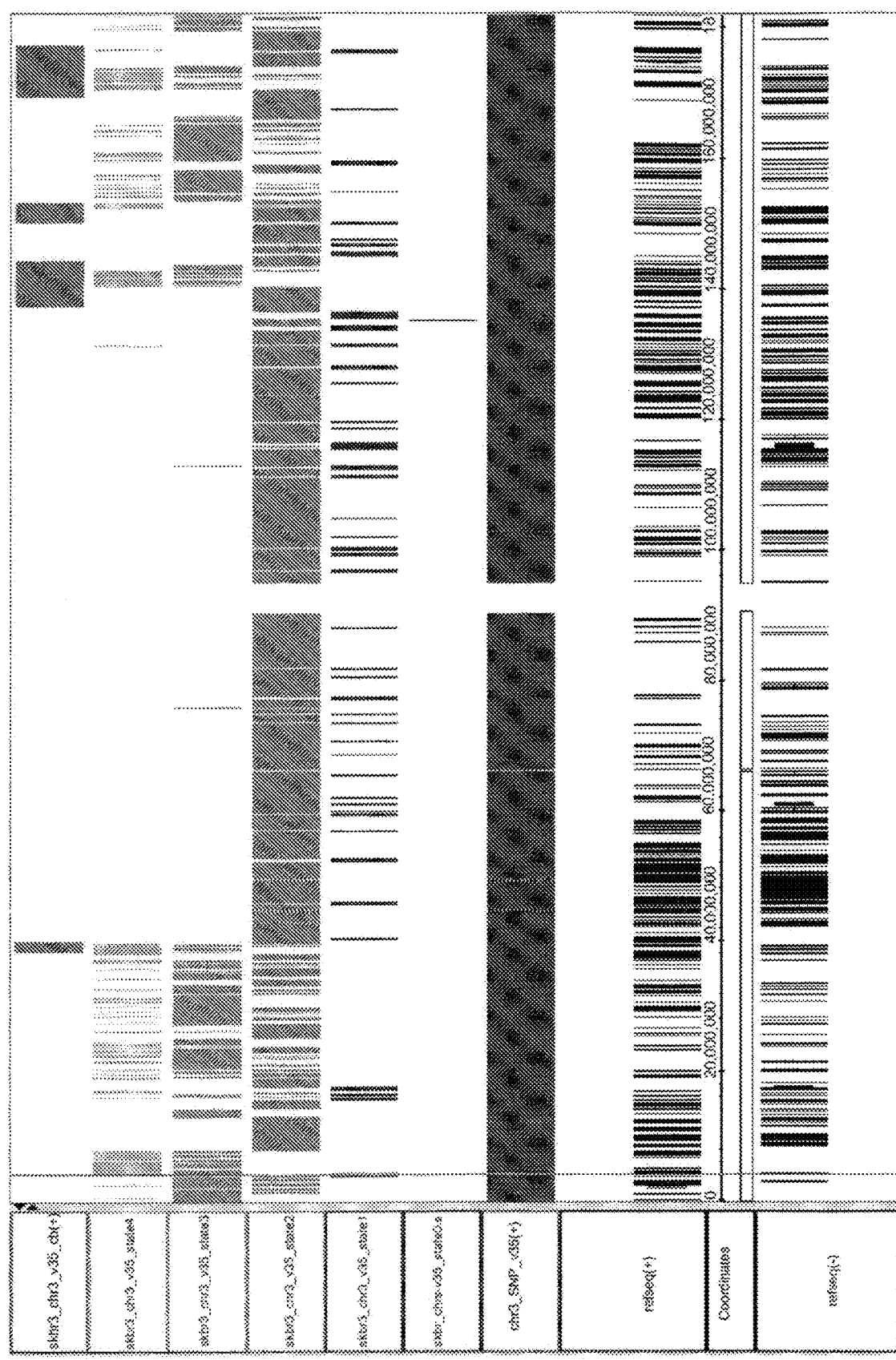
FIG. 47 shows the CN HMM output for Chromosome 3.

FIG. 46 shows HMM CN state distribution for each chromosome. FIG. 47 shows the CN HMM output for Chr. 3. The top track shows cytobands with reported amplifications 3p22.2, 3q22.3m 3q25.1 and 3q26.2-q26.31. The second track from the top shows state 4, the third is state 3, the fourth is state 2, the fifth is state 1 and the sixth is state 0. The seventh shows the SNP coverage.

TABLE 2

| numSNP | % state0 | % state1 | % state2 | % state3 | % state4 |
|---|---|---|---|---|---|
| Chromosome 3 | | | | | |
| 18380 | 0.005441 | 8.43852 | 59.95103 | 22.01306 | 9.591948 |
| Chromosome 17 | | | | | |
| 4854 | 0 | 60.63041 | 11.00124 | 16.68727 | 11.68109 |

TABLE 3

Detection by HMM of CN alterations detected in EGFR pathway using aCGH

| EGFR Pathway Gene | Locus | CN_Exp (LB) | CN_Exp (UB) | CN Obs | State Obs | z-stat |
|---|---|---|---|---|---|---|
| EGF | 4q25 | 0.4 | 0.7 | 0.47 | 2 | 1000 |
| TGFA | 2p13.3 | −0.4 | −0.7 | 0.32 | 2 | 870 |
| NRG2 | 5q31.2(q34) | 0.4 | 0.7 | −0.3 | 2 | −455 |
| EGFR | 7p12.3-p.12.1 | 0.4 | 0.7 | 0.74 | 3 | 1964 |
| ErBB2 | 17q12 | >1 | | 1.45 | 4 | 149.47 |
| PLCG2 | 16q23.2 | −0.4 | −0.7 | −0.65 | 1 | −570 |
| SRC | 20q11.23 | >1 | | 1.22 | 4 | 277.83 |
| RAC1 | 7p22.1 | 0.4 | 0.7 | 1.03 | 4 | 204 |
| RAB5a | 3p24.3 | 0.4 | 0.7 | 0.78 | 3 | 250 |
| MAP2K3 | 17p11.2 | −0.4 | −0.7 | −0.73 | 1 | −133.72 |
| MAP2K6 | 17q24.3 | 0.4 | 0.7 | 0.37 | 3 | 547.75 |
| CHN2 | 7p15.1 | 0.7 | 0.99 | 0.74 | 3 | 2861 |
| PRKCA | 17q24.2 | 0.4 | 0.7 | 0.54 | 3 | 676.71 |
| ERK2 | 22q11.21 | −0.4 | −0.7 | −0.15 | 1 | −6.58 |
| LIMK1 | 7q11.23 | >1 | | 0.62 | 4 | 321 |
| PLD1 | 3q26.31 | 0.4 | 0.7 | 0.404 | 2 | 272 |
| MYC | 8q24 | >1 | | 2.65 | 4 | 1093 |

Figure 48:
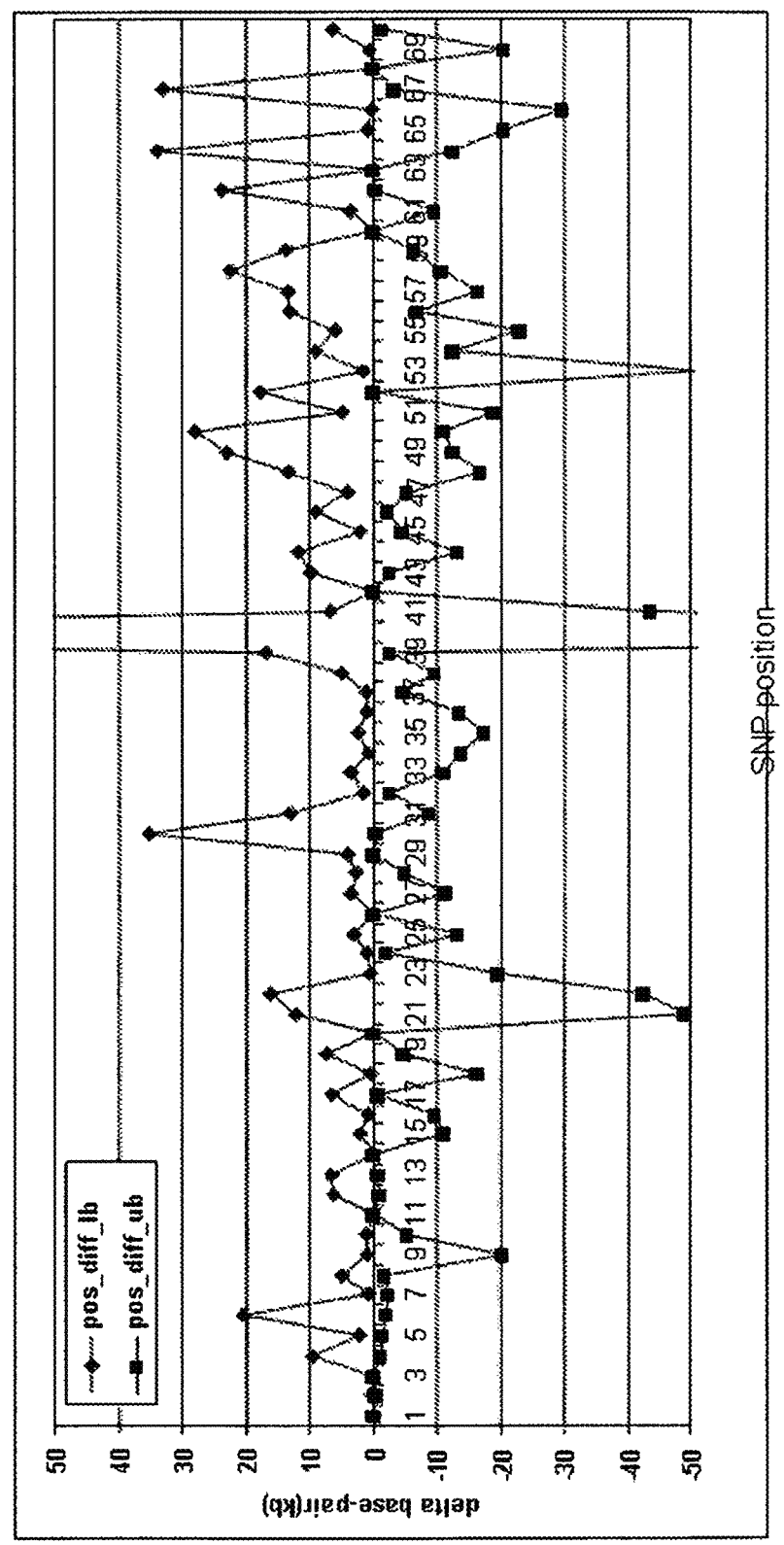
FIG. 48 shows proximity to flanking SNPs.
Figure 49:
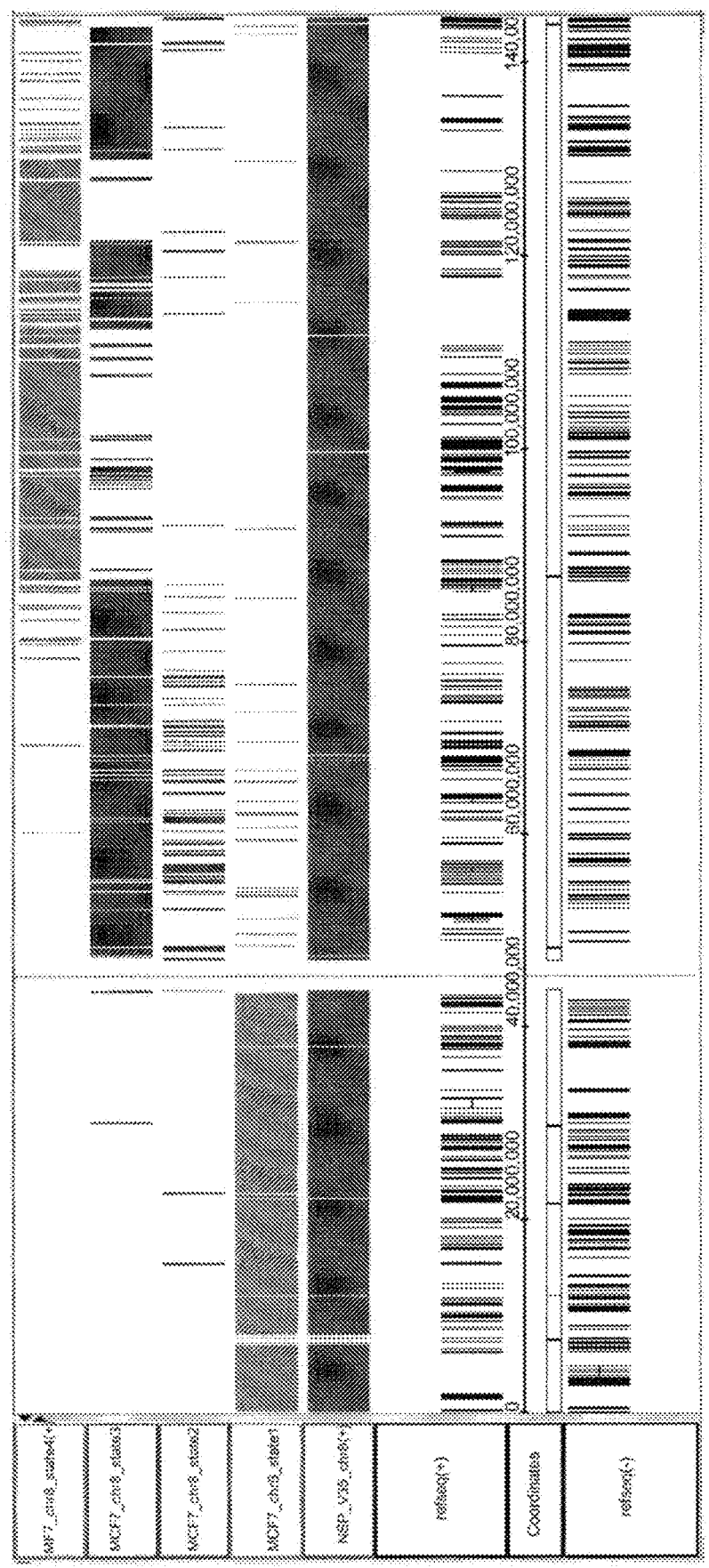
FIG. 49 shows HMM analysis for chromosome 8.

FIG. 48 shows proximity to flanking SNPs. Distance from index SNP to right flanking SNP is "pol_cliff_ub" and the distance from index SNP to left flanking SNP is "pos_cliff_1b" Outliers are +195/−210 kb. FIG. 49 shows CN HMM output for Chromosome 8. Reported deletions in 8p arm and amplifications 8q21.2-q24.21 were observed. The tracks are (from the top): state 4, state 3, state 1, SNPs assayed, refseq(+), coordinates, and refseq(−). The deletion can be seen in the state 1 track on the left and the amplifications can be seen in the state 4 and state 3 tracks. The number of SNPs assayed was 14,840, the % in state 0=0, state 1=37, state 2=4, state 3=36 and state 4=22%.

Matched versus unmatched analysis for LOH of NCI-H2126 (T256). The HMM parameters (un-optimized) are 2 state mode, no calls excluded, no EM optimization, transition decay: $10^{-6}$, computed $\pi_{LOH}$=0.3742, $\pi_{RET}$=0.6258, genotype error rate: 0.01, referencese in un-matched analysis CEU 60 parents, sensitivity is 94% (29688/31583) and specificity is 98.67% (28850/29239).

Figure 50:
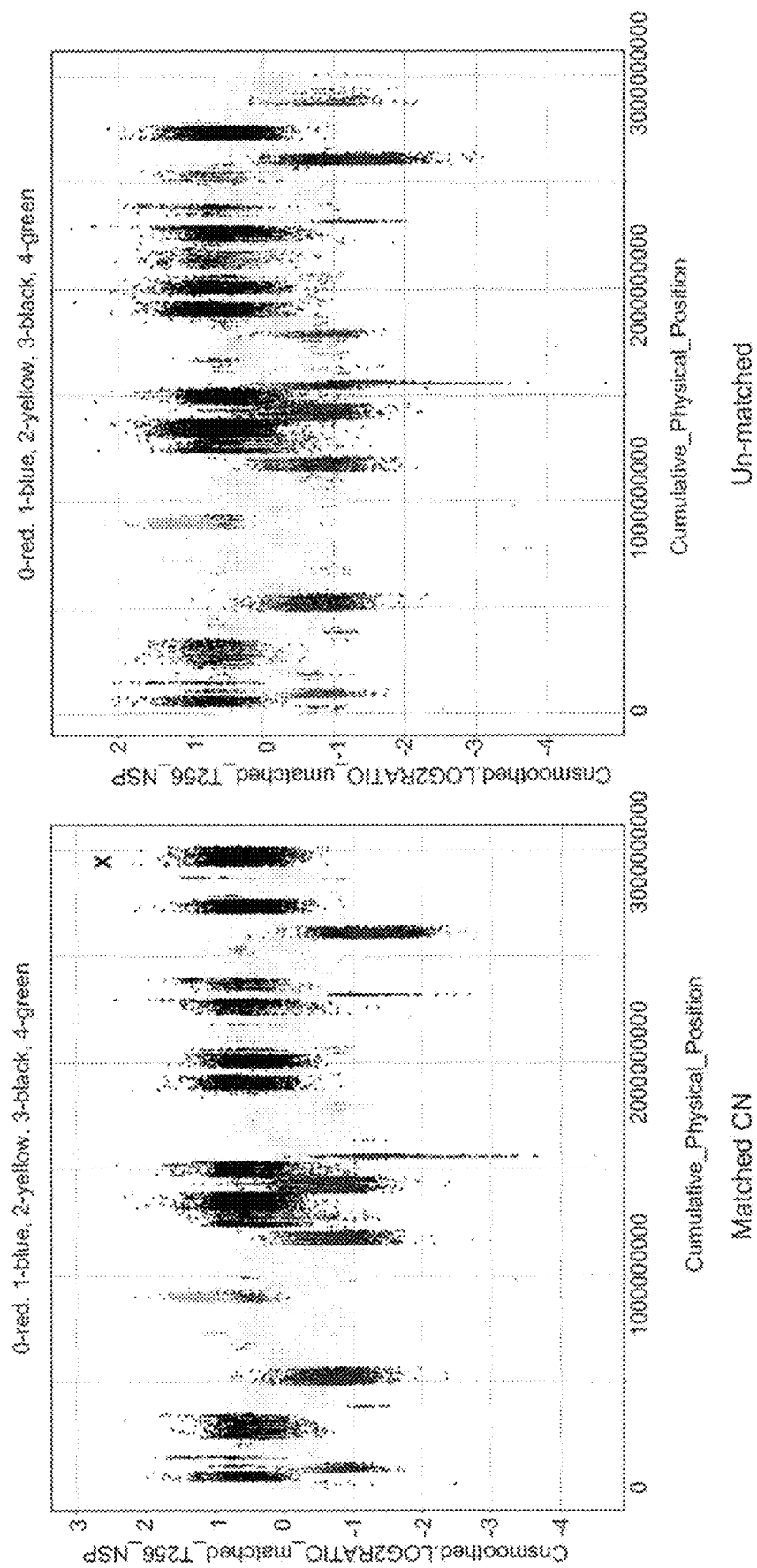
FIG. 50 shows matched versus un-matched (using 27 normal 2X references) copy number analysis for ChrX.
Figure 51:
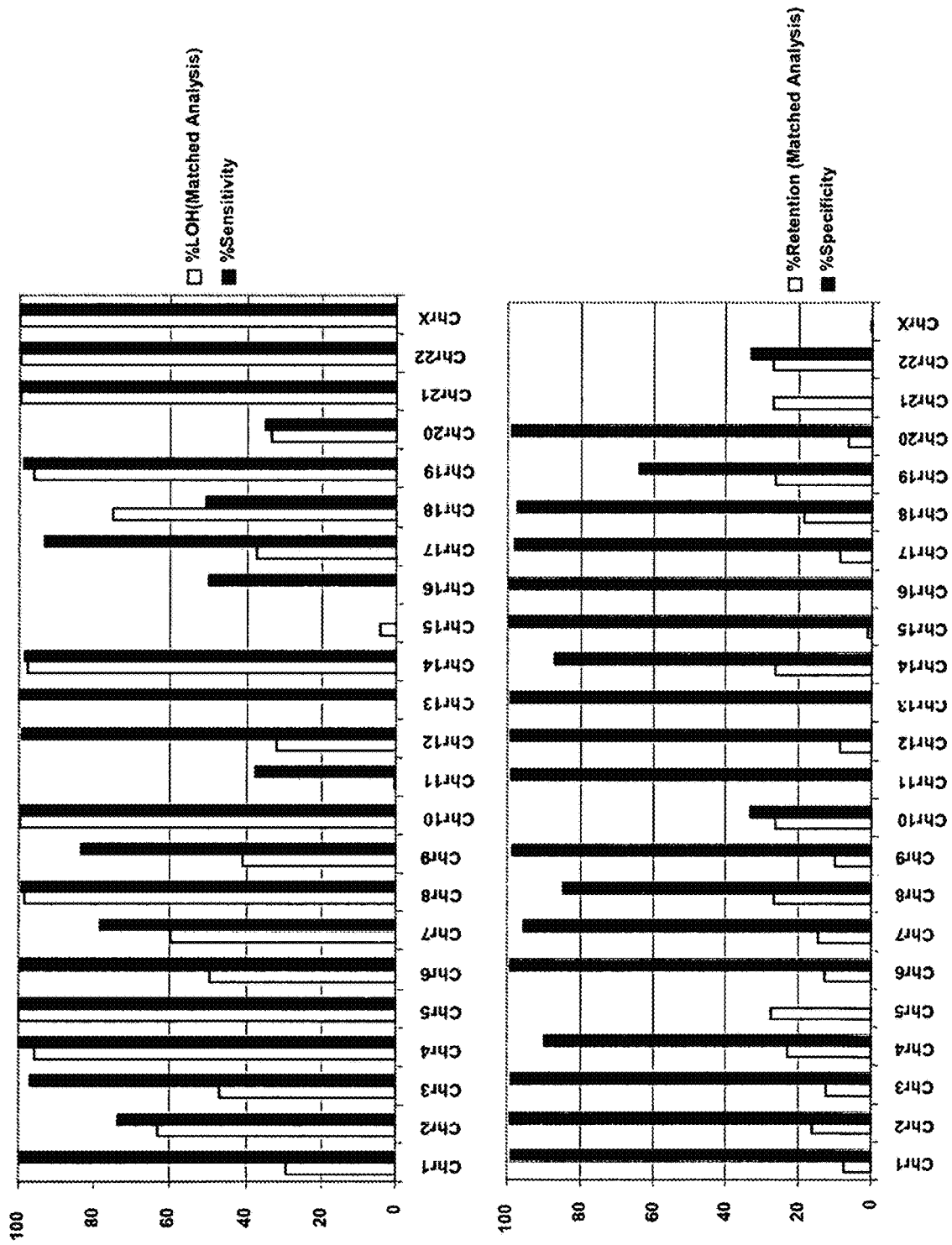
FIG. 51 shows bar graphs of percent LOH or retention for each chromosome.

FIG. 50 shows matched versus un-matched CN analysis for ChrX. Matched is shown on the left and un-matched using 27 normal 2X references is shown on the right.

The underlying data normalization includes (1) intra and inter array quantile normalization, (2) an allele-specific cross talk correction and (3) normalization for PCR correction. The accuracy of delineating change-points, where change points correspond to switching in copy number states, is enhanced by adopting a Hidden Semi-Markov framework where the duration density for the SNPs in each of the states can be explicitly modeled. LOH and aberrant CN regions are derived from both paired (tumor-normal) and unpaired samples. The analysis correlates the association and the extent of localization of the ASCN and LOH changes. Estimation of LOH changes is possible via an ethnicity matched or unmatched and family matched or unmatched manner.

Generation of a virtual global reference for CN estimation. First, Probe-level quantile normalization of SNP data sampled randomly from normal female(2x) experiments. Based on the available number of experiments, a minimum number of samples need to be considered to mitigate "noise" spikes introduced by copy number polymorphisms or other unexpected CN variations in normals. The minimum can be estimated by testing for convergence of the distribution post-quantile normalization as a function of number of samples. (prototype). Second, the above process can be further optimized by performing a 1-versus all correlation of all reference datasets and filtering out all reference files with a) a median distribution <x %; b) maximal inter-quartile range (IQR).(prototype). Third, following steps 1-2 a probe-level median distribution is considered as the virtual, global reference. Fourth, a combination of steps 1-3 provides a dynamic method for generation of a global reference. Fifth, a step which combines user selection of source reference datasets in combination with step 3 is a variant on the implementation.

Normalization details for CN estimation: First, Allele specific cross-talk correction, second Polymerase chain reaction (PCR) correction—A PCR fragment length and GC content based regression. Methods of copy number estimation using genotyping arrays that take into consideration fragment length and GC content have been described previously. See, for example, Redon et al., Nature 444:444-58 (2006), Komura et al., Genome Res. 16:1575-84 (2006), Freeman et al., Genome Res. 16:949-61 (2006), and Nannya et al., Cancer Res. 65:6071-9 (2005).

Data Smoothing for CN estimation. There are three modes of data smoothing (a) Gaussian, (b) Lowess and (c) Spline. A) In case of the gausssian smoothing, the smoothing bandwidth can either be provided by the user or computed dynamically. The latter entails the following: 1) Ordering of the interSNP distance on a per chromosome basis;2) Exclusion of the centromere unless the chromosome is acrocentric.3) The chromosome-level bandwidth is the mode of the distribution. 4) The overall bandwidth applied across the dataset is the mode of the chromosomal bandwidths.5) Step1-4 have been prototyped, but the user settable bandwidth is the one that has been implemented in the commercial software.

In some aspects spline smoothing is used. Spline smoothing is quite optimal for this type of data, where the degrees of freedom for the fit are updated dynamically, by estimation of Copy Number via a chromosome X titration experiment.

Single Sample Workflow

The workflows discussed here indicate a two-sample mode—which is the mode in the current implementation of the commercial software. The algorithmic discussions are equally applicable to a one sample mode, where the reference is detected in the tumor/test sample itself. In the one-sample mode, the reference is comprised of all autosomal clusters in the chromosome which can either be segmented based on FISH data or a change point analysis—most appropriately, a Hidden Semi Markov Model (HSMM)—of the signal intensity of the SNP data. This will allow a user to perform a single sample per experiment, but can also enable the generation of replicates—allowing multiple and independent testing of the same hypothesis.

Chromosome copy number analysis using whole-genome expression and genotyping microarray technology is fundamentally improving our understanding of human disease. The computerized methods and computer software products disclosed are particularly useful for analyzing the copy number of genomic regions using hybridization data obtained from high density genotyping or gene expression arrays. In particular the methods and computer software products will be described using exemplary embodiments in the context of copy number analysis using SNP genotyping arrays that allow genotyping of more than 10,000, more than 100,000 or more than 500,000 human SNPs using a single array or array set. In particular, the Affymetrix Whole Genome Sampling Assay in combination with arrays of allele specific probes, for example, the GeneChip® Human Mapping 10K, 100K Set, 500K Set, SNP 5.0 and SNP 6.0 products, may be used with the disclosed methods of analysis and software methods to estimate allele-specific copy number alterations, loss of heterozygosity (LOH), and genotypes in a single experiment.

Methods for determining copy number using high density SNP genotyping arrays, for example, Affymetrix SNP genotyping arrays (including the 10K, 100K, 500K, SNP 5.0 and SNP 6.0 products) are disclosed. The Affymetrix mapping assays use a WGSA target preparation scheme in which single primer PCR amplification of specific fractions of the genome is carried out. The 100K WGSA method uses two separate restriction enzymes that each generates a complexity fraction estimated to be about 300 Mb. The 10K array uses a single restriction enzyme and generates a sample with less than 300 Mb complexity. Both arrays have been shown to genotype SNPs, with call rates, reproducibility, and accuracy greater than 99%, 99.7%, and 99.7% respectively (Matsuzaki et al. *Nat Methods* 1: 109-111, 2004) and Matsuzaki et al., *Genome Res.* 14:414-25 (2004). The 500K products also use a two restriction enzyme approach.

Genetic instability, such as changes in DNA copy number, is one of the hallmarks of many human cancers. High-density DNA array technology has been applied towards the identification of genomic alterations in tumor cells, most notably loss of heterozygosity (LOH) (Lindblad-Toh, et al. (2000), *Nat Biotechnol, Vol.* 18, pp.1001-5, Mei, R., et al. (2000), *Genome Res, Vol.* 10, pp.1126-37, Schubert, et al. (2002), *Am J Pathol*, Vol. 160, pp.73-9, and Dumur et al. (2003), *Genomics*, Vol. 81, pp.260-9). Methods are disclosed for using high density arrays for detection of LOH and genomic amplifications and deletions. In many embodiments the high density array is a genotyping array. However, other arrays of probes may be used, for example, an array of probes complementary to different regions of human genes, such as the Human Genome U133 Plus 2.0, available from Affymetrix, Inc, Santa Clara may be used. In general the methods compare the intensity of hybridization of nucleic acids to perfect match probes and correlate higher intensity with higher copy number. The relationship between log intensity and log copy number was found to be approximately linear and using control samples of known copy number the slope and y-intercept of the line may be estimated.

Methods of genotyping many polymorphisms in parallel may be used to identify DNA gains and losses across multiple chromosomes. Methods that reduce complexity of a genomic sample in a predictable way can be used in combination with an array of probes designed to interrogate polymorphisms in the resulting reduced complexity genomic sample. Methods such as those disclosed in U.S Patent Pub. No. 2004-0067493 may be used to detect genotypes and the genotype information may be used to identify regions of homozygous deletion or regions of amplification. A single primer may be used to amplify representative fractions of the genome followed by SNP genotyping via hybridization to high density oligonucleotide arrays which comprise perfect match (PM) and mismatch (MM) probe sets from one or both strands of the DNA. Algorithms that use, for example, discrimination ratios between paired PM and MM intensity values may be used to identify regions of homozygous deletions or median PM intensities may be used to identify regions of gene amplification. Following chip intensity normalization, SNP discrimination ratios and PM intensities from an experimental sample may be compared to distributions derived from a references set containing normal individuals. In one embodiment the sample set contains over 10, 100, 400, 500, or 1,000 individuals, allowing statistically significant regions with DNA copy number changes to be identified.

Additionally, statistically significant genomic intervals showing loss of heterozygosity (LOH) may be identified by calculating the likelkhood of a contiguous stretch of homozygous markers based on known allele frequencies. The SNPs are SNPs that are genotyped on the array being used and there may be SNPs in between the genotyped SNPs that are not genotyped. The allele frequencies may be obtained, for example, from a publicly available database, such as dbSNP, by genotyping a reference set of samples, or from any available database of allele frequencies. Using a data set derived from a single array, a sample can be analyzed for LOH, deletions, and amplifications. In one embodiment an array that has mean and median inter-SNP distances of about 250 kb and 120 kb respectively may be used. In another embodiment the mean and median inter-SNP distances are less than 100 kb and 20 kb respectively. This method may be used to detect copy number changes in any sample. In a preferred embodiment the tissue is a tissue that is suspected of being a cancerous tissue, for example, human breast cancer, prostate cancer, lung cancer and colon cancer.

Methods are disclosed for identifying chromosomal gains and losses at high resolution using high-density microarray genotyping methods such as whole genome sampling analysis (WGSA) (see, Kennedy et al. (2003), *Nat Biotechnol*, Vol., pp.1233-1237, and U.S. Pat. No. 6,548,810, 2002-0142314, 2004-0146890, 2003-0186279, 10/442,021 (not published), 20040072217, 2003-0186280, and 20040067493 and U.S. Pat. No. 6,361,947). WGSA simultaneously genotypes more than 10,000 SNPs in parallel by allele-specific hybridization to perfect match (PM) and mismatch (MM) probes synthesized on an array. Methods for chromosomal copy number analysis using the Affymetrix Mapping 10K array in combination with WGSA, have also been reported in Bignell et al. *Genome Res.* 14:287-295 (2004) and Huang et al., *Hum Genomics* 1:287-299 (2004). Similar analysis using the Affymetrix Mapping 100K array has also been reported in Slater et al., *Am. J. Hum. Genet.* 77:709-726 (2005). WGSA methods and applications of WGSA and mapping arrays are disclosed in, for example, U.S. Patent Pub. Nos. 2004-0185475, 2004-0157243, 20040146890, 20030186279, 20030232353, 20030186280, 2003-0186280 and 2004-0067493 and U.S. Pat. No. 7,097, 976. and in U.S. Patent Application Nos. 60/456,206 (not available), Ser. No. 10/646,674 (not published) and Ser. No. 10/442,021 (not published), each of which is hereby incorporated by reference in its entirety for all purposes.

Novel algorithms that use probe intensity information to infer copy number in an allele-specific manner from high density DNA oligonuceotide arrays designed to genotype over 100,000 SNPs, are disclosed. Individual probes for each SNP are tested for the ability to support an allelic dosage response using a set of normal individuals. Total and allele-specific copy number estimations were independently evaluated for a subset of SNPs using quantitative PCR and TaqMan reactions with several human cancer cell lines. The sensitivity and specificity of the algorithm were characterized using DNA samples containing differing numbers of X chromosomes as well as a test set of normal individuals. The copy number algorithm allows for allele-specific output, and when coupled with SNP genotype calls from the same array, provides additional detail into the structure of genome wide alterations that contribute to allelic imbalance.

Any method of complexity reduction that results in the amplification of a predictable subset of fragments may be used to produce a reduced complexity sample. The array may be designed depending on the complexity reduction method being used and the fragments predicted to be present in the reduced complexity sample. Other methods of complexity reduction include, for example, AFLP, see U.S. Pat. No. 6,045,994, which is incorporated herein by reference, and arbitrarily primed-PCR (AP-PCR) see McClelland and Welsh, in *PCR Primer: A laboratory Manual*, (1995) eds. C. Dieffenbach and G. Dveksler, Cold Spring Harbor Lab Press, for example, at p 203, which is incorporated herein by reference in its entirety. Additional methods of sample preparation and techniques for reducing the complexity of a nucleic sample are described in Dong et al., *Genome Research* 11, 1418 (2001), in U.S. Pat. Nos. 6,361,947, 6,391,592 and 6,872,529, 6,958,225, 6,632,611, and 6,872, 529, and US Patent Pub. No. 2004-0067493 which are incorporated herein by reference in their entireties.

Amplification methods may be optimized to amplify a subset of these fragments, for example, the fragments that are 400 to 800 basepairs. An array may be designed to detect the presence or absence of the fragments that are predicted to be amplified under a selected set of fragmentation and amplification conditions. The probes on the array may be designed to hybridize to selected regions within each fragment. One or more probes may be designed for each fragment. The probes may be optimized for hybridization using empirical criteria (see, for example, U.S. Patent Pub. No. 2003-0096986 which is incorporated herein by reference in its entirety). Different arrays may be designed depending on the method used to generate the reduced complexity sample.

Prior to hybridization the fragments in the reduced complexity sample may be labeled. In another embodiment the fragments are further amplified prior to hybridization. In some embodiments the fragments are DNA and RNA is synthesized from the fragments and hybridized to an array.

In another embodiment a reduced complexity sample is hybridized to an array that is designed to interrogate all regions of a genome. Probes may be positioned uniformly throughout the genome for example 1 probe approximately every 100, 200, 1000, 2500, 10,000, or 100,000 bases.

In one embodiment the sample is hybridized directly to an array without reducing the complexity of the sample prior to hybridization. The array may be designed to detect the presence of absence of all regions of the genome using representative probes for each region of the genome or to detect selected regions of the genome.

Homozygous deletions of certain genes, for example, tumor suppressors, are known to be tumorigenic. Homozygous deletion of p53 is known to be associated with a variety of tumor types. Amplification of certain genes, for example, oncogenes, may result in overexpression of the genes which may be tumorigenic. Examples of oncogenes that are amplified in various tumors include c-myc, c-abl, c-myb, c-erbB, c-K-ras, and mdm2, see Genes VI, B. Lewin (1997) at 1144, which is incorporated herein by reference in its entirety. The method may be used to identify new homozygous deletions that are associated with cancer or another disease or phenotype. In another embodiment the method may be used to determine if an experimental sample has one or more homozygous deletions known or thought to be associated with cancer or another disease or phenotype.

Homozygous deletion of chromosomal regions are also known to cause other disorders, for example, male hypogonadism (Gromoll et al. *J Clin Endocrinol Metab* 85: 2281-2286, 2000), late onset muscular dystropyn (Pulkkinen L, et al., *Hum Mol Genet* 1996:5(10):1539-1546). Homozygous deletions have also been shown to have beneficial phenotypes such as protection against parenteral HIV-1 infection, see Kupfer et al. AIDS, June 18; 13(9):1025-8, 1999.

The gene-dosage techniques disclosed may be applied to measure gene copy number for a variety of diseases and applications. In addition to cancer, large genomic duplications and deletions have been found in association with diseases such as alpha-thalassaemia and Duchenne and Becker muscular dystrophies, see, for example, Armour et al. *Human Mutat* 20:325-337 (2002). The method may be used to identify a variety of chromosomal anomalies including, for example: constitutional, acquired, numerical, structural, and mosaicism. A constitutional anomaly affects the individual throughout. The chromosome error was present in the embryo. It may occur before fertilization or in the fertilized zygote. Such disorders include, chromosome inborn syndromes, such as trisomy 21, Turner syndromes, and others. Acquired anomalies affect only one organ with the other tissues being normal, such as cancer. The terms "constitutional" and "acquired" are really quite general terms, and can be applied to any persistent change encountered in clinical practice. A chromosome anomaly may also be homogenous, having all the cells studied carrying the anomaly. Normal cells may be present but not assayed. When only some cells carry the anomaly and others are normal (or carry another anomaly) the sample or individual is a mosaic. Individuals may also have numerical anomalies where one or more chromosomes are present in numbers that are different from normal. Structural changes may occur within a chromosome. The change may be balanced, if there is no loss or gain of genetic material, or unbalanced, if there is deletion and/or duplication of chromosome segment(s).

In another embodiment one or a few PM probes are used for detection of amplification or deletion. In one embodiment there are 40 probes that hybridize to the region of a SNP and are used for genotyping the SNP. The probes that work well at discrimination between specific and non-specific hybridization are used for gene dosage analysis using a genotyping array. The probes to be used may be selected by empirical performance of the individual probes. Probe behavior may be analyzed empirically to identify probes that give the most discrimination and highest signal. For Probe Specific Models see Li, C. and Wong, W. H. (2001) *Genome Biology.* 2(8): research0032.1-0032.11, Li, C. and Wong, W. H. (1998) *Proc Natl Acad Sci* USA. 98:

31-36 and Mei, R. et al. (2003) *Proc Natl Acad Sci* USA. 100: 11237-11242. In another embodiment change point analysis is used. For methods of using Change point analysis see Olshen, A. B. and Venkatraman, E. S. (2002). *Proceedings of the Joint Statistical Meetings*, Sen, A. and Srivastava, M. S. (1975). *Ann Statist*. 3 98-108 and Yao, Y-C. (1988) *Statistics & Probability Letters*. 6 181-189. In some aspects of the invention, computer software products and computer systems are provided to perform the methods (algorithms) described above. Computer software products of the invention typically include computer readable medium having computer-executable instructions for performing the logic steps of the method of the invention.

Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Computer systems of the invention typically include at least one CPU coupled to a memory. The systems are configured to store and/or execute the computerized methods discribed above. Basic computational biology methods are described in, e.g. Setubal and Meidanis et al., Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001).

There is a known correlation between carcinogenesis and genetic alterations in tumor cells. Genetic alterations include, for example, activation of oncogenes such as c-myc and c-erbB-2, and mutation of tumor suppressor genes such as p.53 and Rb. The genetic alteration events often involve allelic imbalances including gross chromosomal aberration (i.e. aneuploidy, deletions and amplifications), microsatellite instability and loss of heterozygosity, long stretches of which are often associated with deletions. Location and exploration of these alteration events will be critical to understanding the genetic basis of many diseases. Deletions may be, for example, partial chromosome deletions, micro-deletions of several kb or less to macro-deletions of entire chromosomes. Amplifications may be, for example, partial chromosomal amplifications, gains of a single copy of an entire chromosome or gains of multiple copies of a chromosome. Translocations generally comprise parts of a particular chromosome being translocated to another chromosome.

Methods for estimation of copy number and for detection of loss of heterozygosity (LOH) are disclosed, including workflows, algorithms, and data analysis methods. Each of the copy number and LOH algorithms supports either a workflow where the tumor and normal samples are obtained from the same person and is referred to as a matched (or paired) workflow or a workflow where the test sample is compared to a pooled set of normal references and referred to as an unmatched (or unpaired).

In one aspect there are 4 workflows: 1. matched (sample) Tumor-Normal Copy Number, II. Matched (tumor-Normal) LOH (without associated CN), III. Un-matched copy number, IV. Un-matched LOH (without associated copy number).

Mathematically, the process consists of generating a distribution of $\log_2$ ratios of the SNPs where an abnormal or test sample is compared to that of normal samples(s). This is used to generate a raw CN distribution across the genome. The information can be plotted with the genomic coordinate or location in the genome on the X-axis versus the copy-number distribution on the y-axis. The CN estimation problem thus amounts to finding change points in the distribution along the genomic position axis, such that SNPs or portions of the genome implicated in a change arising from the abnormality induced in the cells can be identified. An example of such a plot is shown in FIG. 1.

In the CN distribution shown in FIG. 1, state 2 [101] is referred to as the normal or copy-neutral region. The state is referred to as "2" because the sample has at that region a CN state of 2 or 2 copies of a chromosome. Since the reference is presumed to be diploid as well, its copy number state is 2. Therefore State 2: $\log_2$(sample CN state=2/reference CN state=2)=0.0. In case of a homozygous deletion, the sample has lost both copies of the chromosome and therefore is in CN state 0: $\log_2$(10e-10/2) approaches—infinity or more realistically approaches $-3$. For a hemizygous deletion, the sample has a single copy loss and is hence in CN state=1: $\log_2$(sample CN state=1/reference CN state=2)=$-1$. State 1 is represented by [105]. For a single copy gain, the sample has a single copy gain and is hence in CN state=3: $\log_2$ (sample CN state=3/reference CN state=2) is ~0.58. For multiple copy gains (example: 2 copy gain) the sample is in CN state=4: $\log_2$(sample CN state=4/reference CN state=2) is ~1. See [103].

To generalize the number of states in the HMM (for Copy Number specifically), the HMM is set up as a multi-state model, where the number of underlying states are determined dynamically from the sample. This determination of states can be performed in several ways, for example: via k-means clustering; or optimization via the Akaike and/or Bayesian Information criterion parameters. See Akaike, pages 267-281 in Second Annual Symposium on Information Theory (B. N. Petrov and F. Csaki, eds.). Akademi Kiado, Budapest,1973 and Alfaro and Huelsenbeck Syst. Biol. 55(1):89-96 (2006).

In a preferred embodiment the CN-HMM is implemented as a 5-state model in a Microsoft Windows based implementation. In another software implementation based on linux (command-line), the HMM is implemented as a multi-set model, where the user can set the total number of states in advance, but the software does not dynamically ascertain the total number of states.

In another aspect, LOH is also implemented as an HMM with only 2 states, namely LOH and retention of heterozygosity or normal state.

An overview of the various algorithmic components of CN and LOH estimation is outlined as follows. The methods relate to estimation of copy number (CN) and loss of heterozygosity (LOH). The methods include workflows, algorithms and data analysis methods that include: (a) probe filtering, (b) quantile normalization or median scaling plus RMA, (c) reference generation either specific or global, (d) PCR normalization, (e) estimation of total copy number (TCN) including allele cross talk correction, (0 virtual array, (g) Gaussian smoothing plus bandwidth estimation, and (h) HMM: basics plus parameters plus parameter tuning At the general level the different aspects of the algorithms include: 1) Probeset Filtering: At the fundamental level only perfect mathc probes are considered; 2) Probe level normalization including either quantile or a linear median scaling; 3) Normalized probe intensities are summarized in a SNP and allele specific manner using RMA (robust multi-array method) which employs a median polish at its core;

4) Since copy number of a reference(test) sample is estimated with respect to a normal reference—a reference needs to be provided for this analysis. In case of the matched (or paired) tumor-normal tissue-pair the normal tissue contitutes the specific reference for the analysis. In case of the un-matched analysis, a global reference is generated virtually from a pool of normal references. The exact methodology of this is discussed in the 'Global Reference; section.

5) Based on prior research it is known that one of the sources of error in CN estimation is introduced by variation in the PCR hybridizaton. The PCR normalization methodology using GC content and PCR fragment length (on which the SNP resides) as the covariates was developed at the Univ of Tokyo labs of Dr. Aburatani & Dr. Ogawa. Basically this falls in the category of intra-array normalization. The details of the method have been discussed in the 'PCR normalization' section.

Two different methods of Total copy number (TCN) estimation are disclosed herein. In this context, the method of allele x-talk correction has been elucidated. The allele x-talk correction comprises another level of CN normalization, one that is not addressed by the PCR normalization method. This can be characterized as intra-array normalization.

Figure 23:
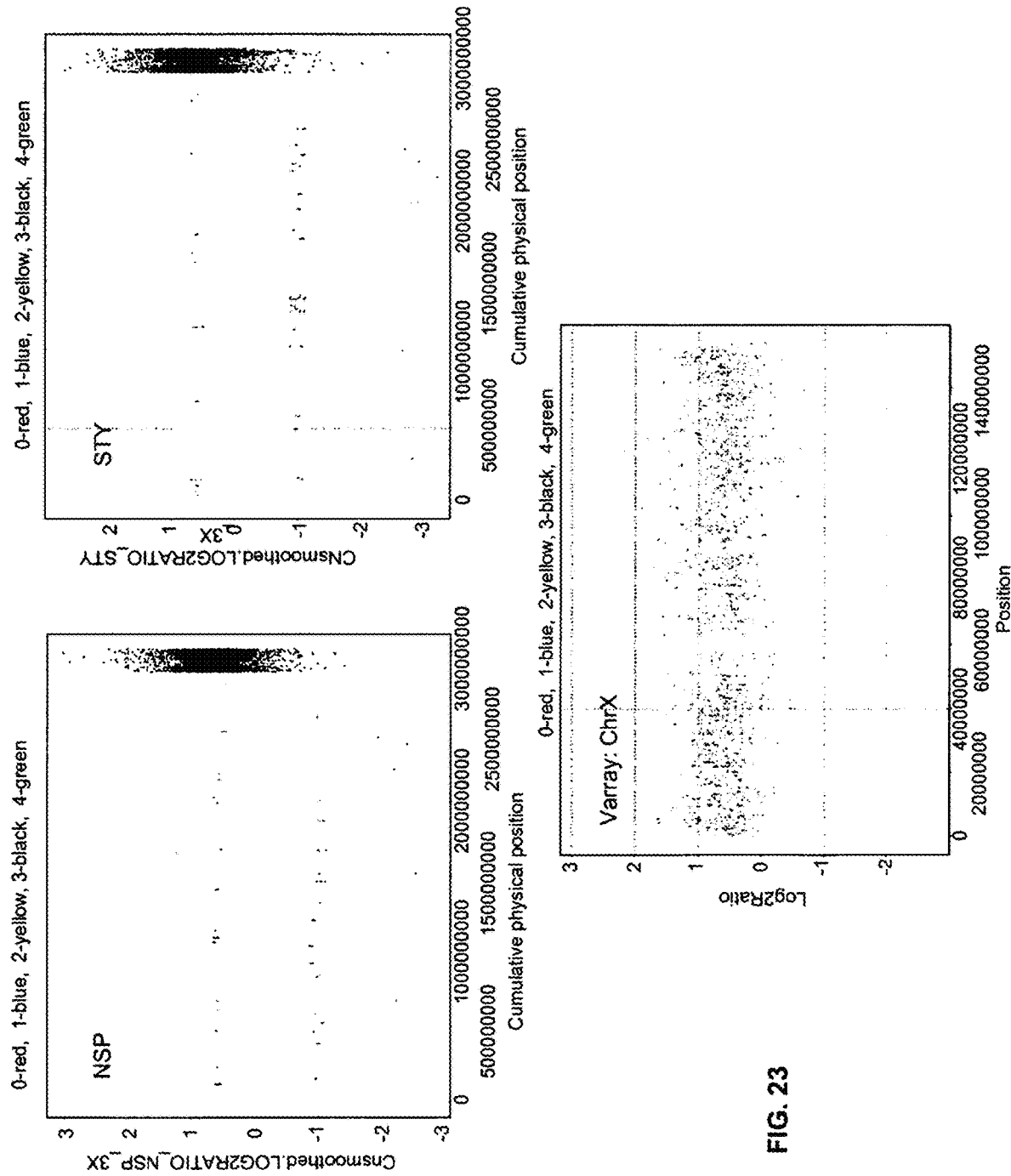
FIG. 23 shows application of the virtual array to the X chromosome (lower panel) with NSP and STY arrays shown in the upper panels.
Figure 24:
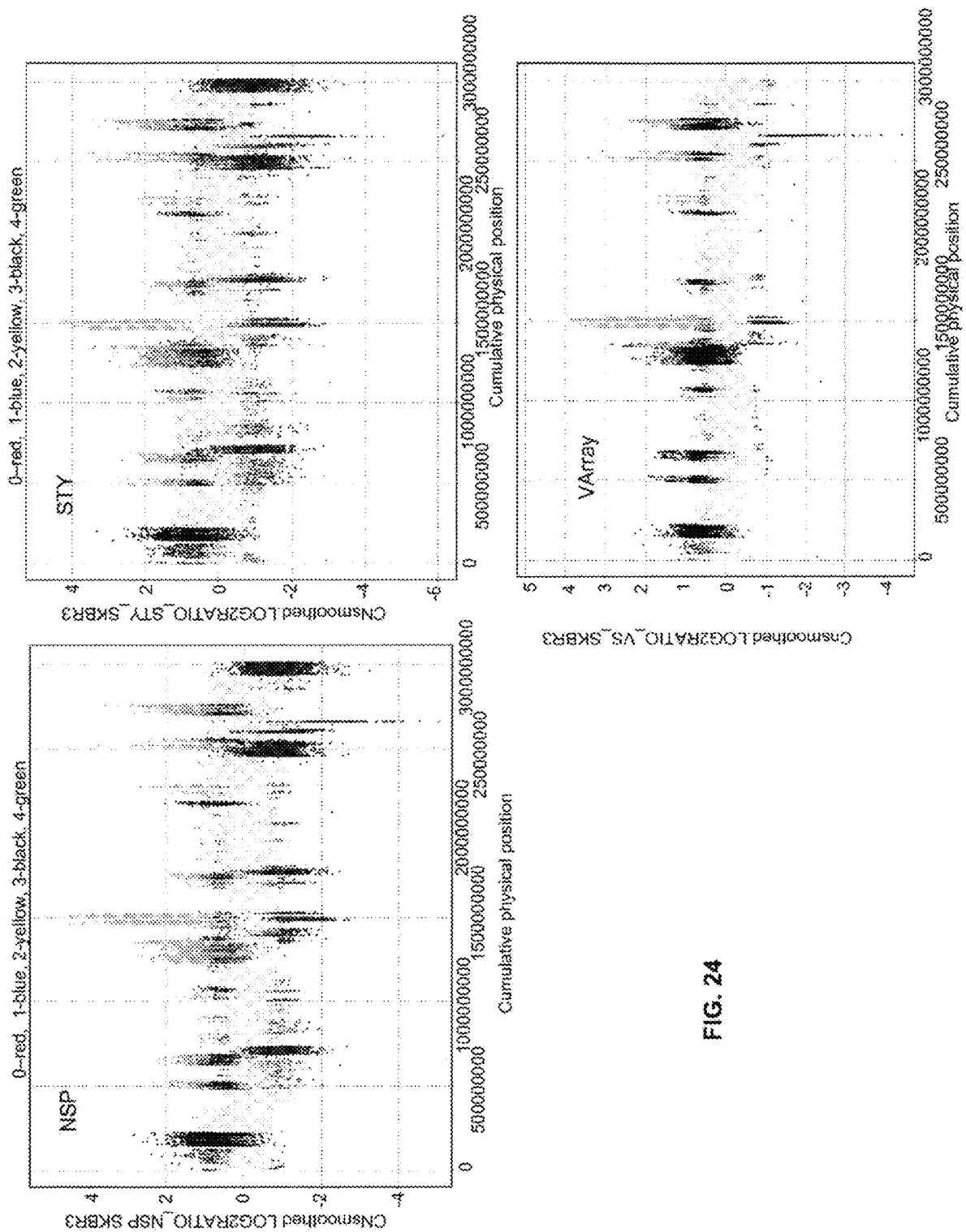
FIG. 24 shows virtual array data for a breast cancer sample.

The generation of the virtual array constitutes the mechanism of combining data from two or more arrays (computationally) to create a single virtual array. This method includes an inter-array normalization to adjust for the noise floor and variance across n arrays. Without the inter-array normalization, there is a high probability of certain regions of the genome being erroneously labeled as CN aberrations. The is also a form of inter-array normalization. The arrays to be combined are preferably of the same type; for example, two 50K mapping arrays may be combined to create a 100K virtual array. The method includes an inter-array normalization to adjust for the noise baseline and the variance across the arrays. Without the inter-array normalization, there is a higher probability of certain regions of the genome being erroneously labeled as CN aberrations. The normalization parameters may be estimated based on a subset of SNPs in the copy-neutral region (CNR). FIG. 23 shows application of the virtual array method to the X chromosome (lower panel). FIG. 24 shows virtual array data for the breast cancer sample SK-BR-3. The HMM parameters used are as follows: transition decay is 10-9, sigma is 0.3 and priors are equal. The NSP virtual array median LR per state R~0.91 and state R~0.80 for the STY virtual array the median LR per sate has R~0.88 and state has R~0.77.

In a preferred embodiment, CNR is bounded by the hemizygous deletion state (CN=1) at the low end and a single copy gain state (CN=3) at the high end. When the bounds are defined in this manner the following should be taken into consideration. First, since CN states 1 and 3 are equivalent to -1 ($\log_2(1/2)$) and 0.58 ($\log_2(3/2)$) respectively, the bounds are asymmetric with respect to 0. Second, a deletion or single copy gain state may actually represent a median value different from (compressed relative to) -1 or 0.58. Therefore inclusion of all SNPs populating the region bounded by CN states 1 and 3 may include SNPs which are not copy neutral. As a result, instead of fixed boundaries for the CNR, it is defined in terms of two bounds: upper and lower. In the data presented, all analysis was performed by considering symmetric bounds of +/-0.2, but the bounds are adjustable.

The underlying normalization constitutes a shift-and-scale transformation, where the corrected log2ratio for SNPi in sample S($A_i^{Si}$) is shifted by the mean of the SNPs in the CNR (Equation 6) and is scaled by the variances of the arrays, as determined from the CNR (Equation 7). Equation 8 represents $A_i^{Si}$. Post normalization, SNPs are merged across both arrays and sorted based on chromosomal and physical location.

$$\mu_s = \text{average}(^cA[CNR[-],CNR[+]])_s \qquad \text{Equation 6}$$

$$\sigma_s = \text{stdev}(^cA[CNR[-],CNR[+]])_S \qquad \text{Equation 7}$$

$$A_i^{1_1} = (\sqrt{\sigma_2}/\sqrt{\sigma_1})(^cA_i^1 - \mu_1) \qquad \text{Equation 8}$$

Where CNR[+] is the copy neutral region lower and upper bounds and S is the sample.

In some embodiments Gaussian smoothing is performed prior to computing the final CN estimate and HMM segmentation. Smoothing increases the signal to noise ratio in the data and enhances the demarcation between regions of CN change. The degree of smoothing is often governed by the experimental question being addressed, especially the genomic footprint of the aberrations being detected. Filters that may be used, include Gaussian, spline and lowess. Gaussian smoothing may be referred to as an explicit filter since the HMM inherently performs a smoothing operation.

If Gaussian smoothing is performed it is possible for the user to set a smoothing bandwidth or the algorithm can dynamically determine a smoothing bandwidth based on the distribution of SNP frequency. Hence the algorithmically determined bandwidth would be specific to array-sets, where a 50K or 100K or 250K or 500K constitutes an array set.

Smoothing may be performed on the PCR normalized (and inter-array normalized when virtual arrays are being used) CN data. It may be performed for every index SNPi by considering the CN contributions from all flanking SNPs encompassed in a window (W), as defined by:

$$W \approx 2 * \sigma_{mult} * \sigma$$

Here $\sigma$ corresponds to the Gaussian bandwidth and $\sigma_{mult}$ is the sigma-multiplier. Specifically, all flanking SNPs within the bounds defined by $\sigma_{mult} * \sigma$ to the left and right of $SNP_i$ are considered. Note that $\sigma_{mult}$ is a user defined number but may be set to a fixed default value of, for example, 2. The default of 2 is comparable to the full-width-at half-maximum of the filter.

Figure 56:
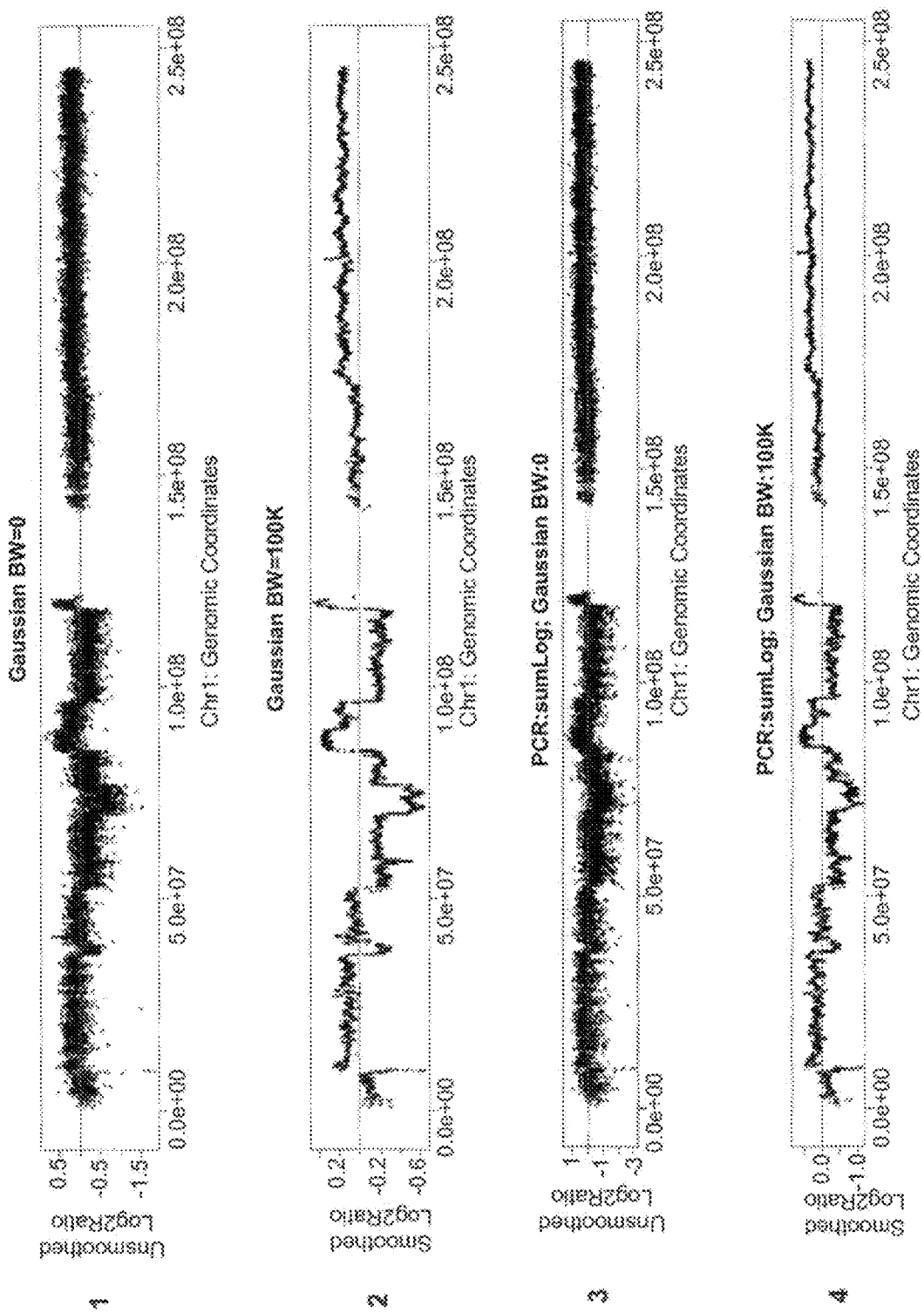
FIGS. 56 and 57 shows the effect of Gaussian smoothing.
Figure 57:
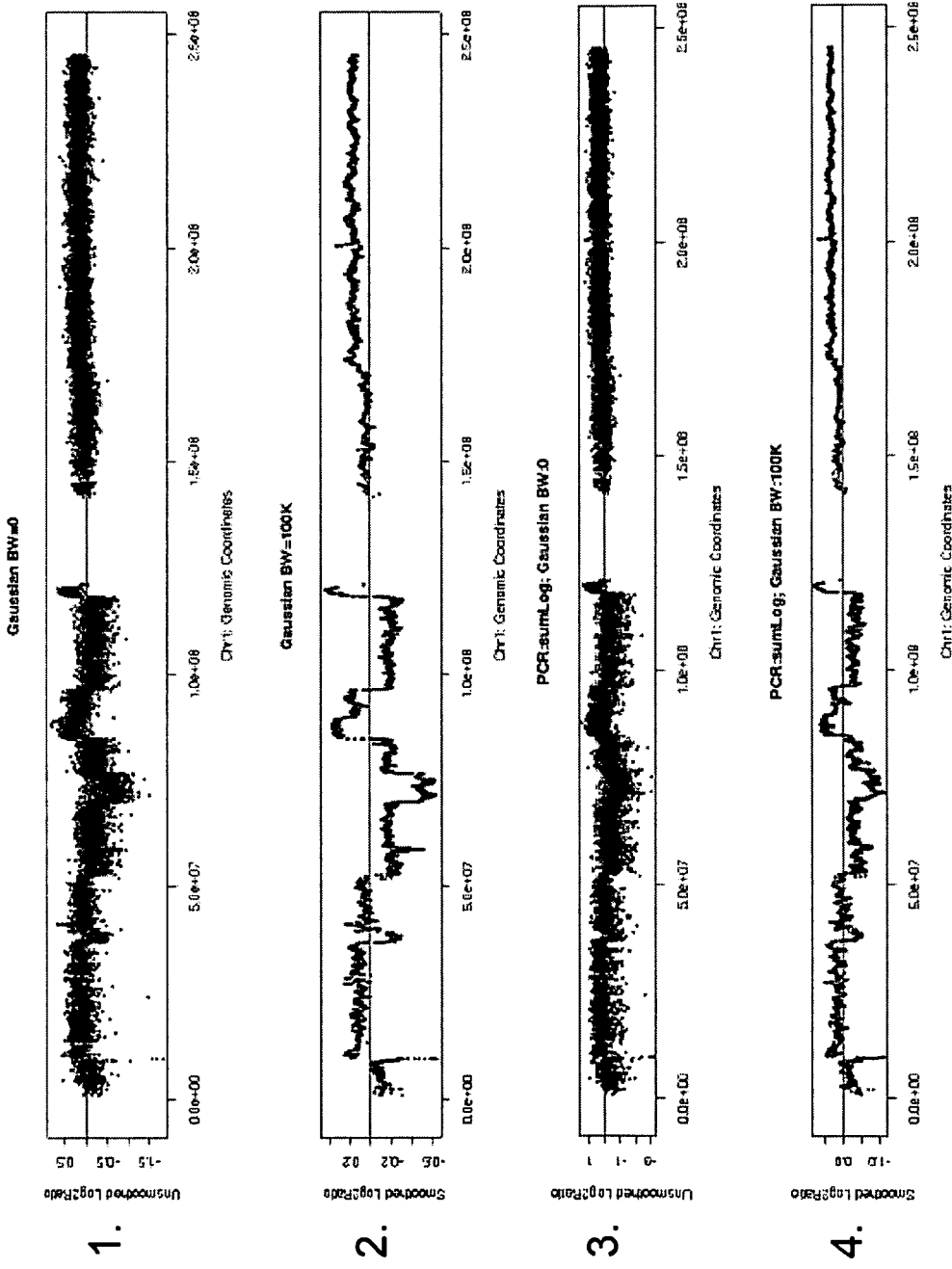

The choice of bandwidth affects the level of variance (noise) reduction obtained in the data. FIGS. 56 and 57 shows log 2ratio data with, °=100Kb, and without, °=0 smoothing, Panel 1 and 3 are unsmoothed and panels 2 and 4 are smoothed. The smoothing operation preserves the overall trend in data, but the level of smoothing may mask micro aberrations and a smaller sigma (less than 100 KB) may be used in some cases. When the sumLog option, which is optimized for bias, is used Gaussian smoothing facilitates variance reduction. If sumLog is the operational mode, minimal smoothing of the order of 15 kB contributes significantly to improvement in signal to noise reduction. The modulation of sigma is interconnected with the modulation of the HMM parameters, specifically the standard deviation discussed below. Table 2 provides a summary of suggested HMM standard deviation as a function of Gaussian bandwidth.

A Hidden Markov Model based smoothing and segmentation of regions of the genome into different copy number states has been implemented. The underlying assumption in a HMM model is that the experimental observation, CN or LOH value of a SNP, for example, is generated by a hidden or unknown process. Emitted or experimentally observed CN values, which may generally be a continuum, provide an estimate of the true, hidden copy number states. The copy number state is a discrete value. In a preferred embodiment, the HMM has 5 hidden states representing the following biological phenomenon: homozygous deletion of CN state=0; hemizygous deletion (haploid) or CN=1; copy neutral (diploid) or CN=2; single copy gain or CN=3; amplification (multiple copy gain) or CN≥4.

According to the HMM, a SNP, can exist in any one of the 5 hidden states (S). Based on the observed CN(0) of SNP, and its neighboring SNPs, as well as the model, λ (discussed below) the hidden state of the $SNP_i$ needs to be determined. A schematic is shown in FIG. 25. The number of hidden states in the HMM may be varied from the 5 state model of the present example. The same underlying HMM Model may be used for analysis of both paired and unpaired CN scenarios. A schematic of a 6 state ergodic HMM is shown in FIG. 26.

In a HMM approach it is assumed that a SNPi has a non-zero probability of existence in one of the states. The goal of the model is to determine the state which has the maximum likelihood of being the true underlying state of the SNP. Therefore the goal is to evaluate the probability of an observation sequence $\{O_1, O_2, O_3, \ldots O_\pi\}$ given the model λ. The three parameters of the model in one embodiment are: prior probability, transition probability and emission probability. The HMM parameters that may be varied relate to the above probabilities. User input values may constitute initial guesses or "seeds" for the parameters and are optimized by the underlying HMM algorithm.

In one embodiment, the discrete HMM of CN states are assigned based on the Viterbi algorithm, this being a global optimization method it is resilient to local CN perturbations. In addition to the smoothed (log2ratio) CN estimate provided on a per SNP basis, a HMM median CN estimate is also computed. This estimates the median CN for all contiguous SNPs belonging to a specific HMM state.

Since the HMM offers smoothing, it is possible to omit the gaussian smoothing completely prior to this. While the HMM is implemented as per the model described in Rabiner, there are several innovative aspects to the implementation details which will be outlined in the HMM section.

Prior probability (referred to herein as the prior or π) refers to the a priori knowledge of SNPi to exist in a preferred state. Under normal diploid conditions, the prior probability of a SNP to be in CN state 2 approaches 100%. However, since there are five states in this model (and in a probabilistic approach the assumption is that SNPi has a non-zero probability of being in any of the five states) the prior probability distribution for a diplose sample may be restates as follows: states $\{0, 1, 2, 3, 4\} \rightarrow \pi\{0.01, 0.96, 0.01, 0.01\}$. This implies that the prior probability of a SNP to be in state 2 is 96% (maximal) and to be in any one of the other states is 1% (minimal). The property governing the priors requires their sum across all states to be equal to 1 (equation 9). The priors are not assigned on a SNP by SNP basis, but to the population as a whole.

$$\sum_{s=1}^{S} \pi_s = 1 \text{ where } s = \text{states} \quad \text{Equation 9}$$

In a diseased condition where aneuploidy is a hallmark, the prior probability is significantly different from the above example and is not known a priori. In this case, it suffices to let the priors be equal for all states, for example, 0.2 where there are 5 sates, and let the algorithm adjust to determine the optimal prior per CN state. In general, it suffices to assume that no a priori information is available about the states of the SNPs and the prior for each state is initialized to be equal, or 0.2 for 5 state model.

The transition probability is the probability of transitioning from one hidden state, Si to another, Sj. In annotating CN aberrations, it is evident that a contiguous set of SNPs exist in a deletion state (micro-aberrations being an exception); in LOH, clusters of contiguous SNPs will generally exhibit loss so it is less frequent that a CN or LOH change effects a single SNP (singleton SNP effect). Often there will be a correlation across the hidden states of neighboring SNPs. In a first order HMM it is assumed that the hidden state of any SNP is impacted by the status of the prior SNP in genomic space, this introduces the concept of the probability of sustaining or transitioning from one hidden state to another. In this implementation an ergodic model is supported. According to this model, at any point both same-state or self-transitions as well as non self transitions are allowed. Hence, if SNPi exists in hidden state 0, then the allowed transitions for SNPSi+1 can be to any state from 0 through 4. If SNPi and SNPi+1 are proximal, then there is a high probability that the latter will continue to exist in state 0. Conversely if SNPi+1 were distal, then it may have increasing probability of transitioning to an amplification or copy-neutral state.

There is significant variation in the SNP density across the 10K to 500K SNP arrays from Affymetrix. For the Mapping 250K arrays the median inter-SNP distance is 2.5 kB. To reduce dependencies on the inter-SNP distances, the transition matrix is modeled as a non-stationary one as described in Equation 10. In this equation $$\hat{I}\times(e^{-B\Delta d})+\hat{\pi}(1-e^{B\Delta d}) \quad \text{Equation 10}$$

Where $\hat{\pi}$ refers to the prior matrix associated with the 5 states for CN or 2 for LOH; Δd refers to the inter-SNP distance and β refers to the transition decay parameter. The decay parameter input by the user may be β' where β'=1/β' and is represented in units of base pairs. A smaller β implies a slower transition from the current hidden state and vice-versa. The relationship is demonstrated by FIG. 31 which shows transition decay as a function of inter-SNP distance.

Emission probability reflects the probability with which the underlying state (S) is emitted to produce the observable (O). The two parameters that govern this probability are: the mean and the standard deviation (SD) of each hidden CN state. The SD which reflects the dispersion in each hidden CN state may be a user tunable parameter. In a preferred aspect it may be the only user tunable parameter. It sets an initial guess on the expected dispersion. If the CN data is smoothed, then the expected SD should be tight (low); if the data is noisy, the SD should be high. As a rule, the lower the bandwidth (implying that the underlying CN data is unsmoothed or noisy), the higher the SD parameter. Table 4 summarizes suggested SD as a function of bandwidth.

TABLE 4

HMM initial SD as a function of guassian bandwidth (σ)

| Band-width | logSum: SD states 0, 1, 3, 4 | logSum: SD state 2 | sumLog: SD all states |
|---|---|---|---|
| 0 | 0.25 | 0.19 | 0.5 |
| 15k | 0.15 | 0.13 | 0.46 |
| 30K | 0.12 | 0.09 | 0.36 |
| 50K | 0.11 | 0.08 | 0.28 |

TABLE 4-continued

HMM initial SD as a function of guassian bandwidth (σ)

| Band-width | logSum: SD states 0, 1, 3, 4 | logSum: SD state 2 | sumLog: SD all states |
|---|---|---|---|
| 100K | 0.09 | 0.07 | 0.20 |
| 500K | 0.06 | 0.03 | 0.16 |

To account for the difference in underlying variance in the data with the logSum versus sumLog methods different SD settings are preferably used. Generally, for the logSum option the SD of CN state 2 is tighter than those of the other states. These estimates are derived from a 1x to 5x chromosome X titration study on replicate datasets where inter-laboratory variability was also taken into consideration.

P-value estimation: A running t-test may be performed on the PCR-normalized CN estimate on a per chromosome/per sample basis. The null hypothesis is: the mean CN in a given window (W) is equal to the baseline CN. The baseline is computed per sample and the W corresponds to the Gaussian window size. In this embodiment, it is a windowed t-test, and therefore, p-values are not computed for unsmoothed data.

Allele-specific copy number is computed for paired experiments. In this embodiment, only the SNPS that are part of the subset of SNPs that have heterogeneous, genotype {AB} calls in the reference are considered. On average this encompasses about 30% of the SNPs. For this subset the PCR-normalized A and B allele data is transformed into min and max allele, based on their intensity. The ASCN analysis pipeline is analogous to the TCN pipeline described above where the min and max allele data are process independently.

LOH analysis in a preferred embodiment include generally the steps of SNP-level-filtering and HMM based segmentation for LOH. Unlike CN analysis the HMM applied for the paired and un-paired LOH are preferably slightly different. If the CN and LOH analysis are performed in a single analysis then an identical SNP filtering as described for CN analysis may be applied for LOH. This enables comparison of the CN and LOH status of the SNPs. The HMM for LOH uses a two-state model preferably: LOH or state 0 and retention of heterozygosity (normal) or state=1.

Unlike CN, the prior probability in LOH is estimated empirically from the sample(s)-specific genotype data. The paired LOH analysis is based only on the subset of SNPs that are heterozygous {AB} in the normal reference. It is therefore recommended that BRLMM, as opposed to DM, be used for generation of the genotype data, since the former recovers a significantly higher percentage of heterozygous calls. This is demonstrated in FIG. 35. The prior is estimated from the rate of LOH as computed in this tumor-normal SNP subset. Updates to prior, emission and transition probabilities (can be de-coupled). Transition decay parameters not updated. No EM optimization in LOH.

The un-paired analysis includes all SNPs. Here the prior is computed as a function of the SNP heterogeneity rate estimated on a per SNP basis across all references and the genotyping error rate ($\varepsilon$). It should be noted that the genotyping error rate is user-tunable only via the command-line mode; the fixed default for the UI is 0.02. The default is based on data derived from analysis of HapMap samples. SNPi heterogeneity rate corresponds to the fraction of heterozygous calls for SNPi in all pooled references, excluding the test sample. Hence, a small reference sample-size might introduce errors in this estimation. For un-paired analysis, use of 40 references is considered optimal. This has been determined on the basis of the sensitivity and specificity estimated from ten paired LOH datasets, performed in duplicate, which were subsequently analyzed in un-paired mode. The paired LOH data was considered as the ground truth in this experiment. The number of references was titrated in increments of five from 5-65. The relationship between the prior of LOH and retention is governed by the following property:

$$\pi_{LOH_{sample}} = 1 - \pi_{RET_{sample}} \quad \text{Equation 11}$$

The transition probability for LOH is computed in a manner analogous to that in CN. The only difference here being the prior is a 2×1 as opposed to a 5×1 matrix.

In case of LOH the emission probabilities are computed empirically from the data. This estimation is significantly simpler for the paired case. In the paired case, since only the subset of SNPs with heterozygous calls in the reference is considered, the estimation of the emission probability follows the logic as follows: If the hidden state is an LOH, then the probability the observed state is: i. normal is $\varepsilon$; ii. LOH is 1-$\varepsilon$; If the hidden state is a retention, then the probability the observed state is: iii. LOH is $\varepsilon$; iv. Normal is 1-$\varepsilon$. The emission probability is controlled by the genotyping error rate and hence if this value is set inappropriately, it will adversely affect the estimation of the emission probability. Unlike the paired case, for the un-paired case the observations correspond to genotype calls while the hidden states correspond to LOH or retention. In this case the emission probability for an LOH or retention event from: homozygotes are computed as a function of the genotyping error rate; heterzygotes are computed as a function of the SNP heterogeneity rate.

These probabilities are analogous to the statistical confidence with which a LOH or retention event is observed. The LOH probability is estimated based on the marginal probability of the HMM. The marginal probability of a HMM state is the possibility that we will observe that state without the knowledge of any other events. The retention probability is estimated as 1-LOH probability. Hence, both these values are bounded by [1,0]. While the assignment of the final states in the LOH analysis is based on the Viterbi algorithm the LOH probability is not computed from this; however, a correlation of 98% or higher has been established between the marginal and the Viterbi outcome. The LOH probability, computed as the marginal probability, as a function of the LOH (state=1) and retention (state=2) events. As expected, the LOH events, were observed to have a LOH probability around 1.0, whereas the retention events encompass the entire spectrum from the min (LOH probability) to zero.

The inter-quartile range (IQR) of the $\log_2$ratio is a measure of the variance in the CN estimate across a region of interest (ROI). The ROI could be a chromosome or the entire genome, as sampled by SNPs. The former is referred to as the chromosomal IQR and the latter as the sample IQR For the computation of the IQR the CN data over a ROI is rank-ordered then divided into four quantiles (Q1-Q4), with the IQR measuring the difference between the 2nd and 3rd quantiles: IQR=Q3-Q2. The IQR is a robust analog of the standard deviation measure and it therefore resilient to outliers. For a diploid chromosome an IQR approaching zero is the optimal result as it is indicative of minimal noise in the system.

As discussed before, the logSum method of TCN estimation optimizes for the variance in the CN data, hence a tighter IQR will be observed with the logSum in comparison to sumLog. Therefore, the IQR derived from these two methodologies should not be compared. However, within a given TCN estimation method, it is possible to compare the IQR of the sample versus the individual chromosomes. For the sumLog method, the gaussian smoothing results in improved IQR as demonstrated in FIG. 53. Here the y-axis corresponds to the IQR(left) and x-axis corresponds to sample number. The curve in black and blue refer to the post-PCR normalized but unsmoothed data and the smoothed data respectively. The impact of the smoothing operation on the IQR is not uniform, and as the data for 24 samples show, a reduction of IQR approximating 40% is observed in certain cases. In general the following guidelines hold for use of IQR as a QC metric.

Figure 53:
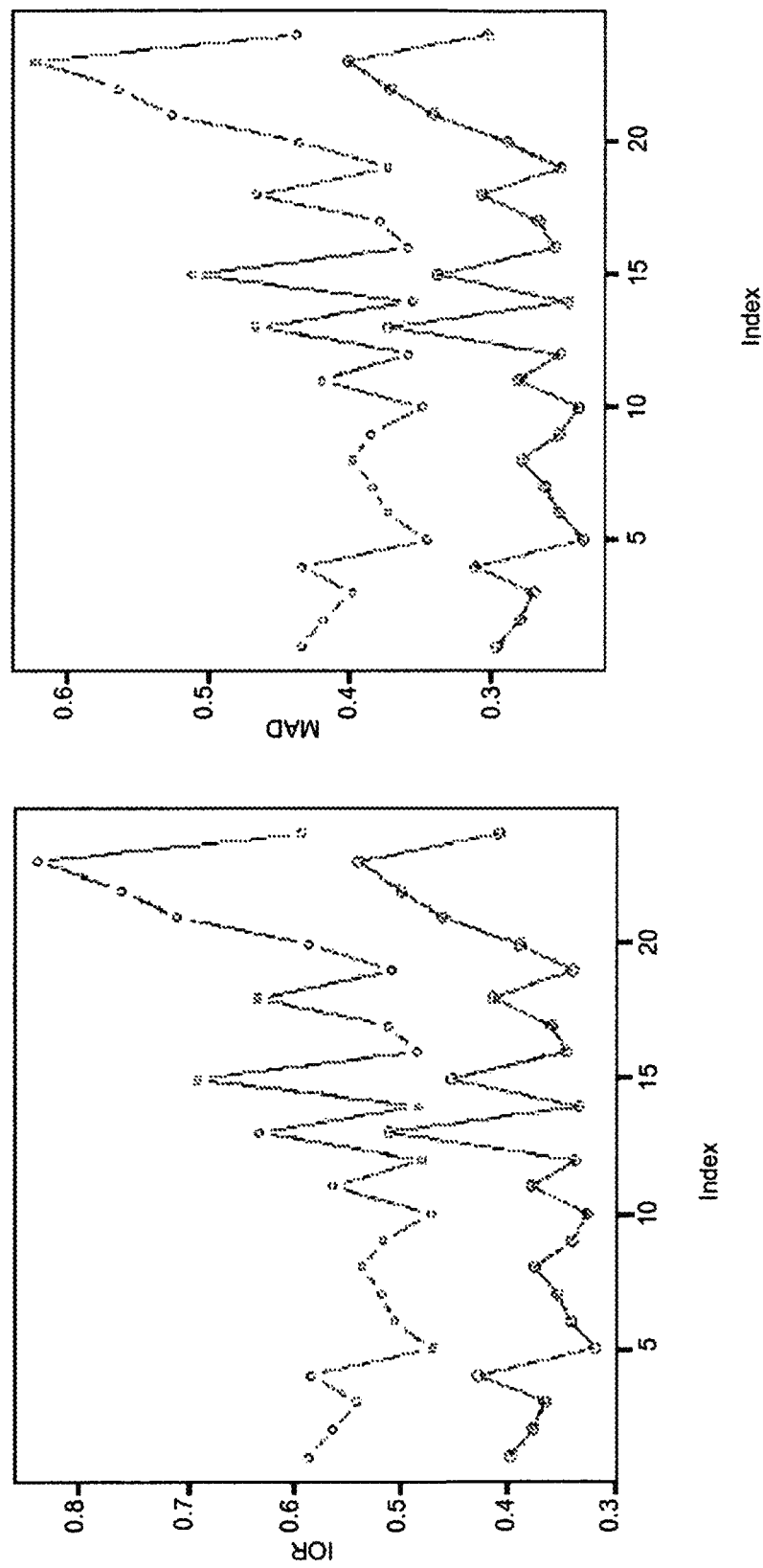
FIG. 53 shows IQR (left) and MAD (right) distribution across 24 samples post PCR correction (upper lines) and post-gaussian smoothing (lower line).

If replicate experiments are performed, consistently higher IQR in some experiments compared to others potentially reflect the introduction of experimental artifacts in the former. Within a given sample, generally the sample IQR should be comparable to the chromosomal IQR. If certain chromosomal IQR show significant variation from the others then the former is probably reflective of true biological changes. Finally, a positive correlation has been observed between chip call-rates and IQR. This relationship is linear at the low end of the CR spectrum potentially <90-95% and levels out above that. Finally, as mentioned before alternative metrics of noise assessment such as standard deviation or median absolute deviation (MAD) as shown in FIG. 53 (IQR and MAD distribution) can be utilized. Analogous to IQR, MAD is a robust metric; nonetheless all metrics of dispersion preserve the trend observed across samples and chromosomes, but only varies in their bounds.

Figure 52:
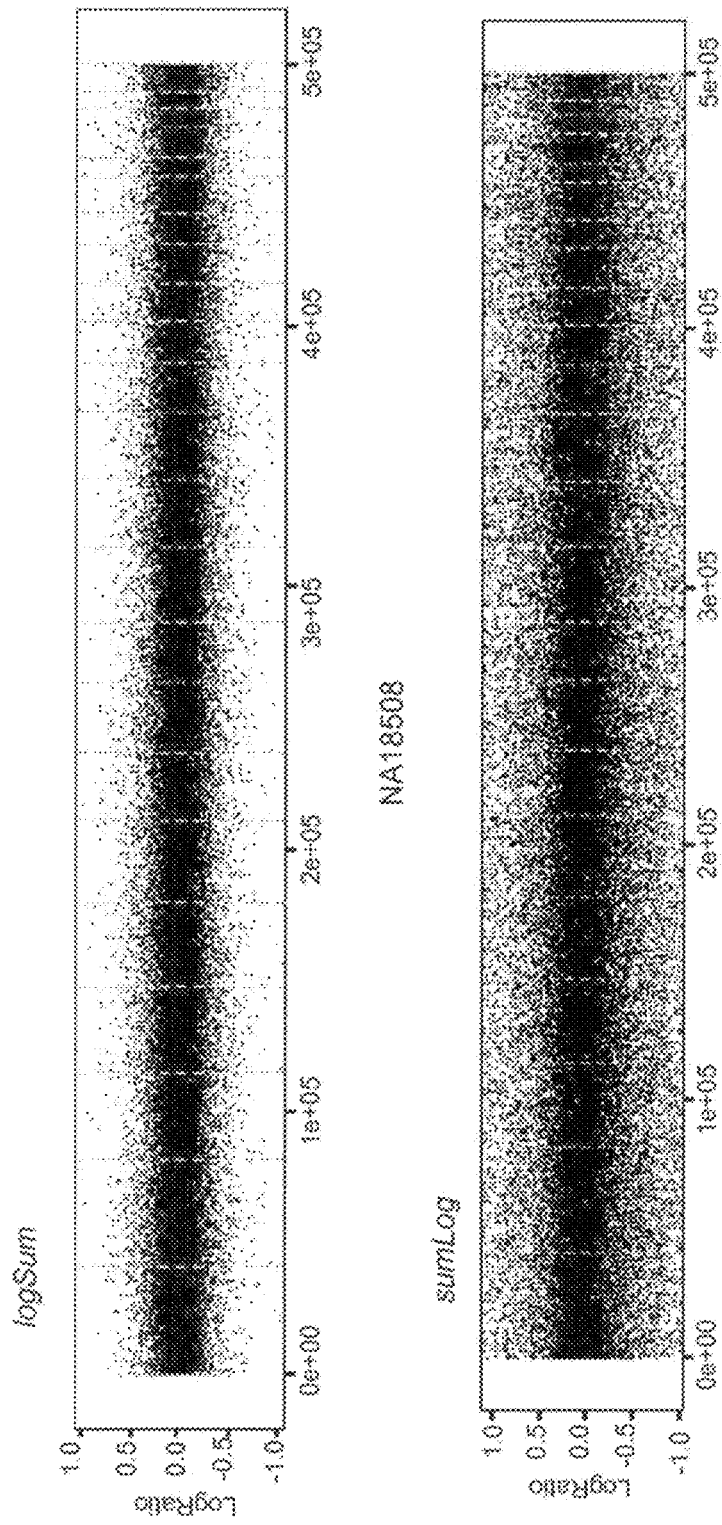
FIG. 52 shows variance distribution for the logSum versus the sumLog options for a normal diploid sample.

The tradeoff demonstrated in FIG. 52, where the y-axis corresponds to the unsmoothed log 2ratio, and x-axis corresponds to the chromosomal location, represents the increased variance in the sumLog option.

The tradeoff on the bias offset is demonstrated in FIG. 52 which shows bias offsets in the pre-PCR normalization (left-panel), the logSum (center panel) and the sumLog (right panel) for the same 4x samples. The horizontal blue line is the line of truth representing a value 1(CN=4). The offset observed in the pre-PCR normalization data is corrected subsequent to the normalization; in case of sumLog the bias correction is appropriate, however in case of logSum the bias is compressed to a value closer to zero. It should be emphasized that the current CN estimation software such as dChipsSNP and CNAG are optimized for variance over bias and hence CNAT 4.0 in the logSum mode provides the best comparison to these methods. The offset example is only shown for the 4x sample but is evident and varies non-linearly in all other titration data, except 2x. ROC analysis, The performance of the algorithm through its various stages has been estimated based on the ROC analysis. Results are shown for post gaussian smoothing where a higher fold performance improvement is observed with 3X than the 4X data. This is shown in FIG. 56, where the y-axis represents the sensitivity and the x-axis the specificity. The left and right panel represent the data for 3x and 4x respectively and the dotted and solid lines refer to the data pre and post gaussian smoothing.

FIG. 56 contrasts the ROC curves post HMM segmentation (red) versus post gaussian smoothing (black). The HMM median log 2ratio values have been used to plot the post HMM data. An ideal curve should represent 100% sensitivity and 100% specificity and therefore approach the top left hand corner of the plot at the lowest false positive rates. As evident from the data, the AUC improves steadily through the sequential steps of PCR normalization, gaussian smoothing and HMM segmentation.

Figure 54:
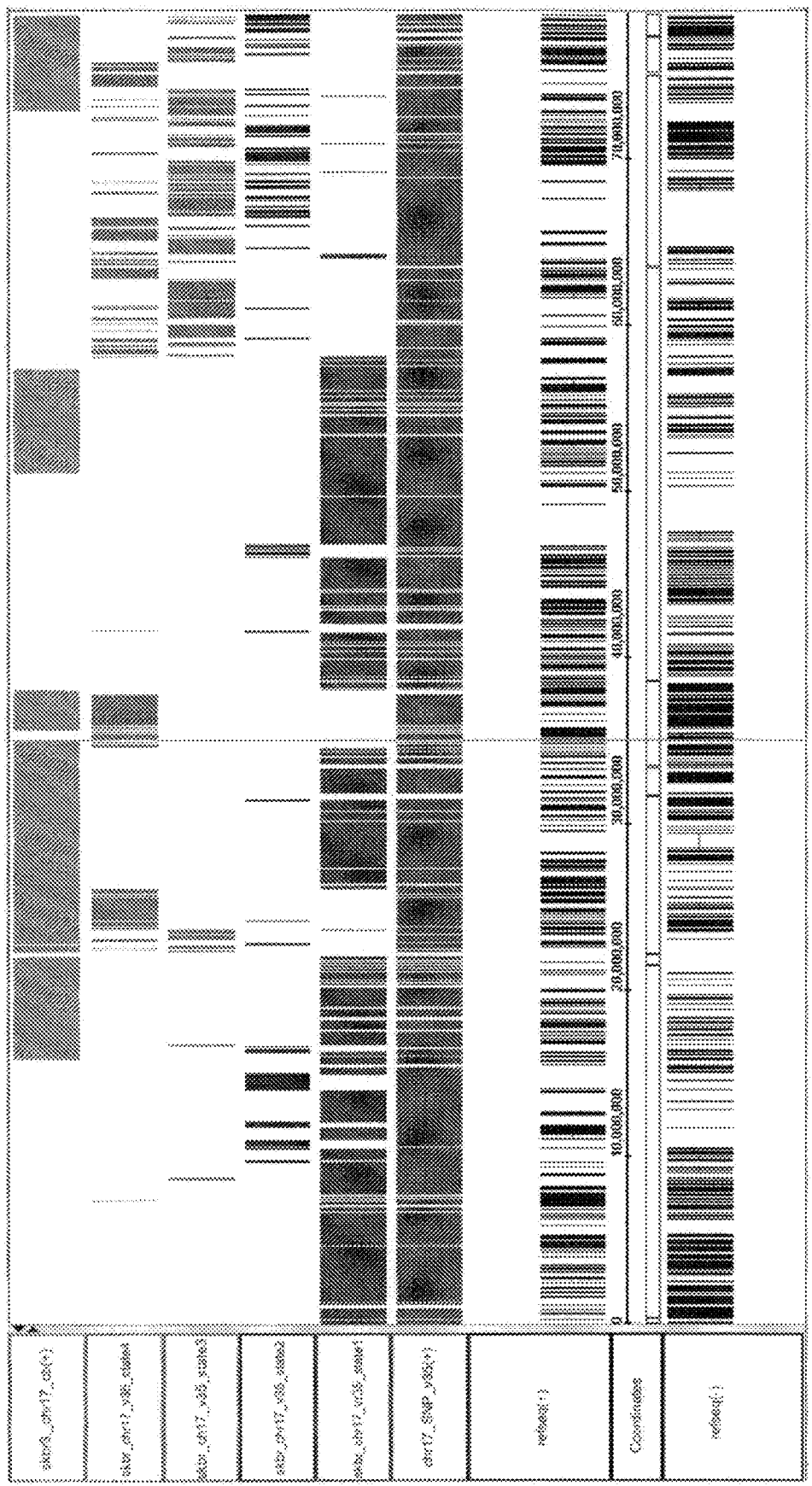
FIG. 54 shows copy number states in chromosome 17 of SK-BR-3 cell line.
Figure 55:
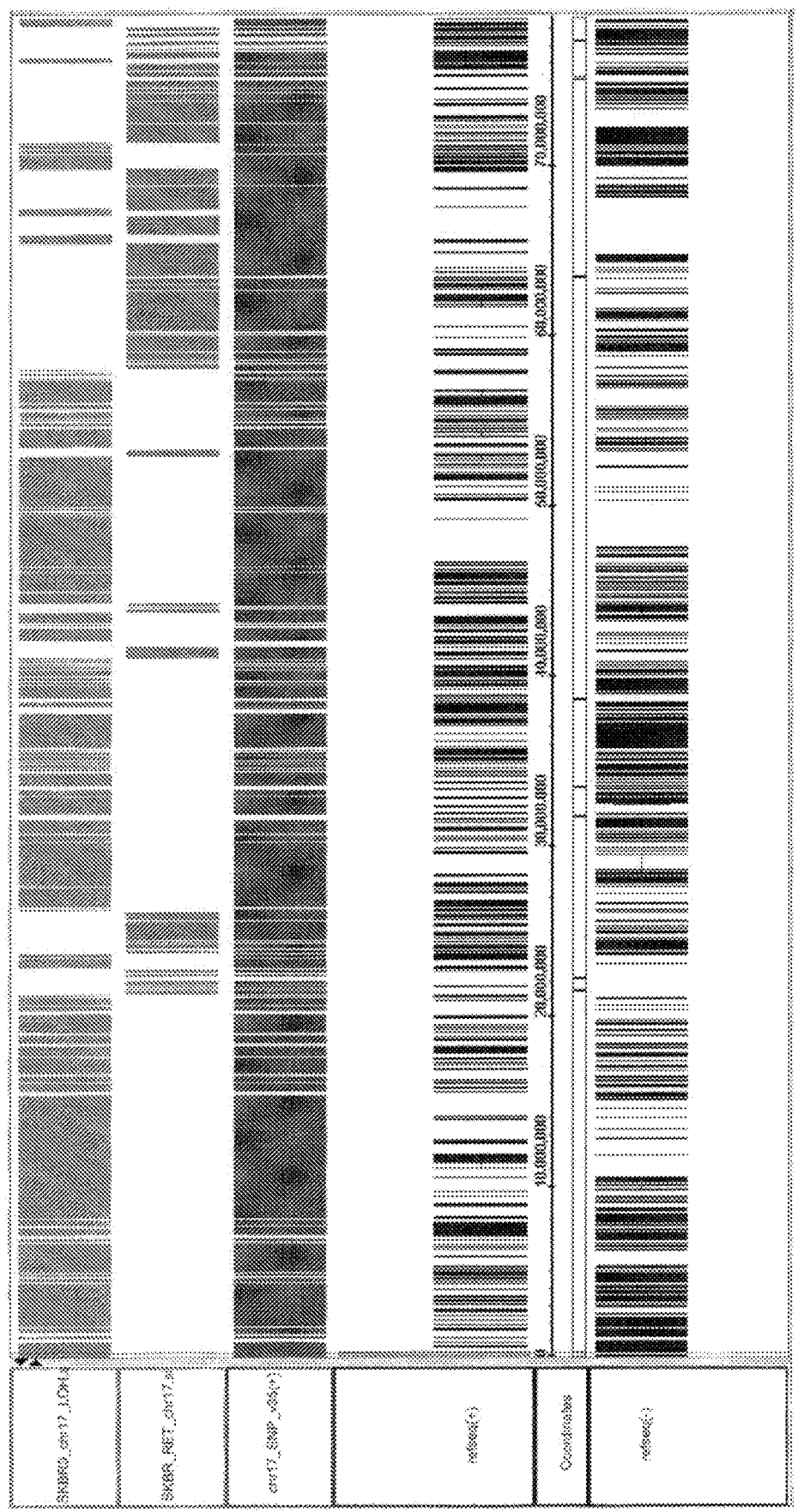
FIG. 55 shows LOH states in chromosome 17 of SK-BR-3 cell line.

An example Integrated Genome Browser screen-shot of both CN and LOH data is shown for chromosome 17 on the SK-BR-3 breast cancer cell-line. The top track in FIG. 54 reflects the cytobands 17q11.2-12, 17q21.2 where both amplifications and deletions have been observed and published in the literature (see, Shadeo A et. Al, Breast Cancer Research, 8:R9 (2006)) and have been confirmed here. Continuing top-down, below the cytoband track are the CN states=4, 3, 2 and 1 tracks, in that order. The track in red reflects the SNP coverage for the chromosome. Approximately 60% of the SNPs are observed in the hemizygous deletion (CN=1) state. FIG. 55 reflects the LOH summary on the same chromosome; the tracks from the top-down represent LOH state, retention state and SNP density. A qualitative comparison of the CN and LOH data shows a significant concordance between observed LOH events and hemizygous deletion.

EXAMPLES

Datasets used for references were from 15 females selected from the HapMap 270, 5 unrealted HapMap Asian samples, and 6 female normal (T/N). The non-HapMap normals used were from tumor normal pairs. Chromosome 1x-5x titration. Un-matched copy number: SK-BR3 breast adenocarcinoma, MCF-7 (HTB22D) breast cancer, CCL-256D non-small cell lung carcinoma. For matched copy number-caucasian male: CCL-256D (non-small cell lung carcinoma) vs. CCL-256.1D (blood). For un-matched LOH: NA10852: 1x (normal male), SKBR3, MCF-7. For matched LOH: CCL-256D vs. CCL-256.1D. For algorithm discussions: 40 operator test datasets.

Virtual Array: create virtual array by combining data from paired array set. Paried arrays are NSP plus corresponding STY array set or Xba plus corresponding HIND array set. For LOH combine two paired arrays and sort based on genomic position. For CN estimation combining data from 2 paired arrays gives false amplification and deletion information. It is important to estimate the noise base-line in paired arrays. Noise is estimated in copy neutral regions which is a user tunable nregion definition. $Log_2(1/2)$ <region<$Log_2(3/2)$. Median stabilization. Sort based on genomic position.

HMM parameter optimization:

Example: Quantification of Amplifications and deletions

Deletions were observed in Chr 18:18×1: Sample 1[1,2]: 74.47%, 24.98% and Sample 2[1,2]: 74.40%, 25.59%. Chr 9: 9×1; t(9,12;11) Sample 1[1,2]: 13.56%, 86% and Sample 2[1,2]: 8%, 92%. Chr 6: 6×1: Sample 1[1,2]: 34.01%, 64.99% and Sample 2[1,2]: 16.1%, 83.9%

Amplifications were observed in: Chr 20: 20×5: Sample 1[4]: 100% and Sample 2[4]: 99.98%. Chr 2: 2×3; t(2;X): Sample 1[2,3]: 61%, 39% and Sample 2[2,3]: 90%, 9.5%. Chr X: Xx2: Sample 1[2,3]: 40%, 58% and Sample 2[2,3]: 40%, 58%. Chr 11: 11×2: Sample 1[ 2,3]: 46%, 53% and Sample 2[2,3]: 46%, 53%.

CONCLUSION

Methods of identifying changes in genomic DNA copy number are disclosed. The methods may be used to detect copy number changes in cancerous tissue compared to normal tissue. A method to identify genome wide copy number gains and losses by hybridization to a genotyping array comprising probes for more than 100,000 human SNPs is disclosed. All cited patents, patent publications and references are incorporated herein by reference for all purposes.

It is to be understood that the above description is intended to be illustrative and not restrictive. Many variations of the invention will be apparent to those of skill in the art upon reviewing the above description. By way of example, the invention has been described primarily with reference to the use of a high density oligonucleotide array, but it will be readily recognized by those of skill in the art that other nucleic acid arrays, other methods of measuring signal intensity resulting from genomic DNA could be used. The scope of the invention should, therefore, be determined not with reference to the above description, but should instead be determined with reference to the appended claims, along with the full scope of equivalents to which such claims are entitled.

What is claimed is:

1. A computer-implemented method for estimating a copy number of each of a plurality of genomic regions in a nucleic acid sample comprising a plurality of nucleic acid molecules, each genomic region containing at least one single nucleotide polymorphism (SNP), the method comprising:
   in an assay, hybridizing on a nucleic acid array comprising a plurality of perfect match probes without corresponding mismatch probes, a plurality of nucleic acid molecules with a plurality of allele-specific perfect match probes for at least one SNP;
   obtaining, by a computer comprising a processor and a memory, an initial intensity measurement for each of the plurality of allele-specific perfect match probes for the at least one SNP, wherein initial intensity measurements obtained for the plurality of allele-specific perfect match probes for the at least one SNP do not include intensities for any mismatch probes;
   generating a global reference from a plurality of control reference samples, wherein the plurality of control reference samples comprises a minimum number of samples estimated by testing for convergence of a distribution of probe-level quantile normalization of SNP data as a function of a number of samples;
   normalizing, by the processor, the global reference and the initial intensity measurement for each of the plurality of allele-specific perfect match probes, resulting in normalized intensity measurements, wherein the normalized intensity measurements are determined for the plurality of allele-specific perfect match probes without utilizing data derived from any mismatch probes;
   calculating, by the processor, an initial copy number estimate for each of the plurality of genomic regions, wherein the initial copy number estimate is based upon the normalized intensity measurements and normalized intensity measurements of the global reference;
   performing, by the processor, data smoothing on the initial copy number estimates, wherein the data smoothing reduces noise within the initial copy number estimates to generate smoothed copy number estimates; and
   estimating, by the processor, the copy number of each of the plurality of genomic regions using a Hidden Markov Model to assign the smoothed copy number estimates to different copy number states.

2. The method of claim 1, further comprising an allele-specific summarization step, wherein summarization values for each allele of the at least one SNP are generated based on the normalized intensity measurements.

3. The method of claim 1, further comprising a filtering step, wherein the initial intensity measurements are filtered to include only intensity measurements from allele-specific perfect match probes corresponding to SNPs that satisfy one or more user-defined metrics, including SNPs on PCR fragments having a fragment length or GC content within a range of threshold values.

4. The method of claim 1, further comprising a filtering step, wherein the initial intensity measurements are filtered to remove initial intensity measurements based upon one or more metrics, including at least chemical or scanner probe saturation.

5. The method of claim 1, wherein performing data smoothing comprises a method of smoothing selected from the group consisting of Gaussian smoothing, Lowess smoothing, and Spline smoothing.

6. The method of claim 1, wherein the plurality of allele-specific perfect match probes is located on two or more arrays, wherein the method further comprises a virtual array generation step, and wherein the virtual array reduces variance between the two or more arrays.

7. The method of claim 1, wherein the normalizing step comprises median scaling, wherein a median value is computed based on intensity of all of the plurality of allele-specific perfect match probes.

8. The method of claim 1, wherein the initial copy number estimates are calculated based on log 2 transformations of the normalized intensity measurements.

9. The method of claim 1, wherein the initial copy number estimates are calculated using the following equation:

$$TCN = \log_2\left[\frac{S_A}{R_A + R_B} + \frac{S_B}{R_A + R_B},\right]$$

wherein $S_A$ comprises the normalized intensity measurement for a first allele of a SNP within the nucleic acid sample, $S_B$ comprises the normalized intensity measurement for a second allele of the SNP within the nucleic acid sample, $R_A$ comprises the normalized intensity measurement for the first allele of the SNP within the global reference, and $R_B$ comprises the normalized intensity measurement for the second allele of the SNP within the global reference.

10. The method of claim 1, wherein the first assay further comprises a plurality of nucleic acid samples used to generate the global reference.

11. The method of claim 1, wherein the plurality of control samples comprises between 10 and 40 samples.

12. The method of claim 1, wherein the plurality of control samples is matched to the nucleic acid sample in either ethnicity or gender.

13. The method of claim 1, wherein the global reference is generated from a plurality of data files corresponding to the plurality of control samples.

14. The method of claim 1, wherein the global reference is optimized by sampling at random from a plurality of available control samples.

15. The method of claim 1, wherein the global reference is optimized using quantile normalization.

16. A system for estimating a copy number of each of a plurality of genomic regions in a nucleic acid sample comprising a plurality of nucleic acid molecules, each genomic region comprising at least one single nucleotide polymorphism (SNP), the system comprising:
   a nucleic acid array comprising a plurality of perfect match probes wherein each of the plurality of perfect match probes does not have a corresponding mismatch probe, and the array is configured to hybridize at least some nucleic acid molecules in a nucleic acid sample with a plurality of allele-specific perfect match probes for at least one SNP on the nucleic acid array;

a computer; and a computer software program configured to execute on the computer, causing the computer to:

obtain an initial intensity measurement for each of a plurality of allele-specific perfect match probes on nucleic acid array for at least one SNP in each genomic region, after the plurality of nucleic acid molecules in the nucleic acid sample have been hybridized with the plurality of allele-specific perfect match probes, wherein the initial intensity measurements obtained do not include intensities for any mismatch probes;

generate a global reference from a plurality of control reference samples, wherein the plurality of control reference samples comprises a minimum number of samples estimated by testing for convergence of a distribution of probe-level quantile normalization of SNP data as a function of a number of samples;

normalize the initial intensity measurement for the global reference and for each of the plurality of allele-specific perfect match probes, resulting in normalized intensity measurements, wherein the normalized intensity measurements are determined for the plurality of allele-specific perfect match probes without utilizing any data derived from any mismatch probes;

calculate an initial copy number estimate for each of the plurality of genomic regions, wherein the initial copy number estimate is based upon the normalized intensity measurements for each of the plurality of allele-specific perfect match probes and the global reference;

perform data smoothing on the initial copy number estimates, wherein the data smoothing reduces noise within the initial copy number estimates to generate smooth copy number estimates; and estimate the copy number of each of the plurality of genomic regions using a Hidden Markov Model to assign the smoothed copy number estimates to different copy number states.

17. The system of claim 16, wherein the computer software program is additionally configured to output to a display an indication of the copy number for each of the plurality of genomic regions.

18. The system of claim 16, wherein the computer software program is additionally configured to output to a display an indication of an allele-specific copy number for each of the plurality of genomic regions.

19. The system of claim 16, wherein the computer software program is further configured to filter the plurality of allele-specific perfect match probes to exclude probes based on at least one of a length and a GC content of a nucleic acid molecule on which the at least one SNP resides.

20. A computer-implemented method for estimating a copy number of each of a plurality of genomic regions in a nucleic acid sample comprising a plurality of nucleic acid molecules, each genomic region containing at least one single nucleotide polymorphism (SNP), the method comprising:

hybridizing at least some nucleic acid molecules in a nucleic acid sample with a plurality of allele-specific perfect match probes for at least one SNP provided in a nucleic acid array comprising a plurality of perfect match probes wherein each of the plurality of perfect match probes does not have a corresponding mismatch probe;

obtaining, by a computer comprising a processor and a memory, an initial intensity measurement from each of the plurality of allele-specific perfect match probes for at least one SNP, after the plurality of nucleic acid molecules in the nucleic acid sample have been hybridized with the plurality of allele-specific perfect match probes, and the initial intensity measurements obtained do not include intensities for any mismatch probes;

filtering the allele-specific perfect match probes for the SNPs based on one or more user-defined metrics;

generating a global reference from a plurality of control reference samples, wherein the plurality of control reference samples comprises a minimum number of samples estimated by testing for convergence of a distribution of probe-level quantile normalization of SNP data as a function of a number of samples;

normalizing, by the processor, the initial intensity measurement for the global reference and for each of the plurality of allele-specific perfect match probes, resulting in normalized intensity measurements, wherein the normalized intensity measurements are determined for the plurality of allele-specific perfect match probes without utilizing any data derived from mismatch probes;

calculating, by the processor, an initial copy number estimate for each of the plurality of genomic regions, wherein the initial copy number estimate is based upon the normalized intensity measurements for the plurality of allele-specific perfect match probes and for the global reference;

performing, by the processor, data smoothing on the initial copy number estimates, wherein the data smoothing reduces noise within the initial copy number estimates to generate smoothed copy number estimates; and estimating, by the processor, the copy number of each of the plurality of genomic regions using a Hidden Markov Model to assign the smoothed copy number estimates to different copy number states.

* * * * *